US012662473B2

(12) United States Patent
Tan et al.

(10) Patent No.: US 12,662,473 B2
(45) Date of Patent: Jun. 23, 2026

(54) INHIBITORS FOR PROGRAMMED CELL NECROSIS AND PREPARATION METHOD THEREFOR AND USE THEREOF

(71) Applicant: SHANGHAI INSTITUTE OF ORGANIC CHEMISTRY, CHINESE ACADEMY OF SCIENCES, Shanghai (CN)

(72) Inventors: Li Tan, Shanghai (CN); Ying Qin, Shanghai (CN)

(73) Assignee: SHANGHAI INSTITUTE OF ORGANIC CHEMISTRY, CHINESE ACADEMY OF SCIENCES, Shanghai (CN)

( * ) Notice: Subject to any disclaimer, the term of this patent is extended or adjusted under 35 U.S.C. 154(b) by 1041 days.

(21) Appl. No.: 17/455,807

(22) Filed: Mar. 30, 2022

(65) Prior Publication Data

US 2022/0213077 A1 Jul. 7, 2022

Related U.S. Application Data

(63) Continuation-in-part of application No. PCT/CN2020/091388, filed on May 20, 2020.

(30) Foreign Application Priority Data

May 21, 2019 (CN) ......................... 201910425587.3

(51) Int. Cl.

| | |
|---|---|
| ***C07D 413/04*** | (2006.01) |
| ***C07D 207/06*** | (2006.01) |
| ***C07D 207/08*** | (2006.01) |
| ***C07D 207/09*** | (2006.01) |
| ***C07D 231/04*** | (2006.01) |
| ***C07D 231/06*** | (2006.01) |
| ***C07D 401/04*** | (2006.01) |
| ***C07D 401/12*** | (2006.01) |
| ***C07D 403/04*** | (2006.01) |
| ***C07D 403/06*** | (2006.01) |
| ***C07D 403/12*** | (2006.01) |
| ***C07D 417/04*** | (2006.01) |
| ***C07D 417/12*** | (2006.01) |

(52) U.S. Cl.

CPC ......... *C07D 413/04* (2013.01); *C07D 207/06* (2013.01); *C07D 207/08* (2013.01); *C07D 207/09* (2013.01); *C07D 231/04* (2013.01); *C07D 231/06* (2013.01); *C07D 401/04* (2013.01); *C07D 401/12* (2013.01); *C07D 403/04* (2013.01); *C07D 403/06* (2013.01); *C07D 403/12* (2013.01); *C07D 417/04* (2013.01); *C07D 417/12* (2013.01); *C07B 2200/05* (2013.01)

(58) Field of Classification Search

CPC .. C07D 207/06; C07D 413/04; C07D 231/04; C07D 403/04

See application file for complete search history.

(56) References Cited

U.S. PATENT DOCUMENTS 9,586,880 B2 * 3/2017 Yuan ....................... A61P 31/04

FOREIGN PATENT DOCUMENTS

| | | | |
|---|---|---|---|
| CN | 1678609 | A | 10/2005 |
| CN | 102316735 | A | 1/2012 |
| WO | 9710712 | A1 | 3/1997 |
| WO | 2009023272 | A1 | 2/2009 |
| WO | 2012125544 | A2 | 9/2012 |

OTHER PUBLICATIONS

International Search Report (with English translation) and Written Opinion issued in PCT/CN2020/091388, dated Aug. 11, 2020.

* cited by examiner

*Primary Examiner* — Kamal A Saeed
(74) *Attorney, Agent, or Firm* — HSML P.C.

(57) ABSTRACT

Provided in the present invention are inhibitors for programmed cell necrosis, a preparation method therefor and a use thereof. Specifically, provided in the present invention are a compound represented by formula I and a composition comprising same. The described compound may be used to prepare a pharmaceutical composition for the prevention and/or treatment of diseases involving cell death and/or inflammation.

(I)

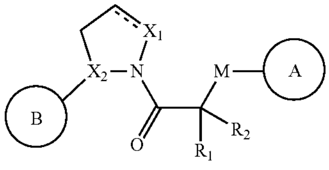

9 Claims, 3 Drawing Sheets

INHIBITORS FOR PROGRAMMED CELL NECROSIS AND PREPARATION METHOD THEREFOR AND USE THEREOF

FIELD OF THE INVENTION

The present invention relates to the field of small molecule compounds, in particular, the present invention provides an inhibitor with novel structure for inhibiting programmed cell necrosis and/or human receptor interacting protein 1 kinase (RIPK1), and preparation method therefor and use thereof.

BACKGROUND TECHNIQUE

In the process of development and aging, the human body is always accompanied by dynamic regulation of cell proliferation and cell death. Active cell death is indispensable in normal development, the invasion resistance of pathogenic microorganisms, maintaining the internal environment homeostasis and other physiological activities, and its imbalance often leads to developmental malformation, immune system diseases, neurodegenerative diseases, cancer and other diseases, and even death of the individual. Therefore, intervention on programmed cell death is of great significance for disease treatment research. Apoptosis is the first elucidated mechanism of programmed cell death. In recent years, programmed cell necrosis has become a new hot spot in the field of cell death. It has been reported in many studies that it is accompanied by the important pathological feature of programmed cell necrosis in various diseases such as various degenerative diseases (such as Alzheimer's disease (AD), multiple sclerosis (MS), amyotrophic lateral sclerosis (ALS), retinal degenerative diseases, etc.), inflammation (enteritis, rheumatoid arthritis, psoriasis, etc.), ischemia-reperfusion injury (cerebral infarction, myocardial infarction, etc.), and pathogen infection and the like. In addition, programmed cell necrosis is also involved in the regulation of the tumor microenvironment: lung cancer cells can induce programmed necrosis of specific cells in the blood vessel wall in order to pass through the circulatory system and metastasize; high expression of the main component of necrosomes in pancreatic cancer can induce the expression of chemokine CXCL1 and inhibit the immune response of the body. Therefore, inhibiting the occurrence of programmed cell necrosis is recognized as helpful for the treatment and alleviation of various diseases.

Studies have shown that tumor necrosis factor α (TNF-α) is one of the main ways to stimulate programmed necrosis of cells in vivo, and its downstream signaling pathway is also the necrosis signaling pathway with the most clear mechanism. In the classical TNF-α-induced cell necrosis process, TNF-α first binds to the receptor TNFR1, induces its trimerization and recruits a series of intracellular factors including multiple proteins such as TRADD, TRAF2, RIPK1, cIAP1/2 and the like, thereby forming signaling complex I. Complex I can recruit and activate the IKKα/IKKβ/IKKγ complex and the NF-κB pathway, and partially enter the cytoplasm after dissociation to form a new protein complex IIa, then recruit procaspase-8 and other proteins through FADD or TRADD to activate the downstream caspases including caspase-3 and caspase-7 and mediate the occurrence of apoptosis. In the absence of FADD or the administration of caspase inhibitors, the kinase protein RIPK1 induced and activated by TNF-α binds to RIPK3 to form a new complex IIb and induces phosphorylation activation of the latter, which phosphorylates the downstream substrate MLKL to promote its oligomerization, and eventually disrupts the structure of the cell membrane and leads to necrosis.

Multiple adaptor proteins, ubiquitin ligases, deubiquitinases and kinase proteins are involved in regulating the downstream signaling pathways of TNF-α-induced programmed cell necrosis. For example, the K63 ubiquitination of RIPK1 by the E3 ubiquitin ligase cIAP can inhibit the activation of latter and the process of necrosis; the deubiquitinase CYLD can cleave the K63 ubiquitin chain of RIPK1, thereby activating RIPK1 kinase activity and promoting the formation of necrosome, and eventually achieving positive regulation of cell necrosis; the adaptor protein SPATA2 promotes the activity of CYLD deubiquitinase and inhibits the NF-κB and MAPK signaling pathways, thereby positively regulating programmed necrosis; the kinase protein TAK1 inhibits the kinase activity of RIPK1 by phosphorylating Ser321 site of RIPK1, thereby negatively regulating programmed necrosis, while deubiquitinating enzyme A20 (TNF-α induced protein 3), adaptor protein TAB2 (TAK1 binding protein 2) and other regulation factors are also involved in this regulatory process; the kinase protein TBK1 inhibits the activation of the RIPK1 by phosphorylating the Thr189 site of RIPK1, and the inactivating mutation of TBK1 during aging is also an important pathogenic risk for neurodegenerative diseases such as ALS and FTD; the adaptor protein Optineurin (OPTN) negatively regulates programmed necrosis by inhibiting RIPK1 kinase activity, and loss of OPTN in ALS may contribute to progressive dysmyelination and axonal degeneration. It can be seen that in the signaling pathway network of TNF-α-induced programmed cell necrosis, the functional abnormalities of multiple regulatory components mediate the occurrence of programmed necrosis through the activation of RIPK1 kinase (the core regulatory factor).

Therefore, RIPK1 kinase is recognized as a potential therapeutic target for diseases related to programmed cell necrosis. The first-in-class RIPK1 inhibitor Necrostatin-1 (Nec-1) and analogs thereof have demonstrated clear curative effects on a variety of degenerative diseases, inflammation, cancer and other diseases in preclinical studies. For example, it has relieving effect on AD, ALS, MS, Parkinson's disease (PD), Huntington's disease (PD), inflammatory bowel disease, age-related macular degeneration, etc.; it has protective effect on psoriasis, retinitis pigmentosa, inflammatory bowel disease, autoimmune diseases, bombesin-induced acute pancreatitis and sepsis/systemic inflammatory response syndrome (SIRS); it can effectively alleviate ischemic brain injury, ischemic myocardial injury, retinal ischemia/regperfusion injury, retinal detachment-induced photoreceptor cell necrosis, glaucoma, renal ischemia-reperfusion injury, cisplatin-induced renal injury, and traumatic brain injury; relieves at least partially other diseases associated with RIPK1-dependent apoptosis, necrosis, or cytokine production, including hematological malignancies and solid organ malignancies, bacterial infections and viral infections (including tuberculosis, influenza, etc.), and lysosomal storage disorders (especially Gaucher disease). Currently, Nec-1 derivatives have entered clinical trials for the treatment of ALS and AD; another class of RIPK1 inhibitor GSK2982772 is also in clinical trials for the treatment of various autoimmune diseases. However, all the existing programmed necrosis inhibitors have different degrees of defects, such as unsatisfactory in vivo inhibitory activity, poor pharmacokinetic properties, low oral bioavailability and the like, and some cannot enter the central nervous system through the blood-brain barrier, or some are difficult to carry out preclinical animal trials because some cannot effectively inhibit murine RIPK1. These shortcomings limit their further research and clinical application.

Therefore, the development of small molecule inhibitor of RIPK1 kinase activity with high specificity, high activity and blood-brain barrier penetration with clinical application value is a difficulty and hot spot in the current research on the treatment of programmed cell necrosis-related diseases. On the basis of the existing RIPK1 kinase inhibitors, there is still a need in the art for novel RIPK1 inhibitors with more novel chemical structures and more outstanding pharmacokinetic and pharmacodynamic properties, which can be used as drug candidates for the prevention and treatment of involving cell death and/or inflammatory diseases.

SUMMARY OF THE INVENTION

The purpose of the present invention is to provide a novel RIPK1 inhibitor with novel chemical structure and more outstanding pharmacokinetic and pharmacodynamic property, which can be used as drug candidates for the prevention and treatment of diseases involving cell death and/or inflammation.

The first aspect of the present invention provides a compound represented by the following Formula (I), or pharmaceutically acceptable salts thereof,

I

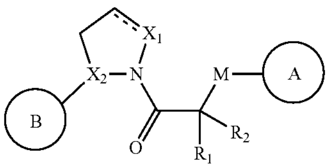

wherein:

dashed line is a chemical bond or none;

M is selected from the group consisting of S, O and NH;

$X_1$ is selected from the group consisting of $CR_2$, NR, O, S, CR and N;

$X_2$ is selected from the group consisting of CR and N;

R is selected from the group consisting of H, D and C1-C4 alkyl;

$R_1$ and $R_2$ are each independently selected from the the group consisting of H and C1-C4 alkyl; or $R_1$ and $R_2$ together form a structure of substituted or unsubstituted $-(CH_2)_n-$; wherein, n is 1, 2, 3 or 4;

ring A is selected from the group consisting of substituted or unsubstituted C6-C10 aryl and substituted or unsubstituted 5-12 membered heteroaryl;

ring B is selected from the group consisting of substituted or unsubstituted C6-C10 aryl and substituted or unsubstituted 5-12 membered heteroaryl;

wherein, the substituted means that the hydrogen atoms on the groups are substituted by one or more (such as 2, 3, 4, etc.) substituents selected from the group consisting of halogen, deuterium, C1-C6 alkoxy, halogenated C1-C6 alkoxy, methyl sulfonyl, $-S(=O)_2NH_2$, oxo(=O), —CN, hydroxyl, $-NH_2$, carboxyl, C2-C6 amido($-C(=O)-N(Rc)_2$ or —NH—C(=O)(Rc), Rc is H or C1-C5 alkyl), C1-C6 alkyl-(C2-C6 amido), or substituted or unsubstituted groups selected from the group consisting of C1-C6 alkyl, C3-C8 cycloalkyl, C1-C6 amino, C6-C10 aryl, 5-10 membered heteroaryl having 1-3 heteroatoms selected from N, S and O, 5-12 membered heterocyclyl having 1-3 heteroatoms selected from N, S and O, $-(CH_2)-$C6-C10 aryl, and $-(CH_2)-$(5-10 membered heteroaryl having 1-3 heteroatoms selected from N, S and O), and the substituents are selected from the group consisting of halogen, C1-C6 alkyl, C1-C6 alkoxy, oxo, —CN, $-NH_2$, —OH, C6-C10 aryl, C1-C6 amino, C2-C6 amido, and 5-10 membered heteroaryl having 1-3 heteroatoms selected from N, S and O.

In another preferred embodiment, the compound of formula I has a structure selected from the group consisting of I-a and I-b:

I-a

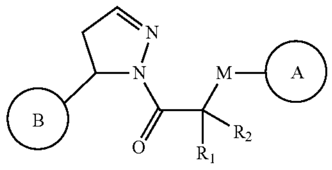

I-b

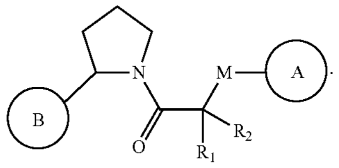

In another preferred embodiment, the compound of formula I has a structure shown in the following formula I-c:

I-c

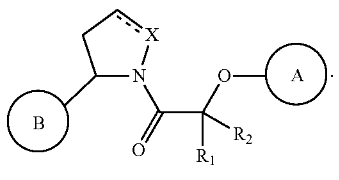

In another preferred embodiment, ring A is selected from the group consisting of substituted or unsubstituted phenyl, and substituted or unsubstituted 5-7 membered heteroaryl; and/or ring B is selected from the group consisting of substituted or unsubstituted phenyl, and substituted or unsubstituted 5-7 membered heteroaryl.

In another preferred embodiment, ring A is a substituted or unsubstituted phenyl.

In another preferred embodiment, the compound is selected from the following table:

| Compound nunber | Chemical structure | Compound nunber | Chemical structure |
|---|---|---|---|
| QY-1-98 | 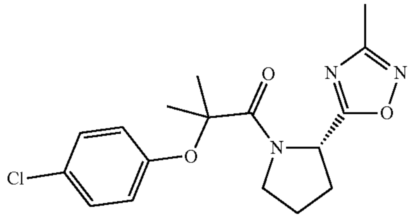 [SMILES: Cc1noc([C@@H]2CCCN2C(=O)C(C)(C)Oc2ccc(Cl)cc2)n1] | QY-4-6 | 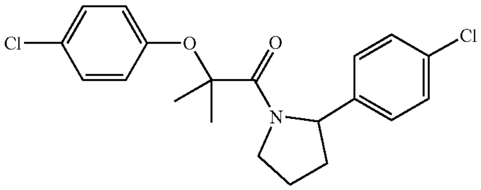 [SMILES: CC(C)(Oc1ccc(Cl)cc1)C(=O)N1CCCC1c1ccc(Cl)cc1] |
| QY-2-25 | 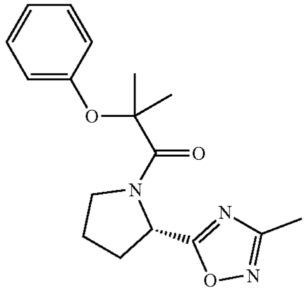 [SMILES: Cc1noc([C@@H]2CCCN2C(=O)C(C)(C)Oc2ccccc2)n1] | QY-4-7 | 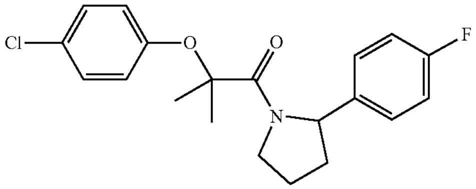 [SMILES: CC(C)(Oc1ccc(Cl)cc1)C(=O)N1CCCC1c1ccc(F)cc1] |
| QY-2-26 | 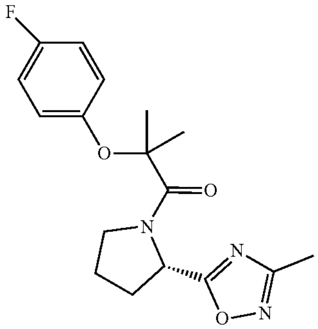 [SMILES: Cc1noc([C@@H]2CCCN2C(=O)C(C)(C)Oc2ccc(F)cc2)n1] | QY-4-8 | 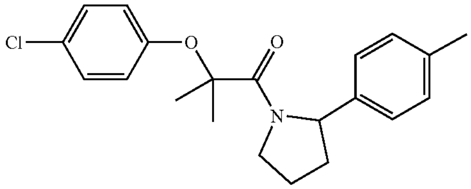 [SMILES: Cc1ccc(C2CCCN2C(=O)C(C)(C)Oc2ccc(Cl)cc2)cc1] |
| QY-2-27 | 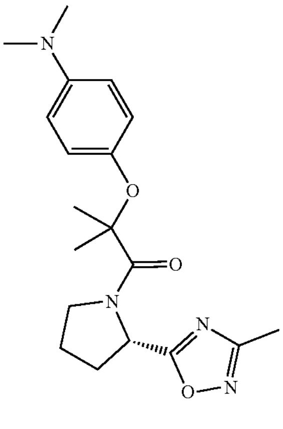 | QY-4-11 | 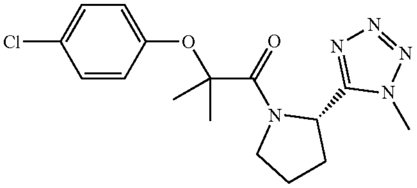 [SMILES: Cn1nnnc1[C@@H]1CCCN1C(=O)C(C)(C)Oc1ccc(Cl)cc1] |

-continued
| Compound nunber | Chemical structure | Compound nunber | Chemical structure |
|---|---|---|---|
| QY-2-34 | 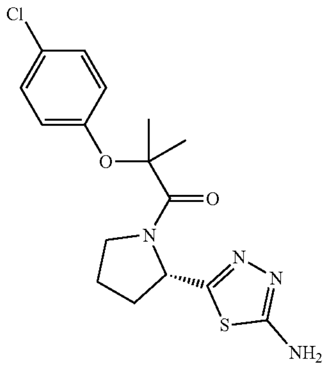 [SMILES: CC(C)(Oc1ccc(Cl)cc1)C(=O)N1CCC[C@H]1c1nnc(N)s1] | QY-4-12 | 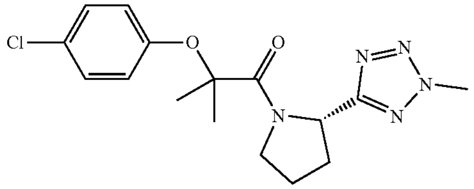 [SMILES: Cn1nnc([C@@H]2CCCN2C(=O)C(C)(C)Oc2ccc(Cl)cc2)n1] |
| QY-2-38 | 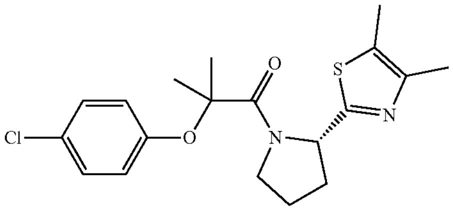 [SMILES: Cc1nc([C@@H]2CCCN2C(=O)C(C)(C)Oc2ccc(Cl)cc2)sc1C] | QY-4-14 | 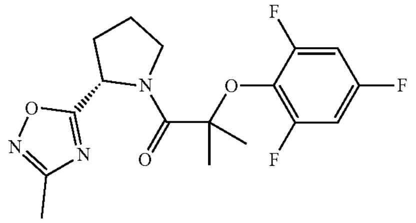 [SMILES: Cc1noc([C@@H]2CCCN2C(=O)C(C)(C)Oc2c(F)cc(F)cc2F)n1] |
| QY-2-39 | 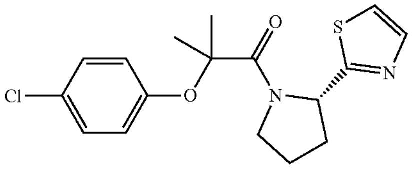 [SMILES: CC(C)(Oc1ccc(Cl)cc1)C(=O)N1CCC[C@H]1c1nccs1] | QY-4-27 | 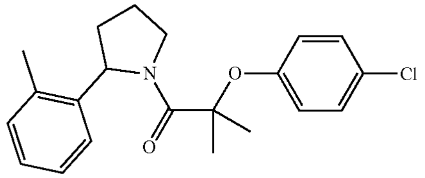 [SMILES: Cc1ccccc1C1CCCN1C(=O)C(C)(C)Oc1ccc(Cl)cc1] |
| QY-2-52 | 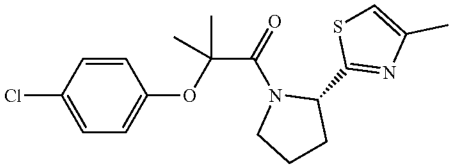 [SMILES: Cc1csc([C@@H]2CCCN2C(=O)C(C)(C)Oc2ccc(Cl)cc2)n1] | QY-4-32 | 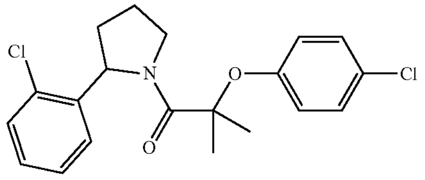 [SMILES: CC(C)(Oc1ccc(Cl)cc1)C(=O)N1CCCC1c1ccccc1Cl] |
| QY-2-53 | 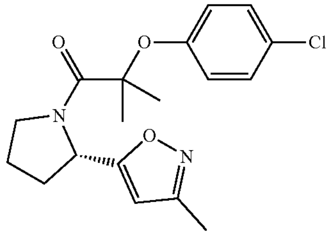 [SMILES: Cc1cc([C@@H]2CCCN2C(=O)C(C)(C)Oc2ccc(Cl)cc2)on1] | QY-4-35 | 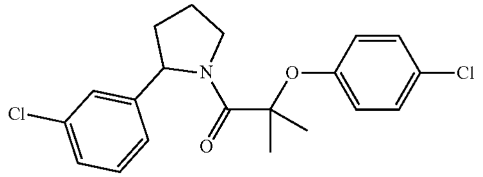 [SMILES: CC(C)(Oc1ccc(Cl)cc1)C(=O)N1CCCC1c1cccc(Cl)c1] |

-continued
| Compound nunber | Chemical structure | Compound nunber | Chemical structure |
|---|---|---|---|
| QY-2-54 | 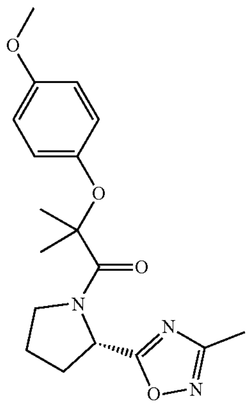 [SMILES: COc1ccc(OC(C)(C)C(=O)N2CCC[C@H]2c2nc(C)no2)cc1] | QY-4-39 | 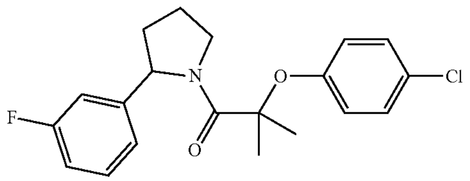 [SMILES: CC(C)(Oc1ccc(Cl)cc1)C(=O)N1CCCC1c1cccc(F)c1] |
| QY-2-55 | 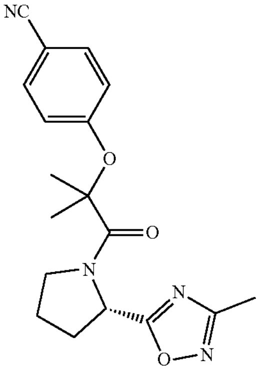 [SMILES: Cc1noc([C@@H]2CCCN2C(=O)C(C)(C)Oc2ccc(C#N)cc2)n1] | QY-4-66 | 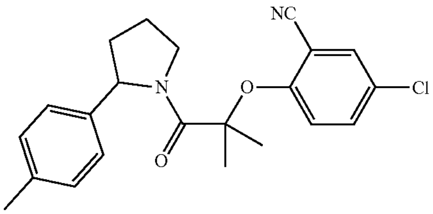 [SMILES: Cc1ccc(C2CCCN2C(=O)C(C)(C)Oc2ccc(Cl)cc2C#N)cc1] |
| QY-2-56 | 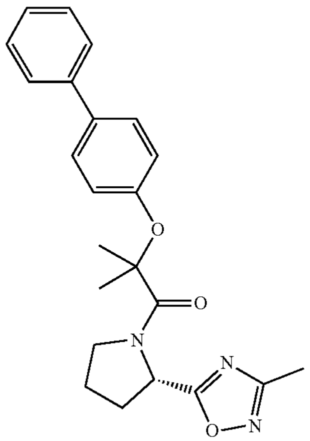 [SMILES: Cc1noc([C@@H]2CCCN2C(=O)C(C)(C)Oc2ccc(-c3ccccc3)cc2)n1] | QY-4-67 | 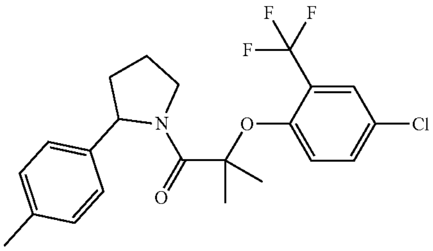 [SMILES: Cc1ccc(C2CCCN2C(=O)C(C)(C)Oc2ccc(Cl)cc2C(F)(F)F)cc1] |
| QY-2-75 | 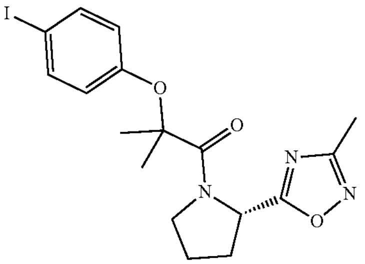 [SMILES: Cc1noc([C@@H]2CCCN2C(=O)C(C)(C)Oc2ccc(I)cc2)n1] | QY-4-69 | 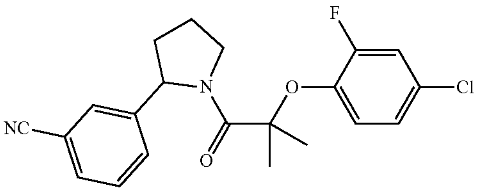 [SMILES: CC(C)(Oc1ccc(Cl)cc1F)C(=O)N1CCCC1c1cccc(C#N)c1] |

-continued
| Compound nunber | Chemical structure | Compound nunber | Chemical structure |
|---|---|---|---|
| QY-2-76 | 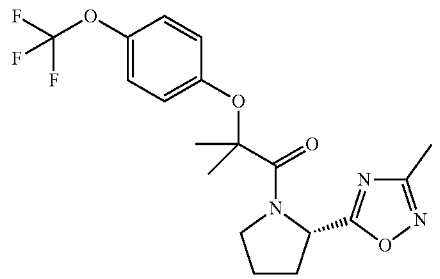 [SMILES: Cc1noc([C@@H]2CCCN2C(=O)C(C)(C)Oc2ccc(OC(F)(F)F)cc2)n1] | QY-4-70 | 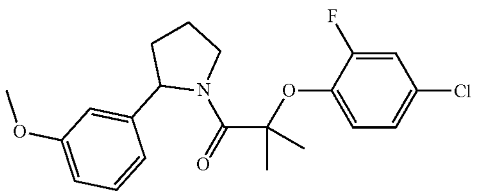 [SMILES: COc1cccc(C2CCCN2C(=O)C(C)(C)Oc2ccc(Cl)cc2F)c1] |
| QY-2-77 | 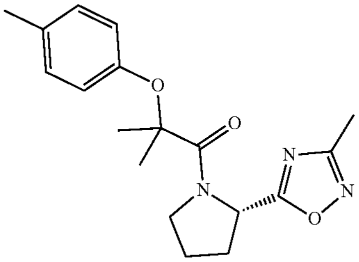 | QY-4-75 | 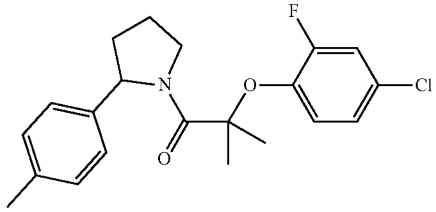 [SMILES: Cc1ccc(C2CCCN2C(=O)C(C)(C)Oc2ccc(Cl)cc2F)cc1] |
| QY-2-78 | 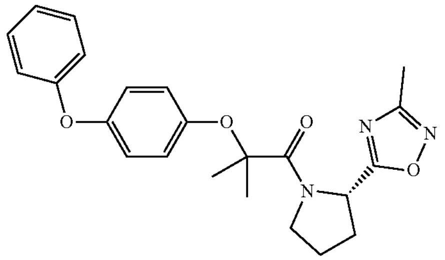 [SMILES: Cc1noc([C@@H]2CCCN2C(=O)C(C)(C)Oc2ccc(Oc3ccccc3)cc2)n1] | QY-4-78 | 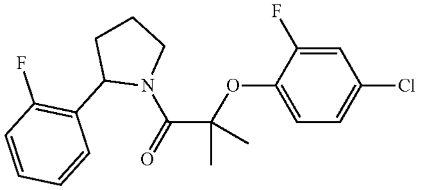 [SMILES: CC(C)(Oc1ccc(Cl)cc1F)C(=O)N1CCCC1c1ccccc1F] |
| QY-2-79 | 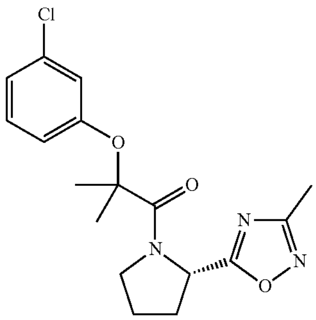 [SMILES: Cc1noc([C@@H]2CCCN2C(=O)C(C)(C)Oc2cccc(Cl)c2)n1] | QY-4-87 | 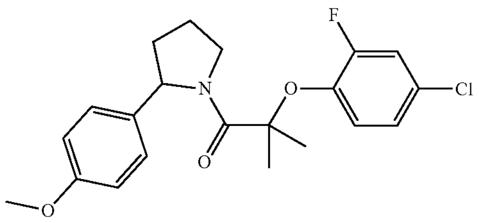 [SMILES: COc1ccc(C2CCCN2C(=O)C(C)(C)Oc2ccc(Cl)cc2F)cc1] |
| QY-2-100 | 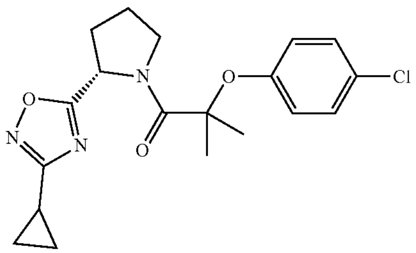 [SMILES: CC(C)(Oc1ccc(Cl)cc1)C(=O)N1CCC[C@H]1c1nc(C2CC2)no1] | QY-4-88 | 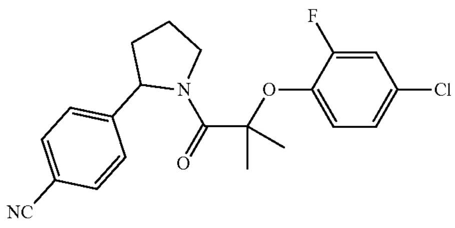 [SMILES: CC(C)(Oc1ccc(Cl)cc1F)C(=O)N1CCCC1c1ccc(C#N)cc1] |

-continued
| Compound nunber | Chemical structure | Compound nunber | Chemical structure |
| --- | --- | --- | --- |
| QY-2-103 | 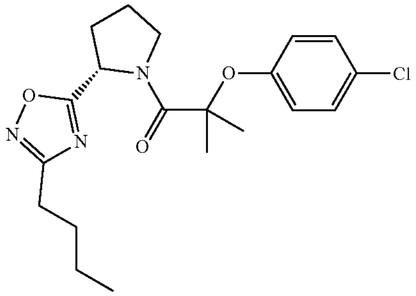 [SMILES: CCCCc1noc([C@@H]2CCCN2C(=O)C(C)(C)Oc2ccc(Cl)cc2)n1] | QY-4-96 | 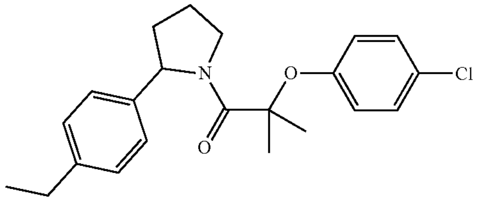 [SMILES: CCc1ccc(C2CCCN2C(=O)C(C)(C)Oc2ccc(Cl)cc2)cc1] |
| QY-2-104 | 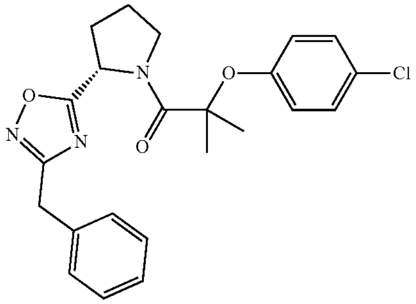 [SMILES: CC(C)(Oc1ccc(Cl)cc1)C(=O)N1CCC[C@H]1c1nc(Cc2ccccc2)no1] | QY-4-99 | 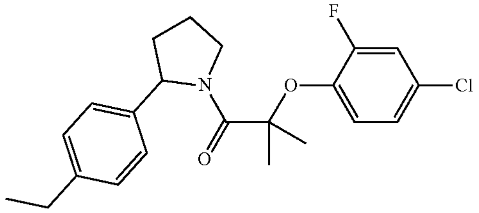 [SMILES: CCc1ccc(C2CCCN2C(=O)C(C)(C)Oc2ccc(Cl)cc2F)cc1] |
| QY-3-4 | 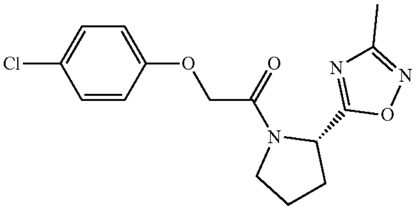 [SMILES: Cc1noc([C@@H]2CCCN2C(=O)COc2ccc(Cl)cc2)n1] | QY-5-1 | 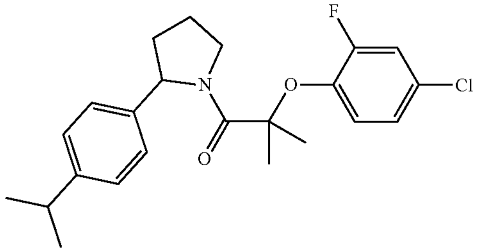 [SMILES: CC(C)c1ccc(C2CCCN2C(=O)C(C)(C)Oc2ccc(Cl)cc2F)cc1] |
| QY-3-11 | 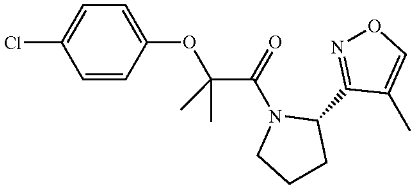 [SMILES: Cc1conc1[C@@H]1CCCN1C(=O)C(C)(C)Oc1ccc(Cl)cc1] | QY-5-4 | 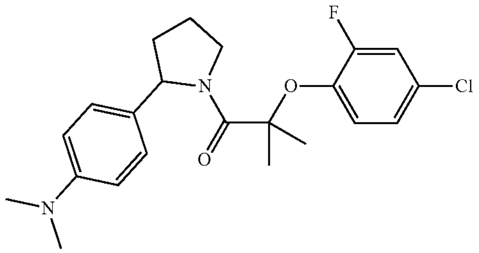 [SMILES: CN(C)c1ccc(C2CCCN2C(=O)C(C)(C)Oc2ccc(Cl)cc2F)cc1] |
| QY-3-17 | 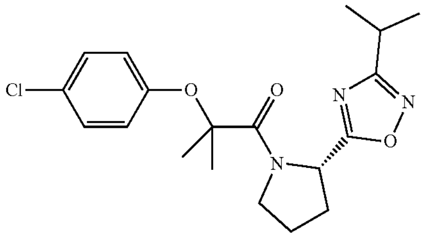 [SMILES: CC(C)c1noc([C@@H]2CCCN2C(=O)C(C)(C)Oc2ccc(Cl)cc2)n1] | QY-5-21 | 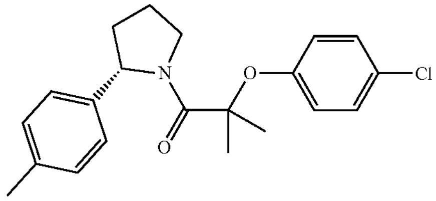 [SMILES: Cc1ccc([C@@H]2CCCN2C(=O)C(C)(C)Oc2ccc(Cl)cc2)cc1] |

-continued
| Compound nunber | Chemical structure | Compound nunber | Chemical structure |
|---|---|---|---|
| QY-3-26 | 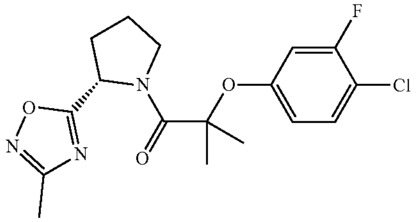 [SMILES: Cc1noc([C@@H]2CCCN2C(=O)C(C)(C)Oc2ccc(Cl)c(F)c2)n1] | QY-5-22 | 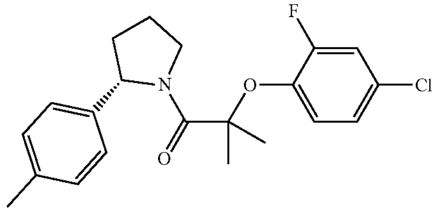 |
| QY-3-27 | 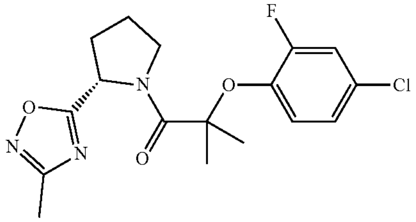 [SMILES: Cc1noc([C@@H]2CCCN2C(=O)C(C)(C)Oc2ccc(Cl)cc2F)n1] | QY-5-79 | 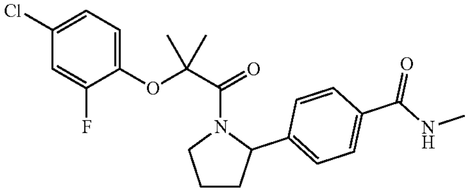 [SMILES: CNC(=O)c1ccc(C2CCCN2C(=O)C(C)(C)Oc2ccc(Cl)cc2F)cc1] |
| QY-3-28 | 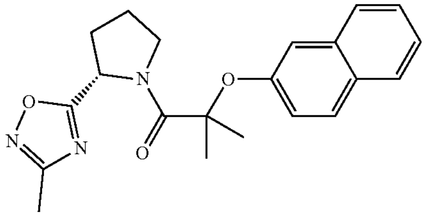 [SMILES: Cc1noc([C@@H]2CCCN2C(=O)C(C)(C)Oc2ccc3ccccc3c2)n1] | QY-5-83 | 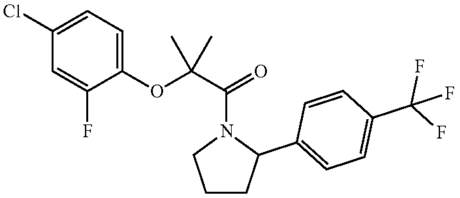 [SMILES: CC(C)(Oc1ccc(Cl)cc1F)C(=O)N1CCCC1c1ccc(C(F)(F)F)cc1] |
| QY-3-29 | 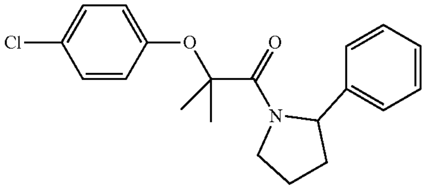 [SMILES: CC(C)(Oc1ccc(Cl)cc1)C(=O)N1CCCC1c1ccccc1] | QY-5-85 | 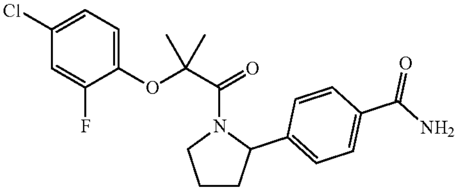 [SMILES: CC(C)(Oc1ccc(Cl)cc1F)C(=O)N1CCCC1c1ccc(C(N)=O)cc1] |
| QY-3-35 | 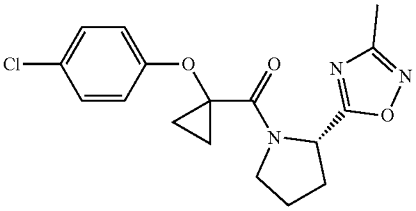 [SMILES: Cc1noc([C@@H]2CCCN2C(=O)C2(Oc3ccc(Cl)cc3)CC2)n1] | QY-6-47 | 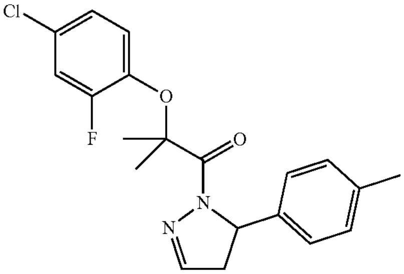 [SMILES: Cc1ccc(C2CC=NN2C(=O)C(C)(C)Oc2ccc(Cl)cc2F)cc1] |
| QY-3-36 | 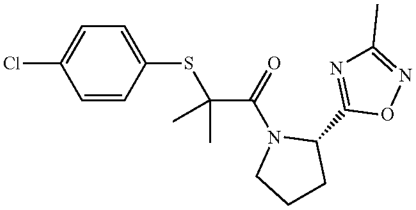 [SMILES: Cc1noc([C@@H]2CCCN2C(=O)C(C)(C)Sc2ccc(Cl)cc2)n1] | QY-6-60 | 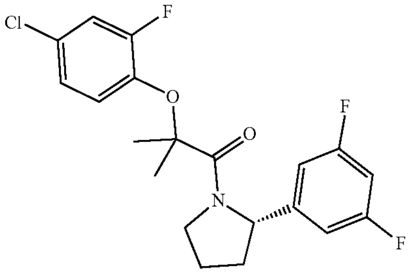 [SMILES: CC(C)(Oc1ccc(Cl)cc1F)C(=O)N1CCC[C@H]1c1cc(F)cc(F)c1] |

-continued
| Compound nunber | Chemical structure | Compound nunber | Chemical structure |
|---|---|---|---|
| QY-3-39 | 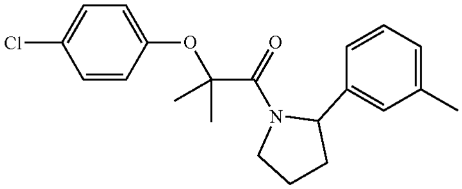 [SMILES: Cc1cccc(C2CCCN2C(=O)C(C)(C)Oc2ccc(Cl)cc2)c1] | QY-6-61 | 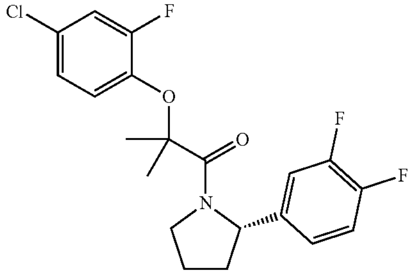 [SMILES: CC(C)(Oc1ccc(Cl)cc1F)C(=O)N1CCC[C@H]1c1ccc(F)c(F)c1] |
| QY-3-46 | 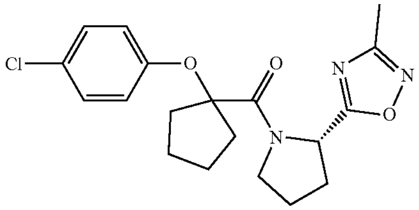 [SMILES: Cc1noc([C@@H]2CCCN2C(=O)C2(Oc3ccc(Cl)cc3)CCCC2)n1] | QY-6-62 | 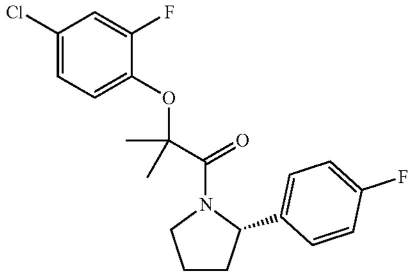 [SMILES: CC(C)(Oc1ccc(Cl)cc1F)C(=O)N1CCC[C@H]1c1ccc(F)cc1] |
| QY-3-51 | 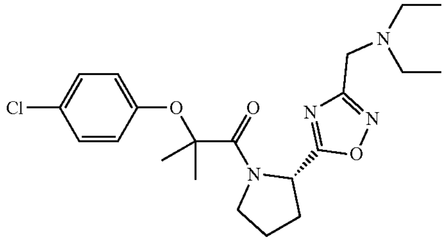 [SMILES: CCN(CC)Cc1noc([C@@H]2CCCN2C(=O)C(C)(C)Oc2ccc(Cl)cc2)n1] | QY-6-63 | 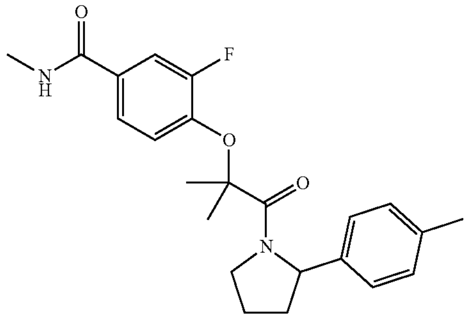 |
| QY-3-65 | 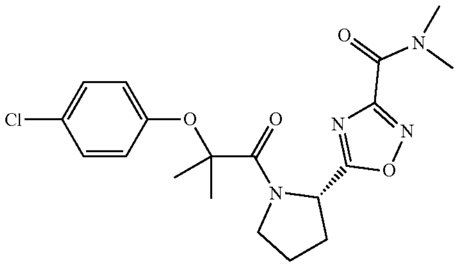 [SMILES: CN(C)C(=O)c1noc([C@@H]2CCCN2C(=O)C(C)(C)Oc2ccc(Cl)cc2)n1] | QY-6-83 | 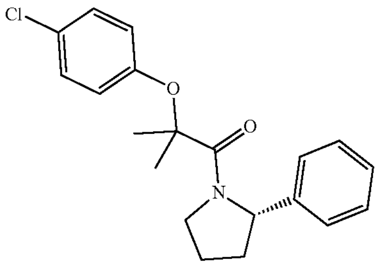 [SMILES: CC(C)(Oc1ccc(Cl)cc1)C(=O)N1CCC[C@H]1c1ccccc1] |
| QY-3-81 | 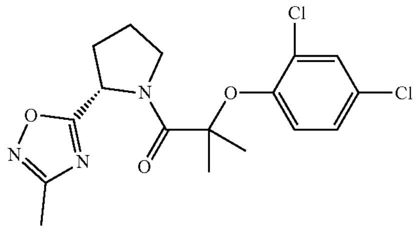 [SMILES: Cc1noc([C@@H]2CCCN2C(=O)C(C)(C)Oc2ccc(Cl)cc2Cl)n1] | QY-6-84 | 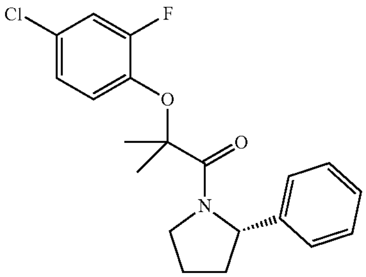 [SMILES: CC(C)(Oc1ccc(Cl)cc1F)C(=O)N1CCC[C@H]1c1ccccc1] |

-continued
| Compound nunber | Chemical structure | Compound nunber | Chemical structure |
|---|---|---|---|
| QY-3-86 | 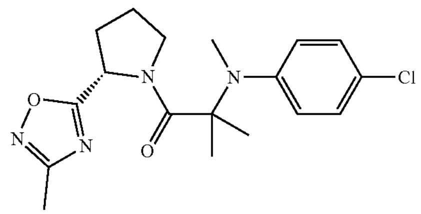 [SMILES: Cc1noc([C@@H]2CCCN2C(=O)C(C)(C)N(C)c2ccc(Cl)cc2)n1] | QY-7-7 | 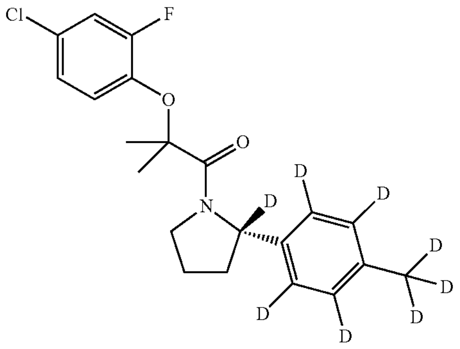 [SMILES: [2H]c1c([2H])c([C@]2([2H])CCCN2C(=O)C(C)(C)Oc2ccc(Cl)cc2F)c([2H])c([2H])c1C([2H])([2H])[2H]] |
| QY-3-94 | 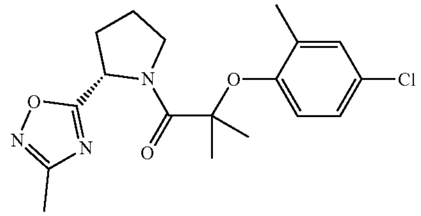 [SMILES: Cc1noc([C@@H]2CCCN2C(=O)C(C)(C)Oc2ccc(Cl)cc2C)n1] | QY-7-50 | 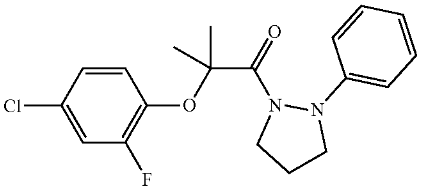 [SMILES: CC(C)(Oc1ccc(Cl)cc1F)C(=O)N1CCCN1c1ccccc1] |
| QY-3-95 | 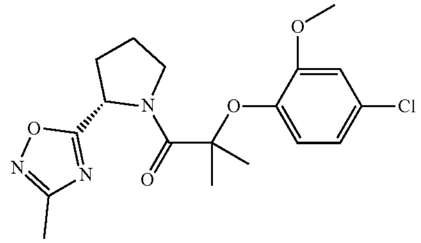 [SMILES: COc1cc(Cl)ccc1OC(C)(C)C(=O)N1CCC[C@H]1c1nc(C)no1] | QY-7-60 | 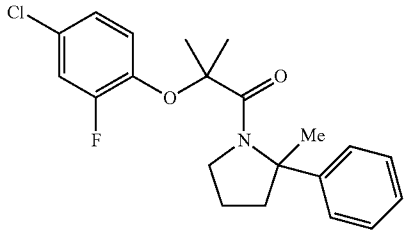 [SMILES: CC(C)(Oc1ccc(Cl)cc1F)C(=O)N1CCCC1(C)c1ccccc1] |
| QY-3-96 | 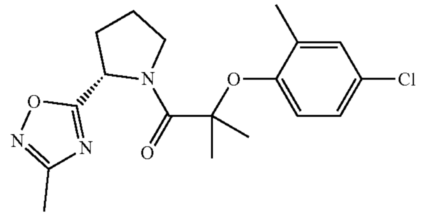 | QY-7-62 | 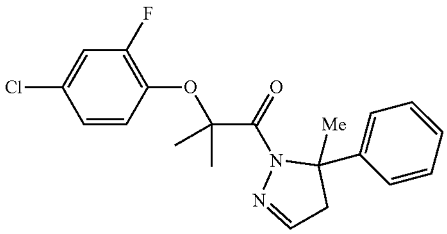 [SMILES: CC(C)(Oc1ccc(Cl)cc1F)C(=O)N1N=CCC1(C)c1ccccc1] |
| QY-3-99 | 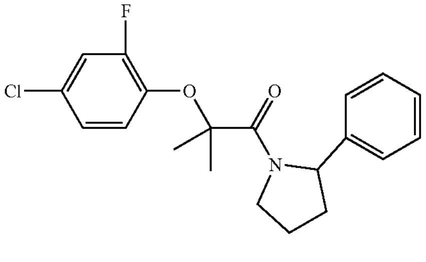 [SMILES: CC(C)(Oc1ccc(Cl)cc1F)C(=O)N1CCCC1c1ccccc1] | XHJ-3-22 | 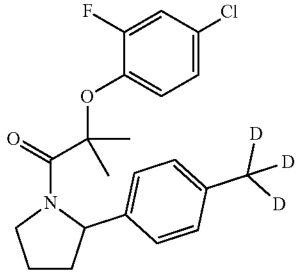 [SMILES: [2H]C([2H])([2H])c1ccc(C2CCCN2C(=O)C(C)(C)Oc2ccc(Cl)cc2F)cc1] |

-continued
| Compound number | Chemical structure | Compound number | Chemical structure |
|---|---|---|---|
| QY4-1 | 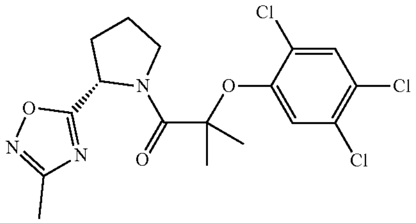 [SMILES: Cc1noc([C@@H]2CCCN2C(=O)C(C)(C)Oc2cc(Cl)c(Cl)cc2Cl)n1] | ZSQ-13-56 | 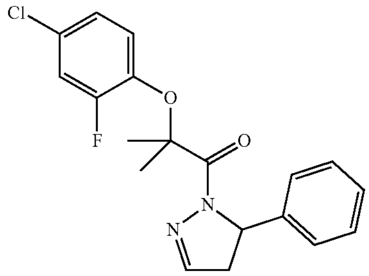 [SMILES: CC(C)(Oc1ccc(Cl)cc1F)C(=O)N1N=CCC1c1ccccc1] |
| QY4-2 | 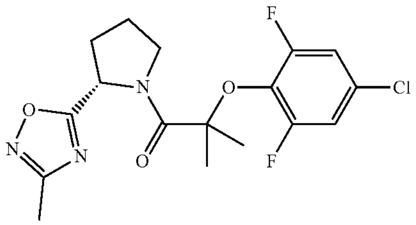 [SMILES: Cc1noc([C@@H]2CCCN2C(=O)C(C)(C)Oc2c(F)cc(Cl)cc2F)n1] | ZSQ-13-57 | 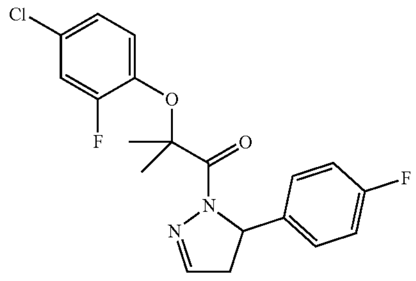 [SMILES: CC(C)(Oc1ccc(Cl)cc1F)C(=O)N1N=CCC1c1ccc(F)cc1] |
| QY-7-101 | 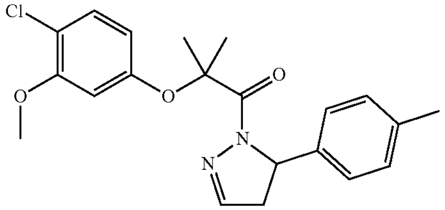 [SMILES: COc1cc(OC(C)(C)C(=O)N2N=CCC2c2ccc(C)cc2)ccc1Cl] | QY-8-101 | 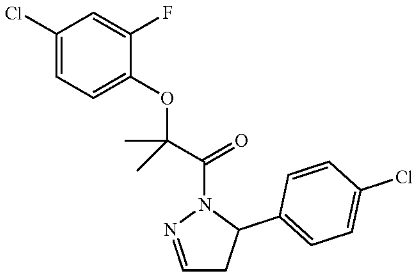 [SMILES: CC(C)(Oc1ccc(Cl)cc1F)C(=O)N1N=CCC1c1ccc(Cl)cc1] |
| QY-9-8 | 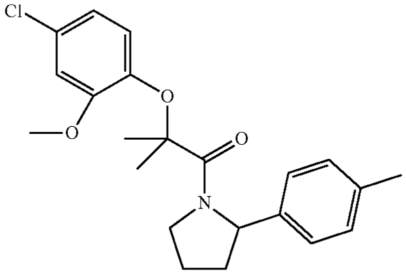 [SMILES: COc1cc(Cl)ccc1OC(C)(C)C(=O)N1CCCC1c1ccc(C)cc1] | QY-9-32 | 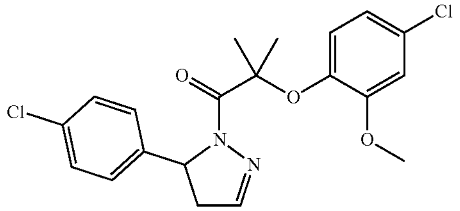 [SMILES: COc1cc(Cl)ccc1OC(C)(C)C(=O)N1N=CCC1c1ccc(Cl)cc1] |
| QY-9-43 | 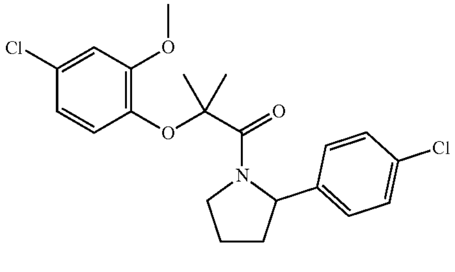 | QY-10-1 | 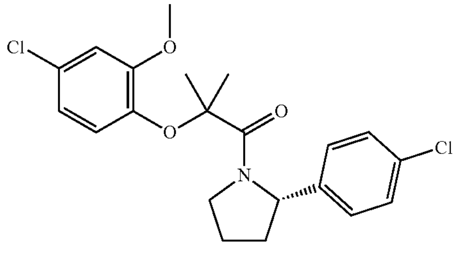 [SMILES: COc1cc(Cl)ccc1OC(C)(C)C(=O)N1CCC[C@H]1c1ccc(Cl)cc1] |

-continued
| Compound number | Chemical structure | Compound number | Chemical structure |
|---|---|---|---|
| QY-10-92 | 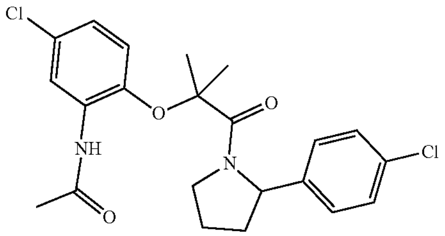 [SMILES: CC(=O)Nc1cc(Cl)ccc1OC(C)(C)C(=O)N1CCCC1c1ccc(Cl)cc1] | QY-10-96 | 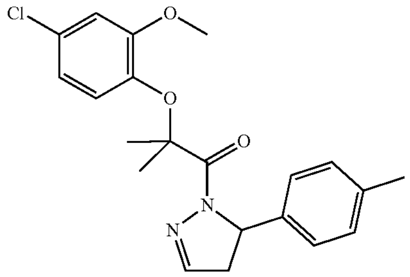 [SMILES: COc1cc(Cl)ccc1OC(C)(C)C(=O)N1N=CCC1c1ccc(C)cc1] |
| QY-10-104 | 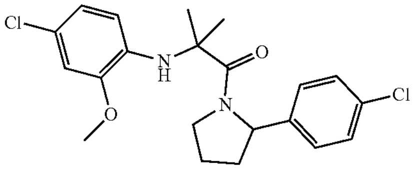 [SMILES: COc1cc(Cl)ccc1NC(C)(C)C(=O)N1CCCC1c1ccc(Cl)cc1] | QY-11-1 | 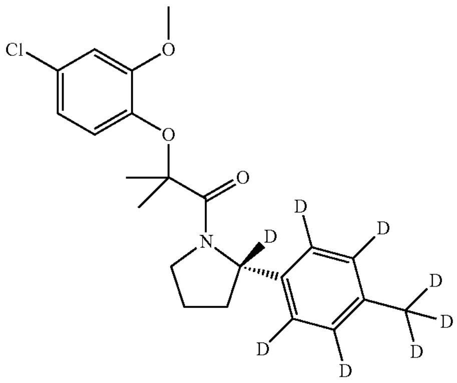 [SMILES: [2H]c1c([2H])c([C@]2([2H])CCCN2C(=O)C(C)(C)Oc2ccc(Cl)cc2OC)c([2H])c([2H])c1C([2H])([2H])[2H]] |
| QY-11-9A | 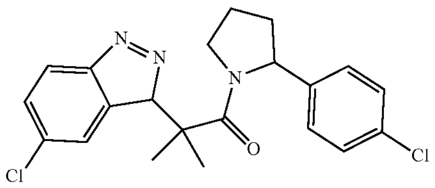 [SMILES: CC(C)(C(=O)N1CCCC1c1ccc(Cl)cc1)C1N=Nc2ccc(Cl)cc21] | QY-11-9B | 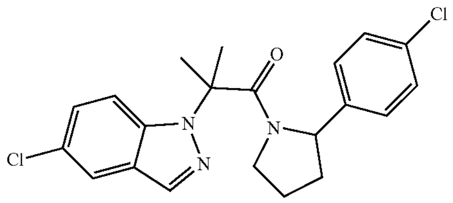 [SMILES: CC(C)(C(=O)N1CCCC1c1ccc(Cl)cc1)n1ncc2cc(Cl)ccc21] |
| QY-11-11A | 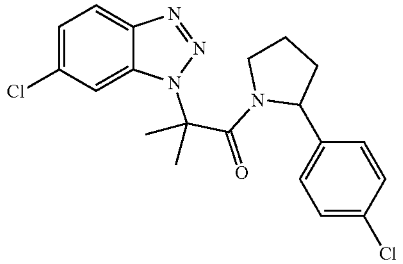 [SMILES: CC(C)(C(=O)N1CCCC1c1ccc(Cl)cc1)n1nnc2ccc(Cl)cc21] | QY-11-11B | 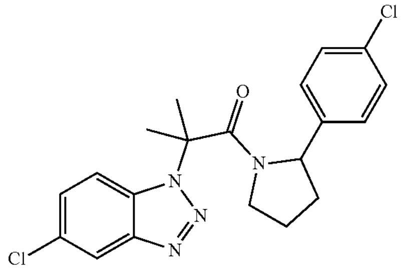 |
| QY-11-15B | 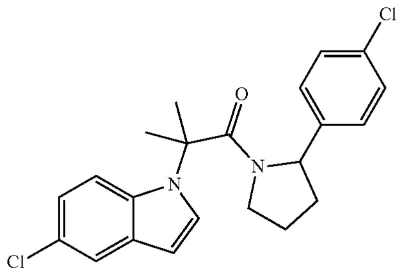 [SMILES: CC(C)(C(=O)N1CCCC1c1ccc(Cl)cc1)n1ccc2cc(Cl)ccc21] | QY-11-16A | 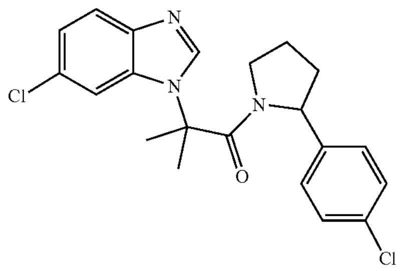 [SMILES: CC(C)(C(=O)N1CCCC1c1ccc(Cl)cc1)n1cnc2ccc(Cl)cc21] |

-continued
| Compound number | Chemical structure | Compound number | Chemical structure |
|---|---|---|---|
| QY-11-16B | 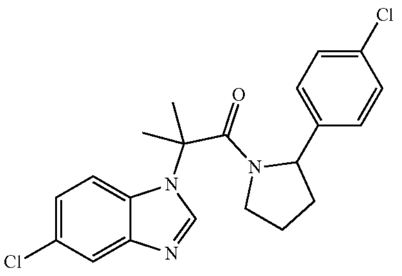 [SMILES: CC(C)(C(=O)N1CCCC1c1ccc(Cl)cc1)n1cnc2cc(Cl)ccc21] | QY-11-36 | 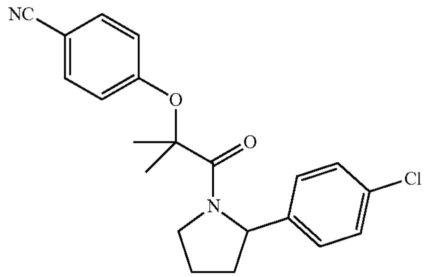 [SMILES: CC(C)(Oc1ccc(C#N)cc1)C(=O)N1CCCC1c1ccc(Cl)cc1] |
| QY-11-44 | 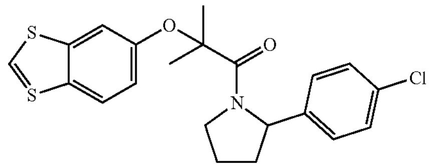 | QY-11-45 | 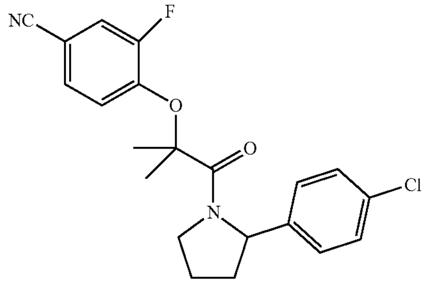 [SMILES: CC(C)(Oc1ccc(C#N)cc1F)C(=O)N1CCCC1c1ccc(Cl)cc1] |
| QY-12-11 | 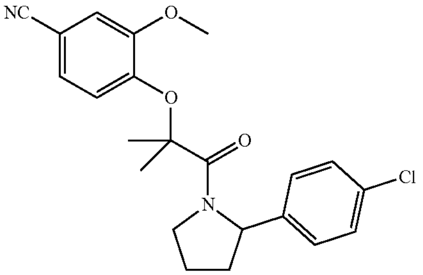 [SMILES: COc1cc(C#N)ccc1OC(C)(C)C(=O)N1CCCC1c1ccc(Cl)cc1] | QY-12-14 | 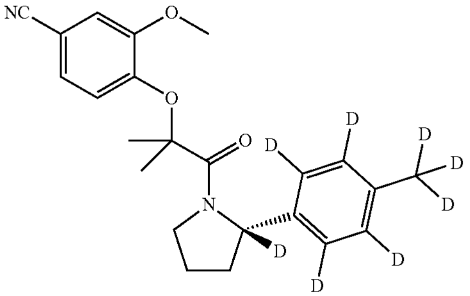 [SMILES: [2H]c1c([2H])c([C@]2([2H])CCCN2C(=O)C(C)(C)Oc2ccc(C#N)cc2OC)c([2H])c([2H])c1C([2H])([2H])[2H]] |
| QY-12-32 | 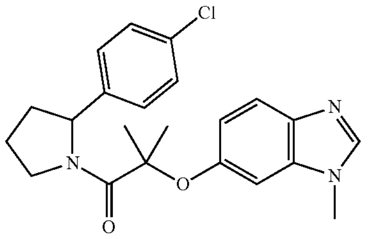 [SMILES: Cn1cnc2ccc(OC(C)(C)C(=O)N3CCCC3c3ccc(Cl)cc3)cc21] | QY-13-42 | 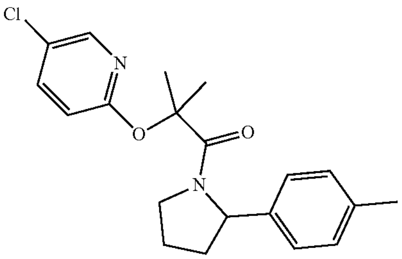 [SMILES: Cc1ccc(C2CCCN2C(=O)C(C)(C)Oc2ccc(Cl)cn2)cc1] |
| QY-13-68 | 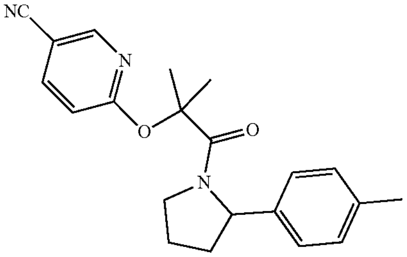 [SMILES: Cc1ccc(C2CCCN2C(=O)C(C)(C)Oc2ccc(C#N)cn2)cc1] | QY-13-70 | 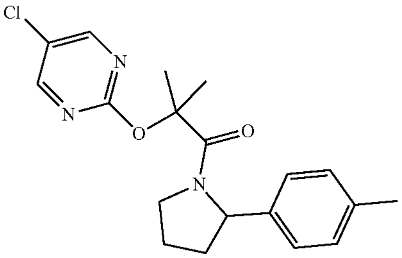 [SMILES: Cc1ccc(C2CCCN2C(=O)C(C)(C)Oc2ncc(Cl)cn2)cc1] |

-continued
| Compound nunber | Chemical structure | Compound nunber | Chemical structure |
| --- | --- | --- | --- |
| QY-13-86 | 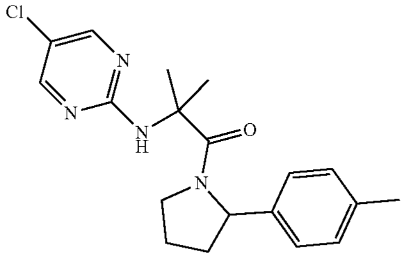 [SMILES: Cc1ccc(C2CCCN2C(=O)C(C)(C)Nc2ncc(Cl)cn2)cc1] | QY-14-8 | 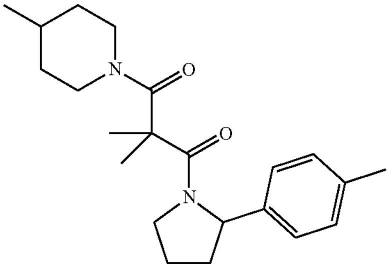 |
| QY-14-9 | 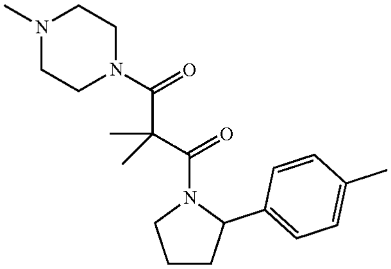 | QY-14-17 | 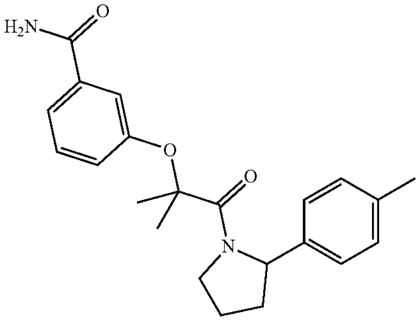 [SMILES: Cc1ccc(C2CCCN2C(=O)C(C)(C)Oc2cccc(C(N)=O)c2)cc1] |
| QY-14-24 | 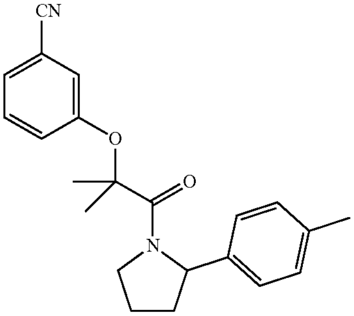 [SMILES: Cc1ccc(C2CCCN2C(=O)C(C)(C)Oc2cccc(C#N)c2)cc1] | QY-14-25 | 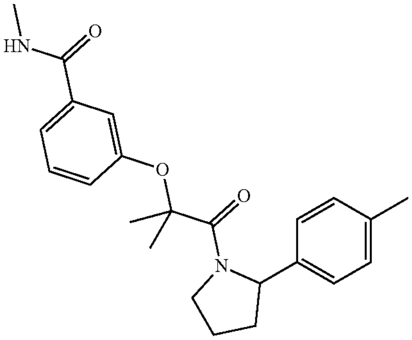 |
| QY-14-27 | 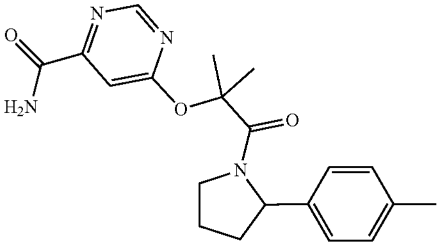 [SMILES: Cc1ccc(C2CCCN2C(=O)C(C)(C)Oc2cc(C(N)=O)ncn2)cc1] | QY-14-29 | 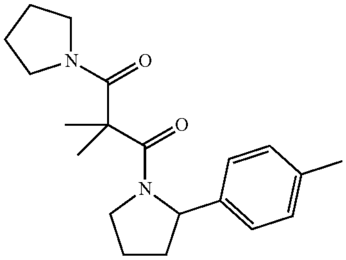 [SMILES: Cc1ccc(C2CCCN2C(=O)C(C)(C)C(=O)N2CCCC2)cc1] |
| QY-14-30 | 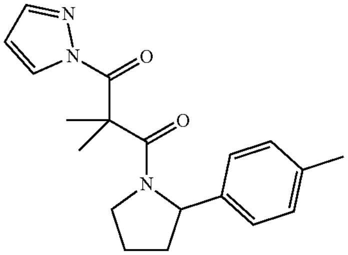 [SMILES: Cc1ccc(C2CCCN2C(=O)C(C)(C)C(=O)n2cccn2)cc1] | QY-14-31 | 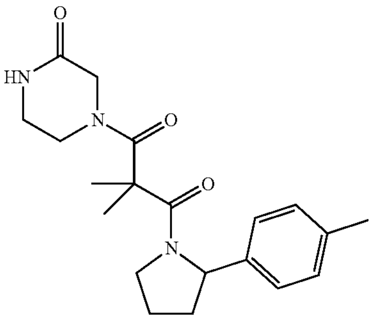 [SMILES: Cc1ccc(C2CCCN2C(=O)C(C)(C)C(=O)N2CCNC(=O)C2)cc1] |

-continued
| Compound nunber | Chemical structure | Compound nunber | Chemical structure |
|---|---|---|---|
| QY-14-33 | 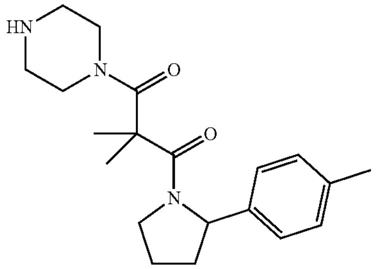 [SMILES: Cc1ccc(C2CCCN2C(=O)C(C)(C)C(=O)N2CCNCC2)cc1] | QY-14-34 | 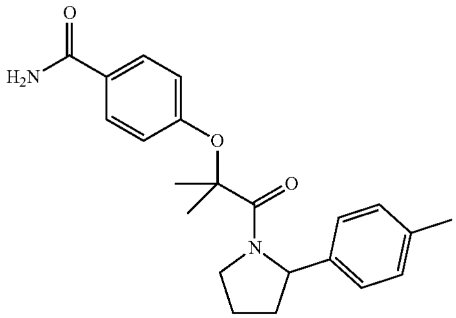 [SMILES: Cc1ccc(C2CCCN2C(=O)C(C)(C)Oc2ccc(C(N)=O)cc2)cc1] |
| QY-14-35 | 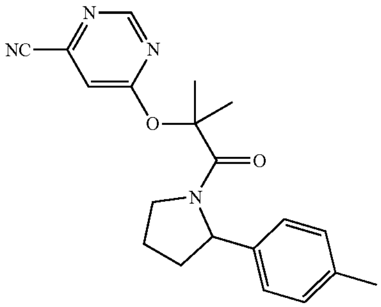 [SMILES: Cc1ccc(C2CCCN2C(=O)C(C)(C)Oc2cc(C#N)ncn2)cc1] | QY-14-40 | 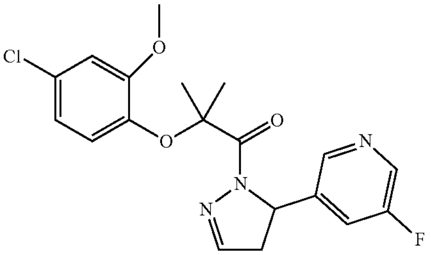 [SMILES: COc1cc(Cl)ccc1OC(C)(C)C(=O)N1N=CCC1c1cncc(F)c1] |
| QY-14-44 | 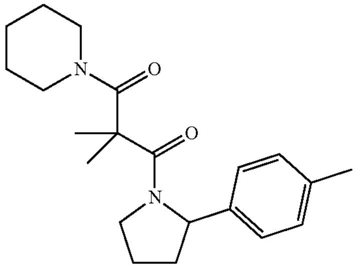 [SMILES: Cc1ccc(C2CCCN2C(=O)C(C)(C)C(=O)N2CCCCC2)cc1] | QY-14-59 | 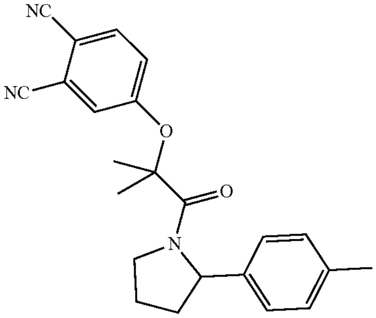 [SMILES: Cc1ccc(C2CCCN2C(=O)C(C)(C)Oc2ccc(C#N)c(C#N)c2)cc1] |
| QY-14-60 | 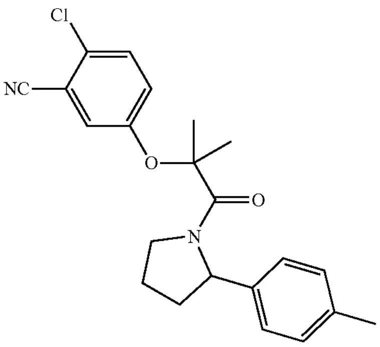 [SMILES: Cc1ccc(C2CCCN2C(=O)C(C)(C)Oc2ccc(Cl)c(C#N)c2)cc1] | QY-14-68 | 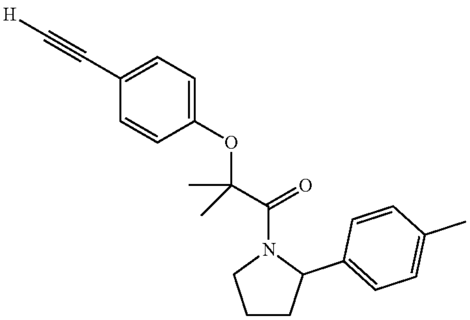 [SMILES: C#Cc1ccc(OC(C)(C)C(=O)N2CCCC2c2ccc(C)cc2)cc1] |

-continued
| Compound nunber | Chemical structure | Compound nunber | Chemical structure |
|---|---|---|---|
| QY-15-11 | 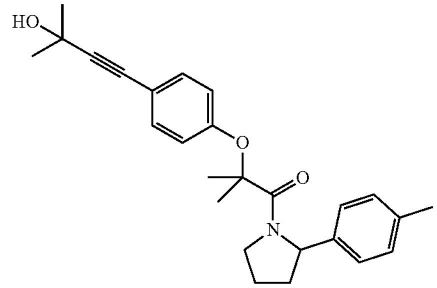 [SMILES: Cc1ccc(C2CCCN2C(=O)C(C)(C)Oc2ccc(C#CC(C)(C)O)cc2)cc1] | QY-15-12 | 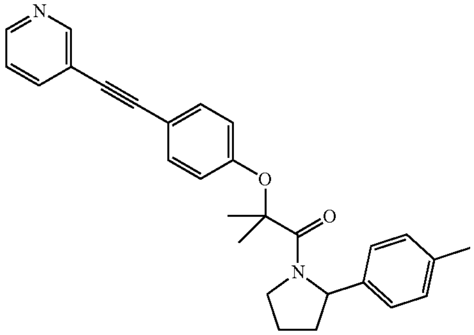 [SMILES: Cc1ccc(C2CCCN2C(=O)C(C)(C)Oc2ccc(C#Cc3cccnc3)cc2)cc1] |
| QY-15-31 | 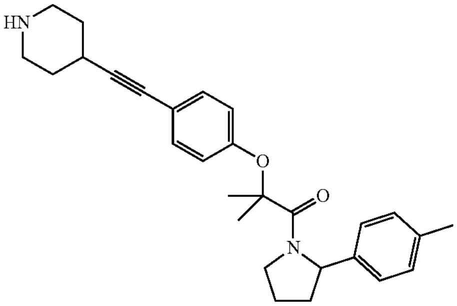 [SMILES: Cc1ccc(C2CCCN2C(=O)C(C)(C)Oc2ccc(C#CC3CCNCC3)cc2)cc1] | QY-16-60 | 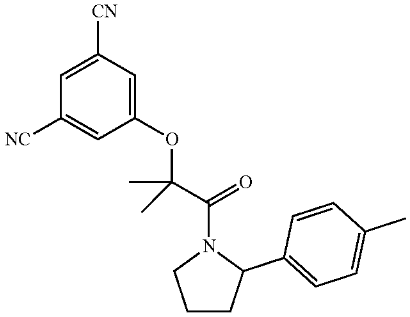 [SMILES: Cc1ccc(C2CCCN2C(=O)C(C)(C)Oc2cc(C#N)cc(C#N)c2)cc1] |
| QY-16-61 | 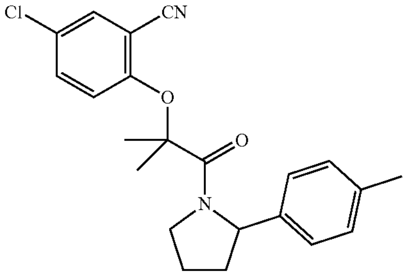 [SMILES: Cc1ccc(C2CCCN2C(=O)C(C)(C)Oc2ccc(Cl)cc2C#N)cc1] | QY-16-66 | 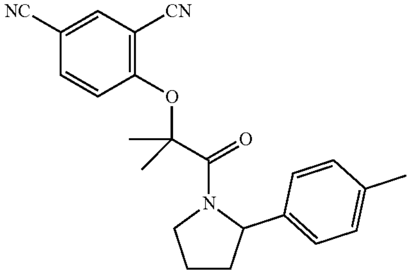 [SMILES: Cc1ccc(C2CCCN2C(=O)C(C)(C)Oc2ccc(C#N)cc2C#N)cc1] |
| QY-16-75 | 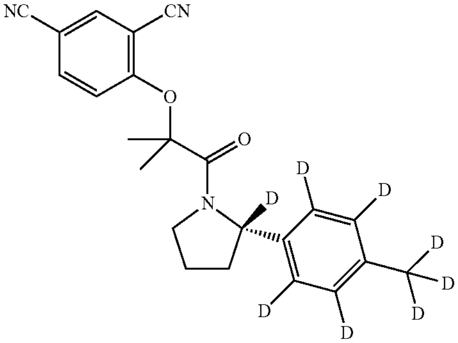 [SMILES: [2H]c1c([2H])c([C@]2([2H])CCCN2C(=O)C(C)(C)Oc2ccc(C#N)cc2C#N)c([2H])c([2H])c1C([2H])([2H])[2H]] | QY-16-76 | 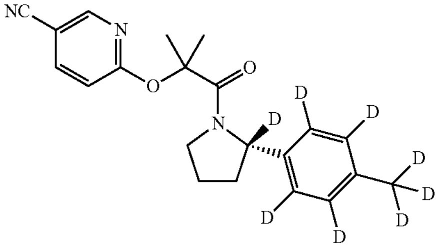 [SMILES: [2H]c1c([2H])c([C@]2([2H])CCCN2C(=O)C(C)(C)Oc2ccc(C#N)cn2)c([2H])c([2H])c1C([2H])([2H])[2H]] |
| QY-16-77 | 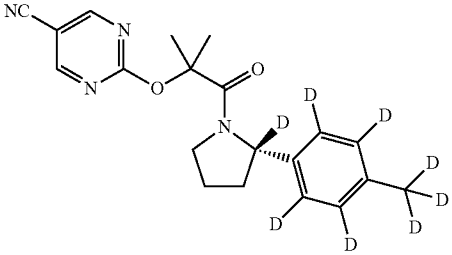 [SMILES: [2H]c1c([2H])c([C@]2([2H])CCCN2C(=O)C(C)(C)Oc2ncc(C#N)cn2)c([2H])c([2H])c1C([2H])([2H])[2H]] | QY-16-82 | 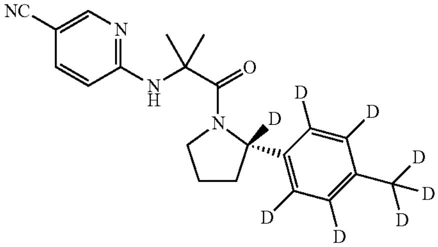 [SMILES: [2H]c1c([2H])c([C@]2([2H])CCCN2C(=O)C(C)(C)Nc2ccc(C#N)cn2)c([2H])c([2H])c1C([2H])([2H])[2H]] |

-continued

| Compound number | Chemical structure | Compound number | Chemical structure |
|---|---|---|---|
| QY-16-84 | 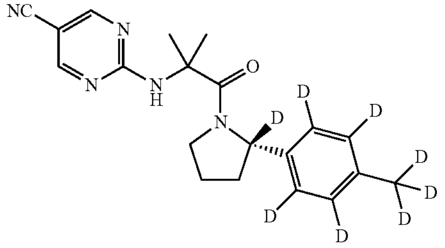 [SMILES: [2H]c1c([2H])c([C@]2([2H])CCCN2C(=O)C(C)(C)Nc2ncc(C#N)cn2)c([2H])c([2H])c1C([2H])([2H])[2H]] | | |

The second aspect of the present invention provides a preparation method of the compound according to the first aspect of the present invention, and the method comprises the steps of:

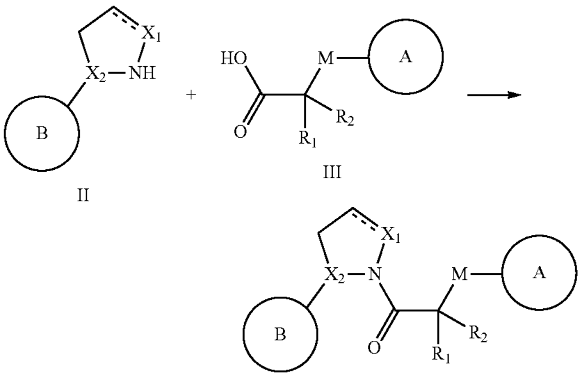

in an inert solvent, a compound of formula II is reacted with a compound of formula III to obtain a compound of formula I.

In another preferred embodiment, the inert solvent is dichloromethane.

In another preferred embodiment, the reaction is carried out in the presence of HATU and DIEA.

The third aspect of the present invention provides a pharmaceutical composition comprising (a) a therapeutically effective amount of the compound according to the first aspect of the present invention, or pharmaceutically acceptable salts, hydrates or solvates thereof; and (b) a pharmaceutically acceptable carrier.

In another preferred embodiment, the diseases or conditions are selected from the group consisting of inflammatory diseases, infectious diseases, ischemic or degenerative-related diseases, and tissue damage.

In another preferred embodiment, the inflammatory, infectious, ischemic or degenerative related diseases are selected from the group consisting of: systemic inflammatory syndrome, acetaminophen-induced liver injury, acute pancreatitis, inflammatory bowel disease, sepsis, *Salmonella* infection, *Listeria* infection, Vaccinia virus infection, Alzheimer's disease, ischemic cardiomyopathy, ischemic stroke, and atherosclerosis.

In another preferred embodiment, the tissue damage includes liver damage, liver toxicity or hepatocyte necrosis.

The fourth aspect of the present invention provides a use of the compound of formula I according to the first aspect of the present invention, for the preparation of a pharmaceutical composition for the treatment or prevention of diseases or conditions related to programmed cell necrosis and/or the activity or expression levels of human receptor interacting protein 1 kinase (RIPK1).

In another preferred embodiment, the RIPK1 kinase is wild type, or RIPK1 S161A.

In another preferred embodiment, the diseases or conditions are selected from the group consisting of inflammatory diseases, infectious diseases, ischemic or degenerative related diseases, and tissue damage.

It should be understood that, within the scope of the present invention, the above technical features of the present invention and the technical features specifically described in the following descriptions (such as the examples) can be combined with each other to form a new or preferred technical solution. Due to space limitations, they will not be repeated herein.

DETAILED DESCRIPTION OF THE INVENTION

Figure 1:
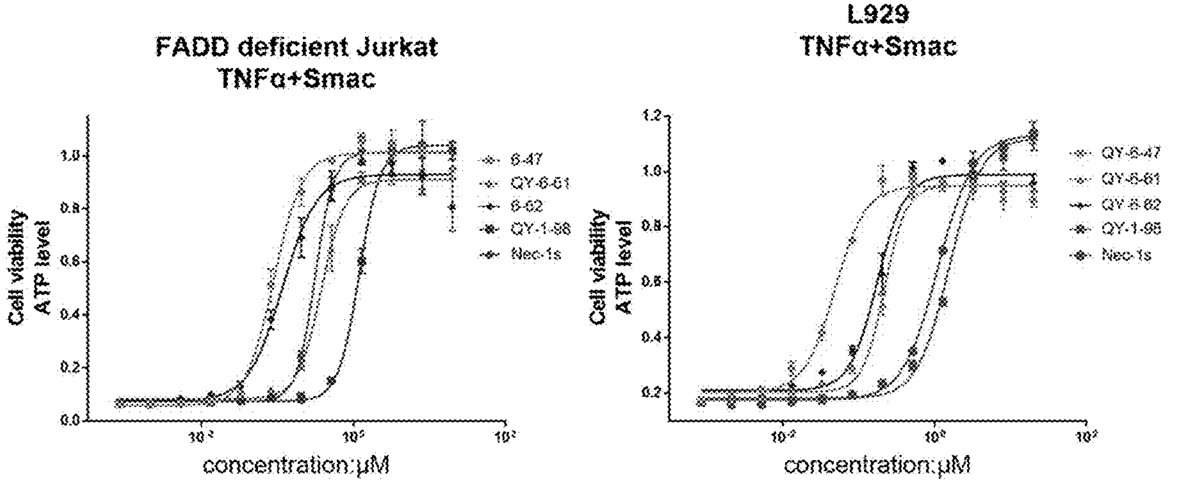
FIG. 1 shows the effect of the compound on TNF-induced programmed cell necrosis in Example 2.

After long-term and in-depth research, a class of inhibitors of programmed cell necrosis with novel structure has been screened out. The inhibitors of programmed cell necrosis have excellent RIPK1 inhibitory activity, and thus can be used to prepare a pharmaceutical composition for preventing and/or treating diseases involving cell death and/or inflammation. The present invention has been completed on this basis.

Terms

Unless otherwise defined, the terms used according to the present invention and herein have the following meanings:

As used herein, the term "C1-C4 alkyl" refers to straight or branched alkyl groups having 1-4 carbon atoms, such as methyl, ethyl, propyl, isopropyl, butyl, isobutyl, tert-butyl, and the like.

As used herein, the term "C3-C8 cycloalkyl" refers to cyclic alkyl groups having 1-8 carbon atoms, such as cyclopropyl, cyclobutyl, cyclopentyl, cyclohexyl, cycloheptyl, and cyclooctyl.

As used herein, the term "C1-C6 alkoxy" refers to C1-C6 alkyl as defined above, which is attached to the remaining moiety of the molecule through oxygen atom. Preferably, the C1-C6 alkoxy may include methoxy, ethoxy and isopropoxy.

As used herein, the term "C1-C6 amino" refers to C1-C6 alkyl as defined above, which is attached to the remaining moiety of the molecule through nitrogen atom. Preferably, the alkylamino may include dimethylamino and diethylamino.

The term "halogen" refers to F, Cl, Br and I.

The term "haloalkyl" refers to a C1-C3 alkyl substituted by halogen. Preferably, haloalkyl is trifluoromethyl, difluoromethyl, trifluoromethoxy. The "C1-C3 alkyl" refers to straight or branched alkyl having 1 to 3 carbon atoms, such as methyl, ethyl, n-propyl and isopropyl.

The term "aryl" refers to C6-C18 aromatic groups such as phenyl or naphthyl, unsubstituted or substituted aryl which is substituted by one or more (e.g., 2, 3, 4 or 5) atoms or groups selected from halogen, nitro, hydroxyl, amino, cyano, haloalkyl, substituted or unsubstituted C1-C6 alkyl, substituted or unsubstituted C3-C8 cycloalkyl, substituted or unsubstituted C1-C6 alkoxy, substituted or unsubstituted C1-C6 alkylamino, substituted or unsubstituted C1-C6 carboxyl, substituted or unsubstituted C1-C6 ester, substituted or unsubstituted C2-C6 alkanoyl, and substituted or unsubstituted C2-C6 alkamido.

The term "heteroaryl" refers to 5-12 membered aromatic groups containing one or more heteroatoms selected from nitrogen, oxygen and sulfur. Heteroaryl can include pyridine, pyrazine, pyrimidine, thiophene, furan, isoxazole, isothiazole, pyrazole, imidazole. Such groups may be unsubstituted, substituted by one or more (e.g., 2, 3, 4 or 5) atoms or groups selected from halogen, nitro, hydroxy, amino, cyano, haloalkyl, substituted or unsubstituted C1-C6 alkyl, substituted or unsubstituted C3-C8 cycloalkyl, substituted or unsubstituted C1-C6 alkoxy, substituted or unsubstituted C1-C6 alkylamino, substituted or unsubstituted C1-C6 carboxyl, substituted or unsubstituted C1-C6 ester, substituted or unsubstituted C2-C6 alkanoyl, and substituted or unsubstituted C2-C6 alkamido.

The term "heterocycle" or "heterocyclyl" refers to 5-12 membered non-aromatic groups (including saturated, partially saturated or unsaturated groups) comprising one or more heteroatoms selected from nitrogen, oxygen and sulfur and having monocyclic ring or fused ring (including bridged ring systems and spiro ring systems). In fused ring system, one or more of rings may be cycloalkyl, aryl, or heteroaryl. In one embodiment, nitrogen and/or sulfur atoms of heterocyclyl are optionally oxidized to provide N-oxide, sulfinyl and sulfonyl moieties. Examples of "heterocyclyl" and fused analogs thereof include pyrrolidinyl, piperidinyl, piperazinyl, imidazolidinyl, 2,3-dihydrofuran (2,3-b) pyridyl, benzoxazinyl, tetrahydroquinolinyl, tetrahydroisoquinolinyl, indolinyl, etc. The term also includes non-aromatic partially unsaturated monocyclic rings such as 2- or 4-pyridone attached through a nitrogen atom or N-substituted-(1H,3H)-pyrimidine-2,4-diones (N-substituted uracils).

In the present invention, the terms "comprise", "contain" or "include" mean that the various ingredients can be used together in the mixture or composition of the present invention. Thus, the terms "consisting essentially of" and "consisting of" are encompassed by the term "comprise".

In the present invention, the term "pharmaceutically acceptable" ingredient refers to substances that are suitable for use in humans and/or animals without excessive adverse side effects (such as toxicity, irritation and allergy), i.e., have a reasonable benefit/risk ratio.

In the present invention, the term "effective amount" refers to amount that treats, alleviates or prevents a target disease or condition, or amount that exhibits detectable therapeutic or prophylactic effect for a therapeutic agent. The precise effective amount for a subject depends on the size and health condition of the subject, the nature and extent of the condition, and the therapeutic agent and/or combination of therapeutic agents selected for administration. Therefore, it is useless to prespecify the exact effective amount. However, for a given situation, routine experimentation can be used to determine the effective amount, which can be judged by the clinician.

As used herein, the term "pharmaceutically acceptable salts" refers to salts suitable for use as a medicament formed by the compound of the present invention with acids or bases. Pharmaceutically acceptable salts include inorganic salts and organic salts. A preferred class of salts is the salts formed by the compound of the present invention with acids. Acids suitable for forming salts include, but are not limited to, inorganic acids such as hydrochloric acid, hydrobromic acid, hydrofluoric acid, sulfuric acid, nitric acid, phosphoric acid; organic acids such as formic acid, acetic acid, propionic acid, oxalic acid, malonic acid, succinic acid, fumaric acid, maleic acid, lactic acid, malic acid, tartaric acid, citric acid, picric acid, methanesulfonic acid, benzenemethanesulfonic acid, and benzenesulfonic acid; and acidic amino acids such as aspartic acid and glutamic acid.

Some of the compounds of the present invention may be crystallized or recrystallized from water or various organic solvents, in which case various solvates may be formed. Solvates of the present invention include stoichiometric solvates such as hydrates and the like, as well as compounds containing variable amounts of water formed when prepared by lyophylization.

The term "prodrug" as used herein refers to any compound that, when administered to a biological system, produces a "drug" substance (biologically active compound) as a result of one or more spontaneous chemical reactions, one or more enzymatic chemical reactions, and/or one or more metabolic chemical reactions. It also includes biodegradable polymer derivatives of the compound of the invention, e.g., as described in Int. J. Pharm. 115, 61-67 (1995).

The present invention also includes all suitable isotopic variations of the compound of the present invention. Isotopic variants of the compound of the present invention are defined as those in which at least one atom is replaced by an atom having the same atomic number but different atomic mass from that commonly found in nature. Examples of isotopes that may be incorporated into the compound of the present invention include isotopes of hydrogen, carbon, nitrogen, oxygen, phosphorus, sulfur, fluorine, and chlorine, such as $^2H$, $^3H$, $^{11}C$, $^{13}C$, $^{14}C$, $^{15}N$, $^{17}O$, $^{18}O$, $^{35}S$, $^{18}F$, and $^{36}Cl$ respectively. Some isotopic variants of the present invention, e.g., those into which radioactive isotopes (eg, $^3H$ or $^{14}C$) are incorporated, are used in drug and/or substrate tissue distribution studies. Tritiated (ie, $^3H$) and carbon-14 (ie, $^{14}C$) isotopes are particularly preferred because of their ease of preparation and detection. In addition, substitution with isotopes (eg, deuterium, ie, $^2H$) may provide some therapeutic advantages resulting from increased metabolic stability, e.g., increased in vivo half-life or reduced dosage requirements and may therefore be preferred in some cases. Isotopic variants of the compound of the present invention can generally be prepared by routine procedures, eg, by using the appropriate reagents for the appropriate isotopic variant, by the exemplified methods or as described in the experimental section below.

Compounds of Formula I and Preparation Therefor

The present invention provides a compound represented by the following formula (I), or pharmaceutically acceptable salt thereof,

I

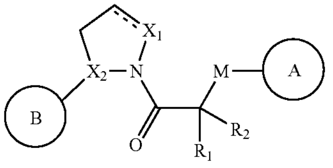

wherein:

dashed line is a chemical bond or none;

M is selected from the group consisting of S, O and NH;

$X_1$ is selected from the group consisting of $CR_2$, NR, O, S, CR, and N;

$X_2$ is selected from the group consisting of CR, and N;

R is selected from the group consisting of H, D, and C1-C4 alkyl;

$R_1$ and $R_2$ are each independently selected from the the group consisting of H, and C1-C4 alkyl; or $R_1$ and $R_2$ together form a structure of substituted or unsubstituted $-(CH_2)_n-$ s; wherein, n is 1, 2, 3 or 4;

ring A is selected from the group consisting of substituted or unsubstituted C6-C10 aryl, and substituted or unsubstituted 5-12 membered heteroaryl;

ring B is selected from the group consisting of substituted or unsubstituted C6-C10 aryl, and substituted or unsubstituted 5-12 membered heteroaryl;

wherein, the substituted means that the hydrogen atoms on the group are substituted by one or more (such as 2, 3, 4, etc.) substituents selected from the group consisting of halogen, deuterium, C1-C6 alkoxy, halogenated C1-C6 alkoxy, methyl sulfonyl, $-S(=O)_2NH_2$, oxo (=O), —CN, hydroxyl, $-NH_2$, carboxyl, C2-C6 amido($-C(=O)-N(Rc)_2$ or —NH—C(=O)(Rc), Rc is H or C1-C5 alkyl), C1-C6 alkyl-(C2-C6 amido), and substituted or unsubstituted groups selected from the group consisting of C1-C6 alkyl, C3-C8 cycloalkyl, C1-C6 amino, C6-C10 aryl, 5-10 membered heteroaryl having 1-3 heteroatoms selected from N, S and O, 5-12 membered heterocyclyl having 1-3 heteroatoms selected from N, S and O, $-(CH_2)-$C6-C10 aryl, and $-(CH_2)$-(5-10 membered heteroaryl having 1-3 heteroatoms selected from N, S and O), and the substituents are selected from the group consisting of halogen, C1-C6 alkyl, C1-C6 alkoxy, oxo, —CN, $-NH_2$, —OH, C6-C10 aryl, C1-C6 amino, C2-C6 amido, and 5-10 membered heteroaryl having 1-3 heteroatoms selected from N, S and O.

Preferred compounds are shown in Table 1 of the Example.

The compound of the present invention can be prepared by the following method:

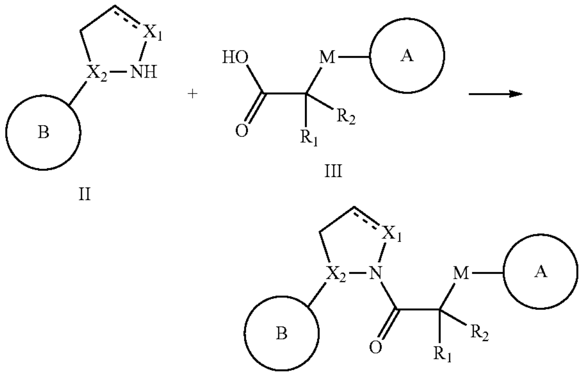

II III I in an inert solvent, a compound of formula II is reacted with a compound of formula III to obtain a compound of formula I.

In another preferred embodiment, the inert solvent is dichloromethane.

In another preferred embodiment, the reaction is carried out in the presence of HATU and DIEA.

Pharmaceutical Composition and the Administration Thereof

Since the compound herein has excellent activating activity for RIPK1, the compound of the present invention and various crystal forms, pharmaceutically acceptable inorganic or organic salts, hydrates or solvates thereof, and pharmaceutical compositions containing the compound according to the present invention as main active ingredient can be used to prevent and/or treat diseases caused by hepatitis B virus. According to the prior art, the compound of the present invention can be used to treat the following diseases: inflammatory diseases, infectious diseases, ischemic or degenerative related diseases, and tissue damage.

The pharmaceutical composition of the invention comprises the compound of the present invention or pharmaceutically acceptable salts thereof and pharmaceutically acceptable excipients or carriers in a safe and effective amount range. Wherein the "safe and effective amount" means that the amount of compound is sufficient to significantly ameliorate the condition without causing significant side effects. Generally, the pharmaceutical composition contains 0.1-1000 mg compound of the invention per dose, preferably, 0.5-500 mg compound of the invention per dose. Preferably, the "dose" is a capsule or tablet.

"Pharmaceutically acceptable carrier" means one or more compatible solid or liquid fillers, or gelatinous materials which are suitable for human use and should be of sufficient purity and sufficiently low toxicity. "Compatibility" herein means that each component in the composition can be admixed with the compound of the present invention and with each other without significantly reducing the efficacy of the compounds. Some examples of pharmaceutically acceptable carriers include cellulose and the derivatives thereof (such as sodium carboxymethyl cellulose, sodium ethyl cellulose, and cellulose acetate, etc.), gelatin, talc, solid lubricants (such as stearic acid, and magnesium stearate), calcium sulfate, vegetable oils (such as soybean oil, sesame oil, peanut oil, and olive oil, etc.), polyols (such as propylene glycol, glycerol, mannitol, and sorbitol, etc.), emulsifiers (such as Tween®), wetting agent (such as sodium dodecyl sulfate), coloring agents, flavoring agents, stabilizers, anti-oxidants, preservatives, and pyrogen-free water, etc.

There is no special limitation of administration mode for the compound or pharmaceutical composition of the present invention, and the representative administration mode includes (but is not limited to) oral, rectal, parenteral (intravenous, intramuscular or subcutaneous), and topical administration. A particularly preferred mode of administration is oral.

Solid dosage forms for oral administration include capsules, tablets, pills, powders and granules. In these solid dosage forms, the active compounds are mixed with at least one conventional inert excipient (or carrier), such as sodium citrate or dicalcium phosphate or mixed with any of the following components: (a) fillers or compatibilizer, such as starch, lactose, sucrose, glucose, mannitol and silicic acid; (b) binders, such as hydroxymethyl cellulose, alginates, gelatin, polyvinylpyrrolidone, sucrose and arabic gum; (c) humectant, such as glycerol; (d) disintegrating agents such as agar, calcium carbonate, potato starch or tapioca starch, alginic acid, certain composite silicates, and sodium carbonate; (e) dissolution-retarding agents such as paraffin; (f) absorption accelerators, such as quaternary ammonium compounds; (g) wetting agents such as cetyl alcohol and glyceryl monostearate; (h) adsorbents, such as kaolin; and (i) lubricants such as talc, stearin calcium, magnesium stearate, solid polyethylene glycol, sodium lauryl sulfate, or the mixtures thereof. In capsules, tablets and pills, the dosage forms may also contain buffering agents.

The solid dosage forms such as tablets, sugar pills, capsules, pills and granules can be prepared with coatings and shells, such as enteric coatings and any other materials known in the art. They can contain opaque agent. The active compound or compound in the composition can be released in a delayed mode in a given portion of the digestive tract. Examples of the embedding component that can be used include polymers and waxes. If necessary, the active compound and one or more above excipients can form microcapsules.

Liquid dosage forms for oral administration include pharmaceutically acceptable emulsions, solutions, suspensions, syrups or tinctures. In addition to the active compounds, the liquid dosage forms may contain any conventional inert diluents known in the art such as water or other solvents, solubilizers and emulsifiers, such as ethanol, isopropanol, ethyl carbonate, ethyl acetate, propylene glycol, 1,3-butanediol, dimethyl formamide, as well as oil, in particular, cottonseed oil, peanut oil, corn germ oil, olive oil, castor oil and sesame oil, or the combinations thereof.

In addition to these inert diluents, the composition may also contain additives such as wetting agents, emulsifiers, and suspending agents, sweeteners, flavoring agents and perfume.

In addition to the active compounds, the suspension may contain suspending agent, such as ethoxylated isooctadecanol, polyoxyethylene sorbitol and sorbitan esters, microcrystalline cellulose, methanol aluminum and agar, or the combinations thereof.

The compositions for parenteral injection may comprise physiologically acceptable sterile aqueous or anhydrous solutions, dispersions, suspensions or emulsions, and sterile powders which can be re-dissolved into sterile injectable solutions or dispersions. Suitable aqueous and non-aqueous carriers, diluents, solvents or excipients include water, ethanol, polyols and any suitable mixtures thereof.

Dosage forms for topical administration of the compound of this invention include ointments, powders, patches, sprays and inhalants. The active ingredient is mixed with physiologically acceptable carriers and any preservatives, buffers, or propellants that may be required if necessary under sterile conditions.

The compound of the present invention can be administrated alone, or in combination with any other pharmaceutically acceptable compounds.

When the pharmaceutical compositions are used, a safe and effective amount of compound of the present invention is applied to mammal (such as human) need of treatment, wherein the dose of administration is a pharmaceutically effective dose. For a person weighed 60 kg, the daily dose is usually 0.2-1000 mg, preferably 0.5-500 mg. Of course, the particular dose should also depend on various factors, such as the route of administration, patient healthy status, which are well within the skills of an experienced physician.

The present invention will be further illustrated below with reference to the specific examples. It should be understood that these examples are only to illustrate the invention but not to limit the scope of the invention. The experimental methods with no specific conditions described in the following examples are generally performed under the conventional conditions, or according to the manufacturer's instructions. Unless indicated otherwise, percentage and parts are calculated by weight.

SYNTHESIS EXAMPLE

Method 1: Synthesis of Compound OY-7-34

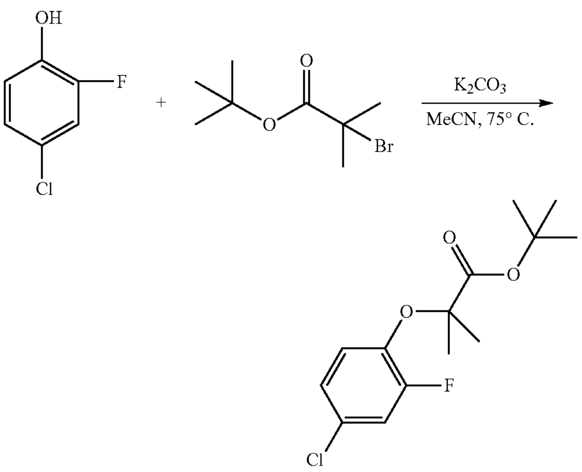

Tert-butyl 2-(4-chloro-2-fluorophenoxy)-2-methylpropanoate: tert-butyl 2-bromoisobutyrate (1.06 g, 4.8 mmol) was dissolved in 10 ml of acetonitrile. Anhydrous potassium carbonate (942 mg, 6.8 mmol) was added at room temperature and the mixture was mixed in a 30 ml pressure flask and stirred uniformly. 4-Chloro-2-fluorophenol (500 mg, 3.4 mmol) was added dropwise to the suspension and the mixture was stirred uniformly. The temperature was slowly raised to 75° C. and the mixture was vigorously stirred for 8 hours. After the reaction was completed, the acetonitrile was removed by rotary evaporator, 10 ml of ethyl acetate was added to dissolve. The mixture was transferred to separatory funnel, washed with 10 ml of distilled water, and extracted with ethyl acetate (20 ml*3). The organic phases were combined, washed with saturated sodium chloride (10 ml*2), dried over anhydrous sodium sulfate, filtered and spin-dried to remove the solvent, and then separated and purified by silica gel column chromatography (petroleum ether:ethyl acetate=0-25%) to obtain 485 mg of colorless transparent oily liquid with a yield of 50%. 1H NMR (400 MHz, DMSO-d6) δ 7.47 (m, 1H), 7.21 (m, 1H), 6.97 (t, J=8.9 Hz, 1H), 1.50 (s, 6H), 1.40 (s, 9H).

Synthesis of Intermediate QY-4-56

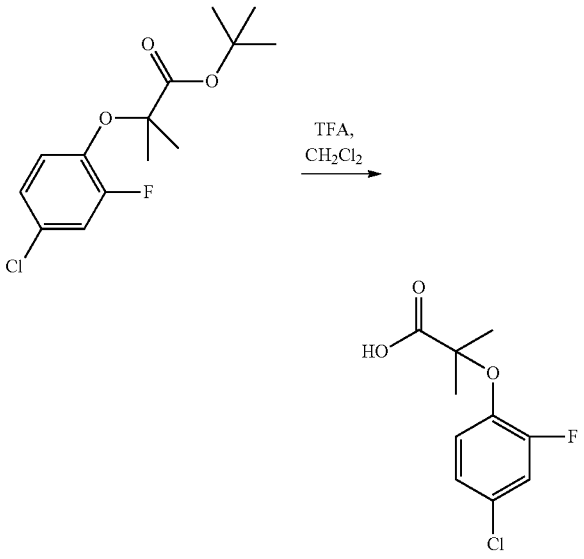

2-(4-Chloro-2-fluorophenoxy)-2-methylpropanoic acid: QY-7-34 (485 mg, 1.68 mmol) was dissolved in 5 ml of dichloromethane, and the solution was transferred to 15 ml pressure flask. 1 ml of trifluoroacetic acid was added dropwise to the reaction solution at room temperature, and the solution was mixed and stirred evenly. The reaction was monitored in real time by LC-MS, which was completed in 5 hours. The reaction mixture was transferred to 100 ml round-bottomed flask, and 30 ml of dichloromethane was added. The solvent was removed by rotary evaporator. The mixture was separated and purified by C18 reverse phase chromatography (water:acetonitrile=0-80%) to obtain 370 mg of white solid with a yield of 95% MS (ESI) m/z 231 (M−H)−.

Synthesis of Compound QY-7-35

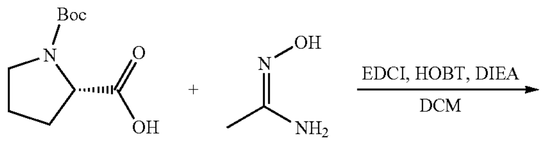

-continued

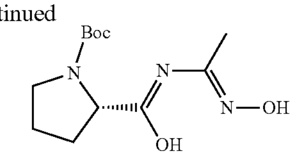

3-(S,Z)-1-(Tert-butoxycarbonyl)-N-((E)-1-(hydroxyimino)ethyl)pyrrolidine-2-carbimidic acid: 20 ml of dichloromethane, and 1-hydroxybenzotriazole (503 mg, 3.72 mmol) were added sequencely in a 30 ml pressure flask and stirred to dissolve. Boc-L-proline (800 mg, 3.7 mmol), and N-hydroxyacetamidine (330 mg, 4.4 mmol) were added, and the mixture was stirred at room temperature for 20 min. Then EDCI (1.06 g, 5.6 mmol) was added, and N,N-diisopropylethylamine (961 mg, 7.4 mmol) was added dropwise to the reaction solution, and vigorously stirred at room temperature for 3 hours. The reaction was monitored in real time by LC-MS until the reactants were consumed, and 20 ml of distilled water was added. The mixture was stirred and transferred to separatory funnel, extracted with dichloromethane (20 ml*3). The organic phases were combined, washed with saturated sodium bicarbonate (10 ml*1), washed with saturated sodium chloride (10 ml*2), dried over anhydrous sodium sulfate, filtered and spin-dried to remove the organic solvent, and separated and purified by silica gel column chromatography (dichloromethane: 2M ammonia methanol=0-10%) to obtain 556 mg of white solid with a yield of 55%. 1H NMR (400 MHz, DMSO-d6) δ 4.28 (m, 1H), 3.41-3.26 (m, 2H), 2.27-2.13 (m, 1H), 1.84 (m, 3H), 1.76 (s, 3H), 1.40 (s, 3.5H), 1.31 (s, 3.5H). MS (ESI) m/z 272 (M+H)+.

Synthesis of Compound QY-7-40

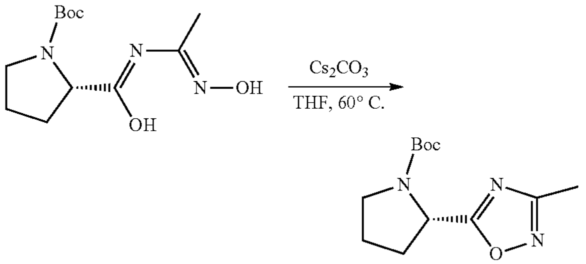

Compound QY-7-35 (244 mg, 0.90 mmol) was dissolved in 4 ml of tetrahydrofuran, and the solution was mixed and stirred in a 15 ml pressure flask. Cesium carbonate (586 mg, 1.80 mmol) was added at room temperature. Under the protection by nitrogen replacement, the mixture was slowly heated to 60° C., and vigorously stirred for 2 hours. The reaction was monitored by TLC until the reaction of raw materials was completed. The tetrahydrofuran was removed by rotary evaporator, 10 ml of ethyl acetate was added to dissolve. Cesium carbonate was removed by diatomaceous earth suction filtration and the mixture was rinsed using ethyl acetate (20 ml*3), methanol (5 ml*2) to wash diatomaceous earth. The obtained organic phase was removed by rotary evaporator, and separated and purified by silica gel column chromatography (petroleum ether:ethyl acetate=0-70%) to obtain 190 mg of colorless transparent oily liquid with a yield of 83%. 1H NMR (400 MHz, DMSO-d6) δ

5.04-4.94 (m, 1H), 3.54-3.35 (m, 2H), 2.40-2.33 (m, 1H), 2.33 (s, 3H), 1.94 (m, 3H), 1.38 (s, 3.5H), 1.20 (s, 5.5H). MS (ESI) m/z 198 (M+H)+.

Synthesis of Compound QY-1-95

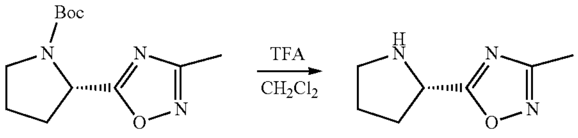

QY-7-40 (100 mg, 0.39 mmol) was dissolved in 3 ml of dichloromethane, and the solution was transferred to 8 ml pressure flask. 0.3 ml of trifluoroacetic acid was added dropwise to the reaction solution at room temperature, and the solution was mixed and stirred well. The reaction was monitored in real time by LC-MS which was completed in 2.5 hours. The reaction solution was transferred to 100 ml round-bottomed flask, 20 ml of dichloromethane was added, and the solvent was removed by a rotary evaporator; the reaction mixture was separated and purified by C18 reversed-phase chromatography column (water:acetonitrile=0-80%) to obtain 54 mg of pale yellow oily liquid with a yield of 90%. MS (ESI) m/z 154 (M+H)+.

Synthesis of Compound QY-3-27

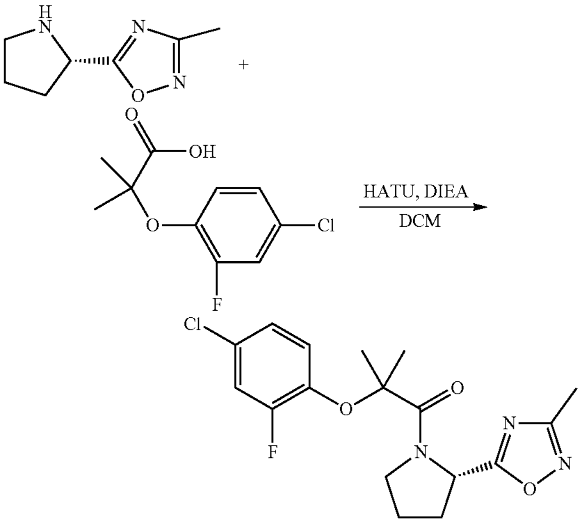

(S)-2-(4-Chloro-2-fluorophenoxy)-2-methyl-1-(2-(3-methyl-1,2,4-oxadiazol-5-yl)pyrrolidin-1-yl)propan-1-one: QY-1-95 (54 mg, 0.35 mmol) was dissolved in 1 ml of dichloromethane in an 8 ml pressure flask, and HATU (160 mg, 0.42 mmol) was added. QY-4-56 (90 mg, 0.39 mmol) was dissolved in 1 ml of dichloromethane, and added dropwise to the well-stirred reaction solution; N,N-diisopropylethylamine (137 mg, 1.1 mmol) was added dropwise under ice bath conditions, and the mixture was stirred for 10 min, and gradually returned to room temperature and then stirred to react for 4 hours. The reaction was monitored in real time by LC-MS until it was completed, 5 ml of dichloromethane was added to dilute the reaction solution. The reaction mixture was transferred to a separatory funnel, washed with 5 ml of distilled water, extracted with dichloromethane (5 ml*3). The organic phases were combined, washed with saturated sodium chloride (5 ml*2). The organic phase obtained after post-processing was dried over anhydrous sodium sulfate, filtered and spin-dried to remove dichloromethane, and separated and purified by silica gel column chromatography (petroleum ether:ethyl acetate=0-30%) to obtain 90 mg of light yellow transparent oily liquid with a yield of 70%. 1H NMR (400 MHz, DMSO-d6) δ 7.51 (m, 1H), 7.16 (m, 1H), 7.03 (m, 1H), 5.26 (dd, J=8.5, 4.6 Hz, 1H), 3.86-3.74 (m, 2H), 2.34 (s, 3H), 2.27-2.18 (m, 1H), 1.96 (m, 2H), 1.85-1.77 (m, 1H), 1.52 (s, 3H), 1.46 (s, 3H). MS (ESI) m/z 368 (M+H)+.

Method 2: Synthesis of Compound ZSQ-13-49

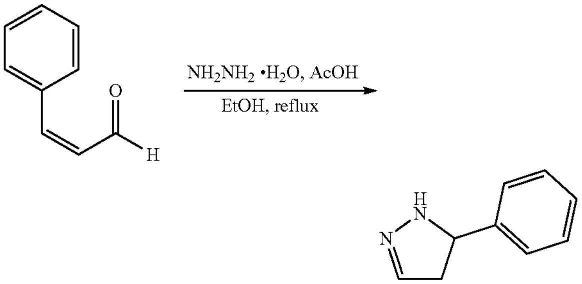

4-Phenyl-4,5-dihydro-1H-pyrazole: 182 mg of hydrazine hydrate and 4 ml of absolute ethanol was added into a 15 ml pressure flask, stirred and mixed well. Acetic acid (216 mg, 3.6 mmol) was slowly added dropwise to the ethanol solution under ice bath conditions and the resulting mixture was stirred for ten minutes; cinnamaldehyde (400 mg, 3.0 mmol) was dissolved in 2 ml of anhydrous ethanol and the ethanol solution was slowly dropped into the reaction solution under ice bath conditions. The mixture was refluxed and stirred for 3.5 hours. The reaction was monitored in real time by LC-MS until the reactants were completely consumed. Ethanol was removed by a rotary evaporator, 5 ml of ethyl acetate was added to dilute the reaction solution, and the pH was adjusted to neutral with saturated sodium bicarbonate. Then the mixture was transferred to a separatory funnel, washed with distilled water (4 ml*2), extracted with ethyl acetate (5 ml*3). The organic phases were combined, washed with saturated sodium chloride (5 ml*2). The organic phase obtained after post-treatment was dried over anhydrous sodium sulfate, filtered and spin-dried to remove ethyl acetate, separated and purified by C18 reverse phase chromatography column (water:acetonitrile=0-80%) to obtain 294 mg of yellow oily liquid with a yield of 67%. 1H NMR (400 MHz, DMSO-d6) δ 7.39-7.34 (m, 5H), 7.33-7.29 (m, 1H), 7.25 (s, 1H), 4.74 (t, J=10.0 Hz, 1H), 3.22 (m, 1H), 2.75 (m, 1H). MS (ESI) m/z 147 (M+H)+.

Synthesis of Compound ZSQ-13-56

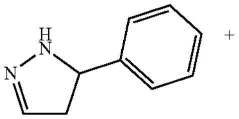

-continued

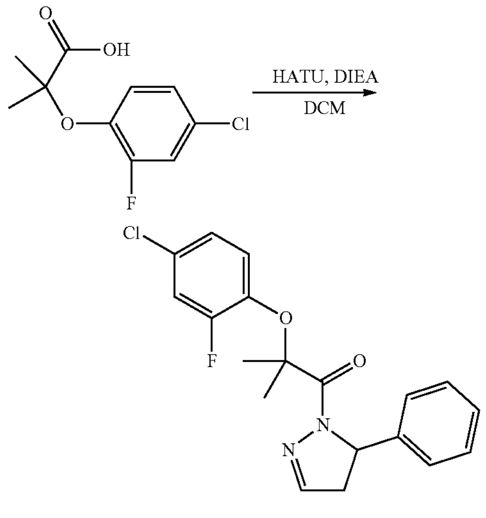

2-(4-Chloro-2-fluorophenoxy)-2-methyl-1-(5-phenyl-4,5-dihydro-1H-pyrazol-1-yl)propan-1-one: ZSQ-13-49 (30 mg, 0.2 mmol) was dissolved in 1 ml of dichloromethane and added to an 8 ml pressure flask. HATU (114 mg, 0.3 mmol) was added to the mixture. QY-4-56 (46 mg, 0.2 mmol) was dissolved in 1 ml of dichloromethane which was added dropwise into the well-stirred reaction solution; N,N-diisopropylethylamine (77 mg, 0.6 mmol) was added dropwise under ice bath conditions, and the mixture was stirred and reacted for 3.5 hours after gradually returning to room temperature. The reaction was monitored in real time by LC-MS until the reactants were consumed, 5 ml of dichloromethane was added to dilute the reaction solution. The reaction solution was transferred to a separatory funnel, washed with 4 ml of distilled water, extracted with dichloromethane (5 ml*3). The organic phases were combined, and washed with saturated sodium chloride (5 ml*2). The resulting organic phase was dried over anhydrous sodium sulfate, filtered and spin-dried to remove dichloromethane, and separated and purified by C18 reverse phase chromatography (water:acetonitrile=30%-90%) to obtain 27 mg of light yellow transparent oily liquid with a yield of 37%. 1H NMR (400 MHz, DMSO) δ 7.41 (m, 1H), 7.34-7.24 (m, 4H), 7.07 (dd, J=5.2, 3.1 Hz, 2H), 6.95 (m, 1H), 6.71 (t, J=9.0 Hz, 1H), 5.36 (m, 1H), 3.43-3.35 (m, 1H), 2.62 (m, 1H), 1.64 (s, 3H), 1.62 (s, 3H). MS (ESI) m/z 361 (M+H)+.

Method 3

Synthesis of compound QY-7-36

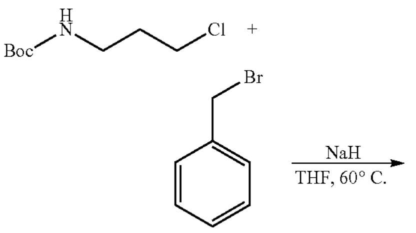

-continued

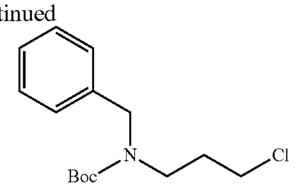

Tert-butyl benzyl(3-chloropropyl)carbamate: N-Boc-3-chloropropylamine (1.0 g, 5.2 mmol) was mixed into 10 ml of tetrahydrofuran, and added to a 30 ml pressure flask and stirred; sodium hydride (190 mg, 4.8 mmol) was dissolved in 5 ml of tetrahydrofuran, the resulting solution was added dropwise to the suspension at 0° C. After the reaction solution was stirred for 15 min under ice bath conditions, benzyl bromide (680 mg, 40 mmol) was slowly added dropwise, and the temperature was gradually raised to 60° C. The reaction was stopped after stirring for 8 h. Distilled water was added dropwise to quench the reaction under ice bath conditions. After the reaction solution was stirred until pale yellow, clear and transparent, the stirring was stopped. The reaction solution was transferred to a rotary evaporator to remove tetrahydrofuran. The reaction system was diluted with 10 ml of ethyl acetate, which was transferred to a separatory funnel, washed with 10 ml of distilled water, and then extracted by the addition of ethyl acetate (15 ml*3). The organic phases were combined, washed with saturated sodium chloride (10 ml*2), dried over anhydrous sodium sulfate, filtered and rotary evaporated to remove ethyl acetate, and separated and purified by silica gel column chromatography (petroleum ether:ethyl acetate=0-25%) to obtain 325 mg of colorless permeable liquid with a yield of 29%. 1H NMR (400 MHz, DMSO-d6) δ 7.38-7.21 (m, 5H), 4.38 (s, 2H), 3.59 (t, J=6.4 Hz, 2H), 3.24 (s, 2H), 1.89 (m, 2H), 1.43 (s, 9H). MS(ESI) m/z 228 (M+H)+.

Synthesis of Compound QY-7-41

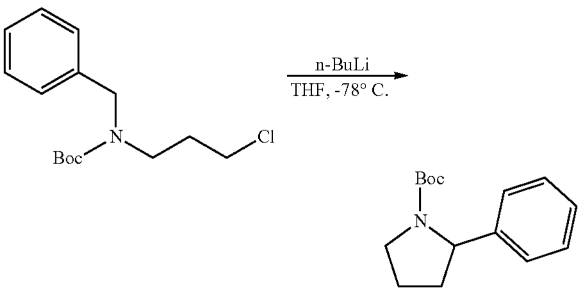

Tert-butyl 2-phenylpyrrolidine-1-carboxylate: 8 ml of ultra-dry tetrahydrofuran was added into a 30 ml pressure flask containing QY-7-36 (293 mg, 1.0 mmol), and the mixture was stirred and mixed well. The reaction system was transferred to an acetone-carbon dioxide ice bath and cooled to −78° C. n-Butyllithium (0.66 ml of 2.5M solution, 1.7 mmol) was slowly added dropwise, and the reaction solution gradually changed from colorless and transparent to orange-yellow solution, stirred for 0.5 h, then moved to room temperature and continued to stir for 2.5 h. The reaction was monitored in real time by LC-MS until the reactants were completely consumed, and ice water was added dropwise to quench the reaction. After the reaction solution changed from clear to clouding and then became light yellow, clear and transparent, the tetrahydrofuran was removed by rotary evaporation. The reaction solution was diluted with 10 ml of ethyl acetate, transferred to a separatory funnel, washed with 15 ml of distilled water, and then extracted with ethyl acetate (15 ml*3). The organic phases were combined, washed with saturated sodium chloride (10 ml*2), dried over anhydrous sodium sulfate. The extract was filtered, rotary evaporated to remove ethyl acetate, separated and purified by silica gel column chromatography (petroleum ether:ethyl acetate=0-20%) to obtain 138 mg of light yellow oily liquid with a yield of 56%. MS (ESI) m/z 192 (M+H)+.

Synthesis of Compound QY-7-43

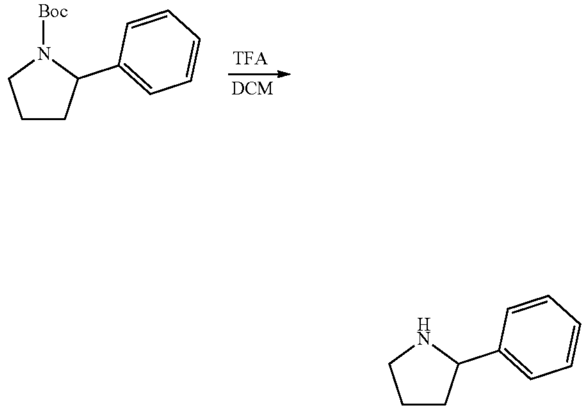

2-Phenylpyrrolidine: QY-7-41 (60 mg, 0.24 mmol) was dissolved in 1 ml of dichloromethane, and the mixture was transferred to an 8 ml pressure flask. 0.1 ml of trifluoroacetic acid was added dropwise to the reaction solution at room temperature, and the mixture was mixed well under stirring. The reaction was monitored in real time by LC-MS, and the raw material was completely consumed in 2 hours. The reaction solution was transferred to a 100 ml round-bottomed flask, 20 ml of dichloromethane was added, and the solvent was removed by a rotary evaporator to obtain a crude product which was proceed directly to the next reaction. MS (ESI) m/z 148 (M+H)+.

Synthesis of Compound OY-3-99

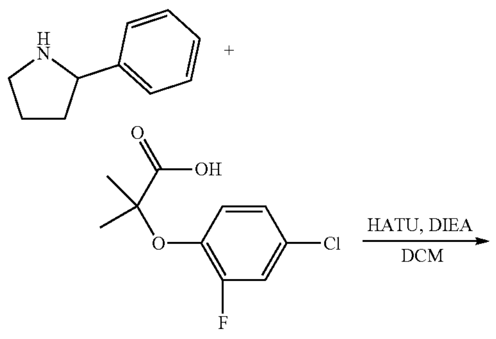

-continued

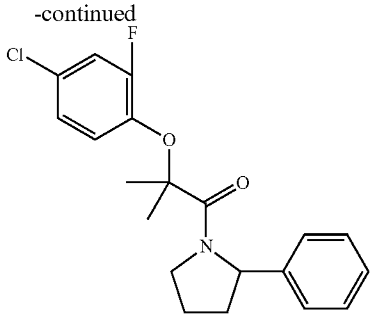

2-(4-Chloro-2-fluorophenoxy)-2-methyl-1-(2-phenylpyrrolidin-1-yl)propan-1-one

In an 8 ml pressure flask, QY-7-43 (50 mg, 0.34 mmol) was dissolved in 1 ml dichloromethane, and HATU (155 mg, 0.41 mmol) was added. QY-4-56 (79 mg, 0.34 mmol) was dissolved in 2 ml of dichloromethane which was added dropwise to the well-stirred reaction solution. N,N-diisopropylethylamine (110 mg, 0.85 mmol) was added dropwise at room temperature, and the mixture was continued to stir and react for 4 hours. The reaction was monitored in real time by LC-MS until the reactants were completely consumed, the reaction solution was diluted by adding 5 ml of dichloromethane, transferred to a separatory funnel, washed with 10 ml of distilled water, and extracted with dichloromethane (10 ml*3). The organic phases were combined, washed with saturated sodium chloride (5 ml*2). The organic phase was dried over anhydrous sodium sulfate, filtered and rotary evaporated to remove dichloromethane, separated and purified by silica gel column chromatography (petroleum ether: ethyl acetate=0-25%) to obtain 55 mg of pale yellow oily liquid with a yield of 45%. 1H NMR (400 MHz, DMSO-d6) δ 7.53 (m, 1H), 7.29 (t, J=7.4 Hz, 2H), 7.22-7.09 (m, 4H), 6.79 (t, J=9.0 Hz, 1H), 5.07 (dd, J=8.1, 4.3 Hz, 1H), 3.88-3.74 (m, 2H), 2.18-2.08 (m, 1H), 1.97-1.61 (m, 3H), 1.58 (s, 3H), 1.48 (s, 3H). MS (ESI) m/z 362 (M+H)+

Method 4

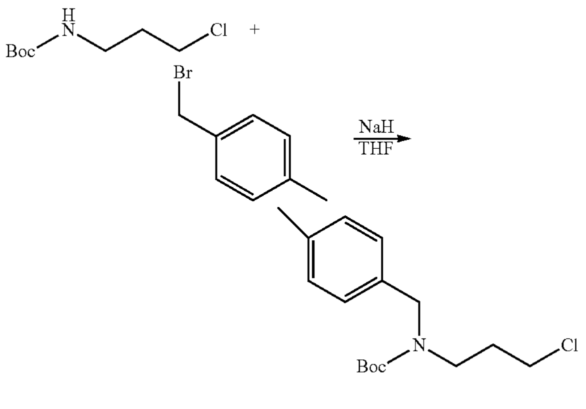

Synthesis of Compound QY-5-12

Tert-butyl (3-chloropropyl)(4-methylbenzyl)carbamate: in a 30 ml pressure flask, N-Boc-3-chloropropylamine (628 mg, 3.2 mmol) was stirred and mixed-well in 6 ml of tetrahydrofuran. Sodium hydride (173 mg, 4.3 mmol) was dissolved in 4 ml of tetrahydrofuran which was added dropwise to the above suspension at 0° C., stirred for 15 min under ice bath conditions, and p-Methylbenzyl bromide (400 mg, 2.1 mmol) was slowly added dropwise to the reaction solution. The temperature was gradually raised to 60° C. The reaction was monitored by thin layer chromatography, and the reaction was stopped after stirring for 8 h. Ice water was added dropwise under ice bath to quench the reaction. After the reaction solution was stirred until pale yellow, clear and transparent, the stirring was stopped. The reaction solution was transferred to a rotary evaporator to remove tetrahydrofuran. The reaction system was diluted with 10 ml of ethyl acetate, transferred to a separatory funnel, washed with 10 ml of distilled water, and then extracted by the addition of ethyl acetate (15 ml*3). The organic phases were combined, washed with saturated sodium chloride (10 ml*2), dried over anhydrous sodium sulfate, filtered and rotary evaporated to remove ethyl acetate, and separated and purified by silica gel column chromatography (petroleum ether:ethyl acetate=0-25%) to obtain 304 mg of pale yellow transparent liquid with a yield of 47%. 1H NMR (400 MHz, DMSO-d6) δ 7.06 (q, J=8.1 Hz, 4H), 4.26 (s, 2H), 3.51 (t, J=6.4 Hz, 2H), 3.14 (s, 2H), 2.21 (s, 3H), 1.85-1.76 (m, 2H), 1.34 (s, 9H). MS (ESI) m/z 242 (M+H)+.

Synthesis of Compound OY-5-16

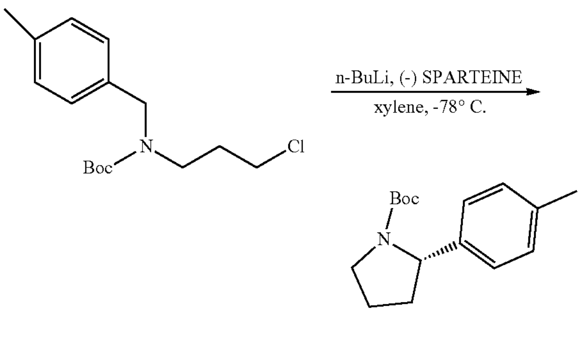

Tert-butyl (S)-2-(p-tolyl)pyrrolidine-1-carboxylate: 6 ml of ultra-dry xylene was added to a 30 ml pressure flask containing (−) spartein (280 mg, 1.2 mmol). The reaction system was transferred to an acetone-carbon dioxide ice bath and cooled to −78° C. n-Butyllithium (0.6 ml of 2.5M solution, 1.5 mmol) was slowly added, and the mixture was stirred for 10 min keeping the same temperature. And then a 4 ml solution of ultra-dry xylene containing QY-5-12 (300 mg, 10 mmol) was added dropwise, and the reaction solution changed from colorless and transparent to pale yellow suspension, stirred at −78° C. for 0.5 h, then moved to room temperature and continued to stir for 3 h. The reaction was monitored in real time by LC-MS until the reactants were completely consumed, and ice water was added dropwise to quench the reaction. After the reaction solution changed from clear to clouding and then became light yellow, clear and transparent, the reaction solution was diluted with 10 ml of ethyl acetate, washed with 10 ml of distilled water, and then extracted with ethyl acetate (15 ml*3). The organic phases were combined, washed with saturated sodium chloride (10 ml*2), dried over anhydrous sodium sulfate. The extract was filtered, rotary evaporated to remove ethyl acetate and xylene, separated and purified by silica gel column chromatography (petroleum ether:ethyl acetate=0-25%) to obtain 116 mg of colorless and transparent oily liquid with a yield of 44%. $^1$H NMR (400 MHz, DMSO-d6) δ 7.11 (d, J=7.7 Hz, 2H), 7.03 (d, J=7.0 Hz, 2H), 4.83-4.63 (m, 1H), 3.56-3.39 (m, 2H), 2.27 (s, 3H), 2.23 (m, 1H), 1.84-1.59 (m, 3H), 1.38 (s, 4H), 1.10 (s, 5H). MS (ESI) m/z 206 (M+H)+.

Synthesis of Compound QY-5-20

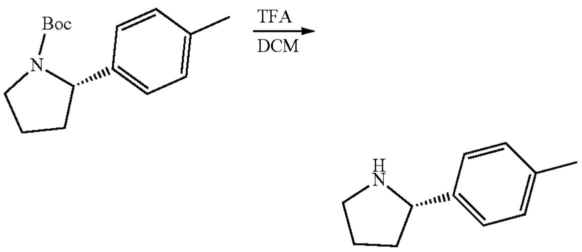

(S)-2-(p-Tolyl)pyrrolidine: QY-5-16 (116 mg, 0.44 mmol) was dissolved in 2 ml of dichloromethane, and the mixture was transferred to an 8 ml pressure flask. 0.2 ml of trifluoroacetic acid was added dropwise to the reaction solution at room temperature, and the mixture was mixed and stirred well. The reaction was monitored in real time by LC-MS, and the raw material was completely consumed in 1.5 hours. The reaction solution was transferred to a 100 ml round-bottomed flask, 30 ml of dichloromethane was added, and the solvent was removed by a rotary evaporator. The above operations were repeated to remove trifluoroacetic acid to obtain a crude product which was proceeded directly to the next reaction. MS (ESI) m/z 162 (M+H)+.

Synthesis of Compound QY-5-22

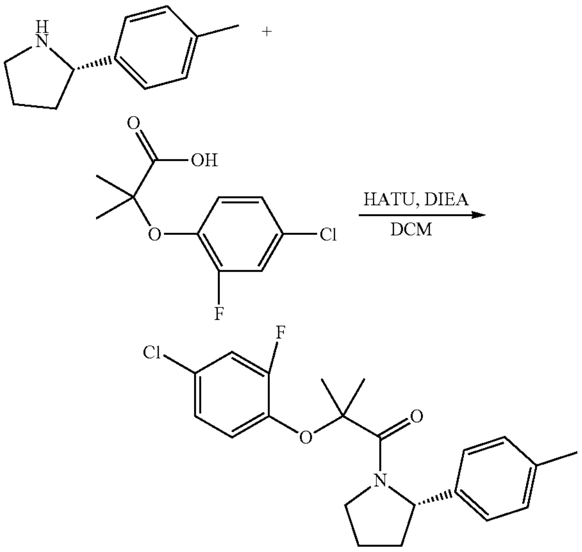

(S)-2-(4-Chloro-2-fluorophenoxy)-2-methyl-1-(2-(p-tolyl)pyrrolidin-1-yl)propan-1-one: in an 8 ml pressure flask, QY-5-20 (0.22 mmol) was dissolved in 2 ml of dichloromethane, and HATU (127 mg, 0.33 mmol) was added. QY-4-56 (78 mg, 0.33 mmol) was dissolved in 2 ml of dichloromethane which was added dropwise to the well-stirred reaction solution. N,N-diisopropylethylamine (86 mg, 0.67 mmol) was slowly added dropwise under ice bath conditions, and the mixture was continued to stir and react for 4 hours. The reaction was monitored in real time by LC-MS until the reactants were completely consumed. The reaction solution was diluted by adding 5 ml of dichloromethane, transferred to a separatory funnel, washed with 10 ml of distilled water, and extracted with dichloromethane (15 ml*3). The organic phases were combined, washed with saturated sodium chloride (10 ml*2). The organic phase was dried over anhydrous sodium sulfate, filtered and evaporated to remove dichloromethane, and separated and purified by silica gel column chromatography (petroleum ether:ethyl acetate=0-25%) to obtain 46 mg of pale yellow oily liquid with a yield of 56%. 1H NMR (400 MHz, DMSO-d6) δ 7.52 (m, 1H), 7.15 (m, 1H), 7.09 (d, J=7.9 Hz, 2H), 6.98 (d, J=8.0 Hz, 2H), 6.78 (t, J=9.0 Hz, 1H), 5.03 (dd, J=8.0, 4.4 Hz, 1H), 3.86-3.69 (m, 2H), 2.27 (s, 3H), 2.09 (m, 1H), 1.92-1.59 (m, 3H), 1.56 (s, 3H), 1.48 (s, 3H). MS (ESI) m/z 376 (M+H)+.

By substituting different synthetic substrates, the compounds shown in the following table were obtained:

| Compound number | Chemical structure | Compound number | Chemical structure |
|---|---|---|---|
| QY-1-98 | 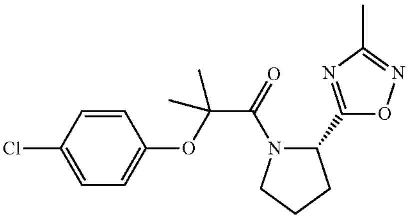 [SMILES: Cc1noc([C@@H]2CCCN2C(=O)C(C)(C)Oc2ccc(Cl)cc2)n1] | QY-4-6 | 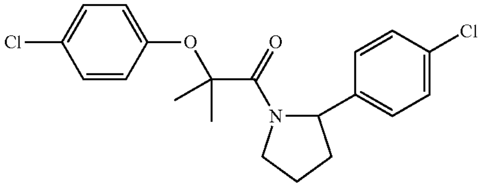 [SMILES: CC(C)(Oc1ccc(Cl)cc1)C(=O)N1CCCC1c1ccc(Cl)cc1] |
| QY-2-25 | 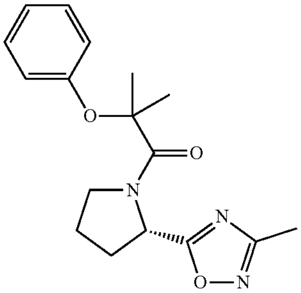 [SMILES: Cc1noc([C@@H]2CCCN2C(=O)C(C)(C)Oc2ccccc2)n1] | QY-4-7 | 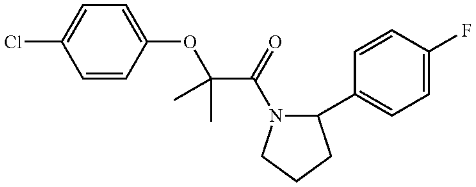 [SMILES: CC(C)(Oc1ccc(Cl)cc1)C(=O)N1CCCC1c1ccc(F)cc1] |
| QY-2-26 | 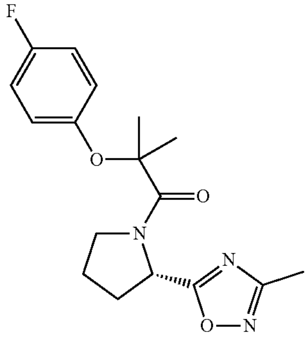 [SMILES: Cc1noc([C@@H]2CCCN2C(=O)C(C)(C)Oc2ccc(F)cc2)n1] | QY-4-8 | 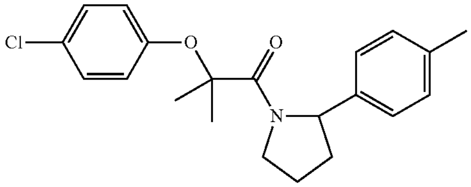 [SMILES: Cc1ccc(C2CCCN2C(=O)C(C)(C)Oc2ccc(Cl)cc2)cc1] |
| QY-2-27 | 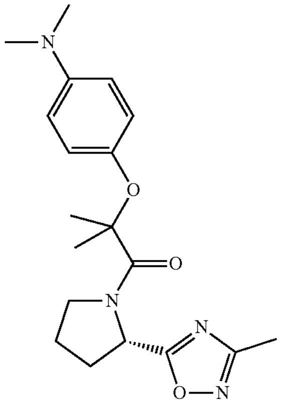 | QY-4-11 | 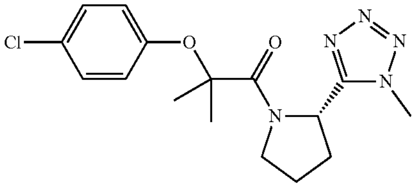 [SMILES: Cn1nnnc1[C@@H]1CCCN1C(=O)C(C)(C)Oc1ccc(Cl)cc1] |

-continued
| Compound number | Chemical structure | Compound number | Chemical structure |
|---|---|---|---|
| QY-2-34 | 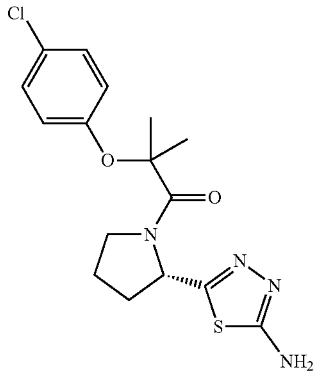 [SMILES: CC(C)(Oc1ccc(Cl)cc1)C(=O)N1CCC[C@H]1c1nnc(N)s1] | QY-4-12 | 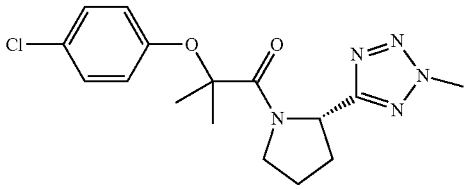 [SMILES: Cn1nnc([C@@H]2CCCN2C(=O)C(C)(C)Oc2ccc(Cl)cc2)n1] |
| QY-2-38 | 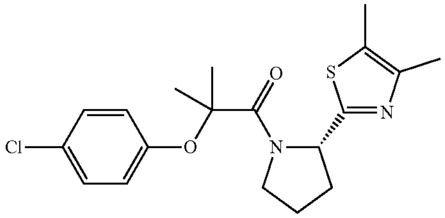 [SMILES: Cc1nc([C@@H]2CCCN2C(=O)C(C)(C)Oc2ccc(Cl)cc2)sc1C] | QY-4-14 | 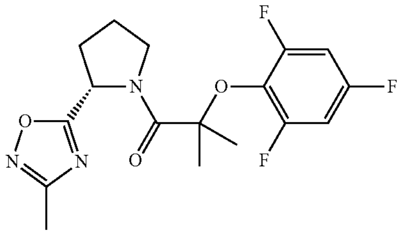 [SMILES: Cc1noc([C@@H]2CCCN2C(=O)C(C)(C)Oc2c(F)cc(F)cc2F)n1] |
| QY-2-39 | 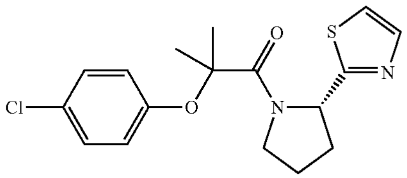 [SMILES: CC(C)(Oc1ccc(Cl)cc1)C(=O)N1CCC[C@H]1c1nccs1] | QY-4-27 | 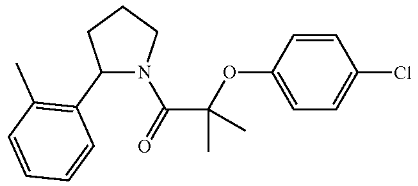 [SMILES: Cc1ccccc1C1CCCN1C(=O)C(C)(C)Oc1ccc(Cl)cc1] |
| QY-2-52 | 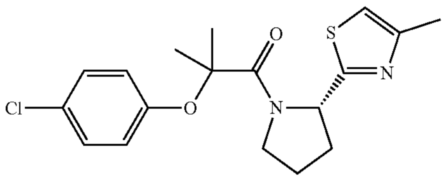 [SMILES: Cc1csc([C@@H]2CCCN2C(=O)C(C)(C)Oc2ccc(Cl)cc2)n1] | QY-4-32 | 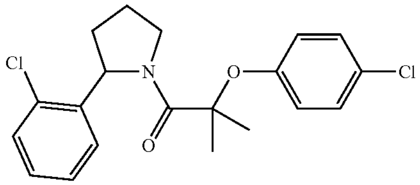 [SMILES: CC(C)(Oc1ccc(Cl)cc1)C(=O)N1CCCC1c1ccccc1Cl] |
| QY-2-53 | 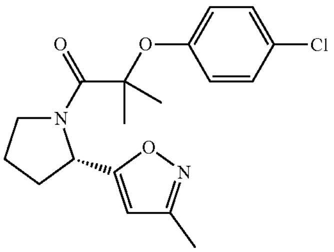 [SMILES: Cc1cc([C@@H]2CCCN2C(=O)C(C)(C)Oc2ccc(Cl)cc2)on1] | QY-4-35 | 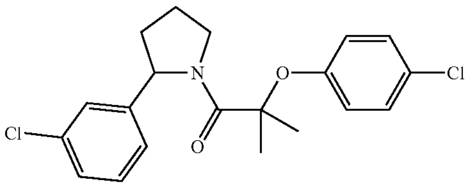 [SMILES: CC(C)(Oc1ccc(Cl)cc1)C(=O)N1CCCC1c1cccc(Cl)c1] |

-continued
| Compound number | Chemical structure | Compound number | Chemical structure |
|---|---|---|---|
| QY-2-54 | 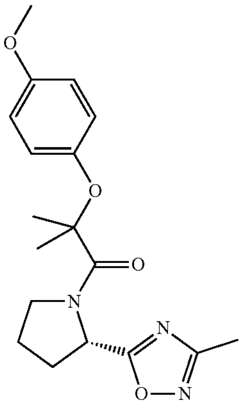 [SMILES: COc1ccc(OC(C)(C)C(=O)N2CCC[C@H]2c2nc(C)no2)cc1] | QY-4-39 | 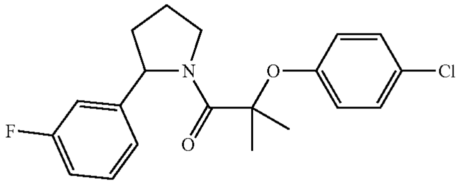 [SMILES: CC(C)(Oc1ccc(Cl)cc1)C(=O)N1CCCC1c1cccc(F)c1] |
| QY-2-55 | 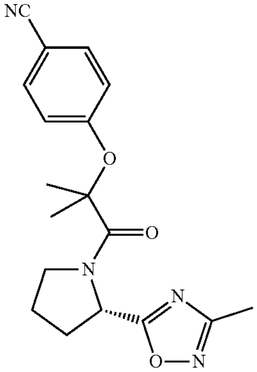 [SMILES: Cc1noc([C@@H]2CCCN2C(=O)C(C)(C)Oc2ccc(C#N)cc2)n1] | QY-4-66 | 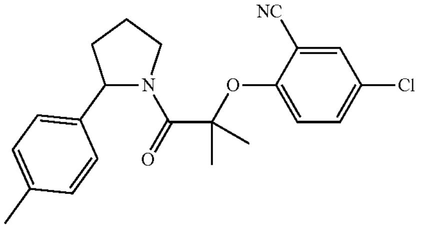 |
| QY-2-56 | 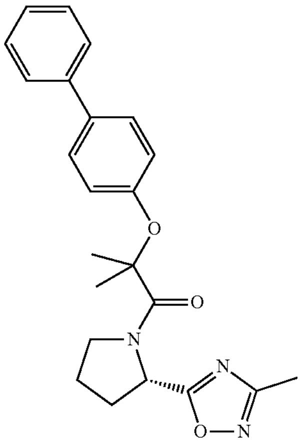 [SMILES: Cc1noc([C@@H]2CCCN2C(=O)C(C)(C)Oc2ccc(-c3ccccc3)cc2)n1] | QY-4-67 | 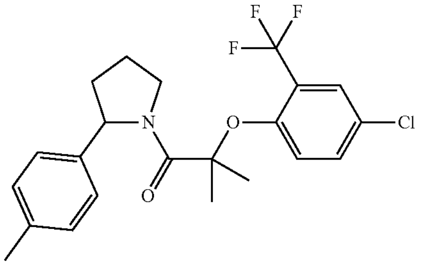 [SMILES: Cc1ccc(C2CCCN2C(=O)C(C)(C)Oc2ccc(Cl)cc2C(F)(F)F)cc1] |
| QY-2-75 | 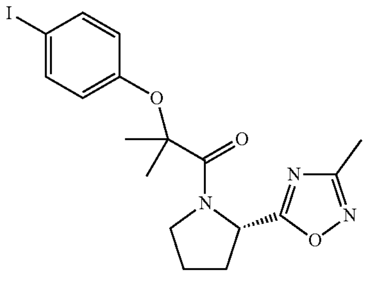 [SMILES: Cc1noc([C@@H]2CCCN2C(=O)C(C)(C)Oc2ccc(I)cc2)n1] | QY-4-69 | 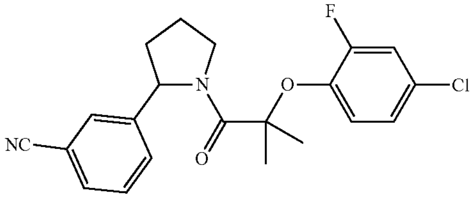 [SMILES: CC(C)(Oc1ccc(Cl)cc1F)C(=O)N1CCCC1c1cccc(C#N)c1] |

-continued
| Compound number | Chemical structure | Compound number | Chemical structure |
|---|---|---|---|
| QY-2-76 | 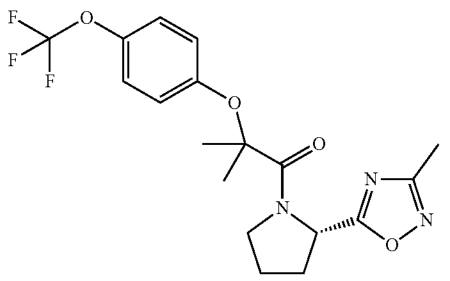 [SMILES: Cc1noc([C@@H]2CCCN2C(=O)C(C)(C)Oc2ccc(OC(F)(F)F)cc2)n1] | QY-4-70 | 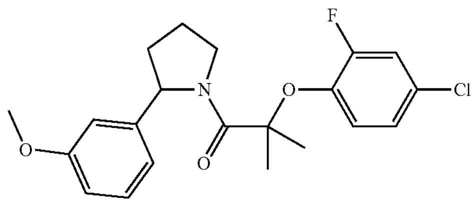 [SMILES: COc1cccc(C2CCCN2C(=O)C(C)(C)Oc2ccc(Cl)cc2F)c1] |
| QY-2-77 | 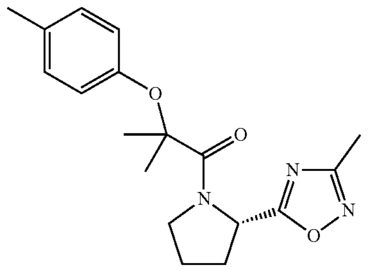 | QY-4-75 | 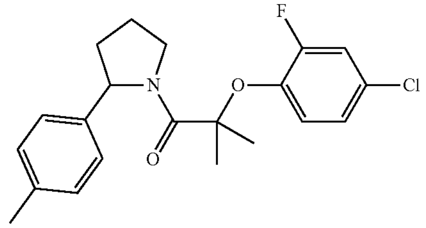 [SMILES: Cc1ccc(C2CCCN2C(=O)C(C)(C)Oc2ccc(Cl)cc2F)cc1] |
| QY-2-78 | 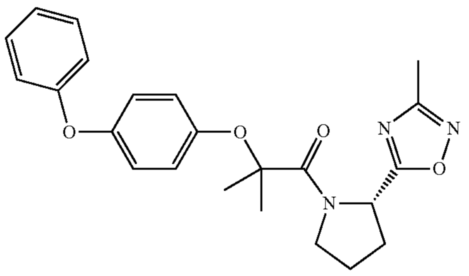 [SMILES: Cc1noc([C@@H]2CCCN2C(=O)C(C)(C)Oc2ccc(Oc3ccccc3)cc2)n1] | QY-4-78 | 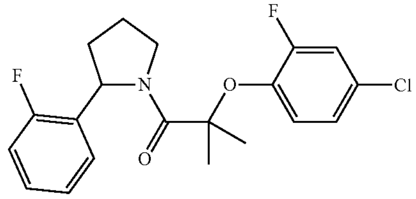 [SMILES: CC(C)(Oc1ccc(Cl)cc1F)C(=O)N1CCCC1c1ccccc1F] |
| QY-2-79 | 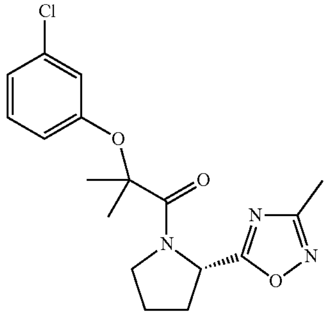 [SMILES: Cc1noc([C@@H]2CCCN2C(=O)C(C)(C)Oc2cccc(Cl)c2)n1] | QY-4-87 | 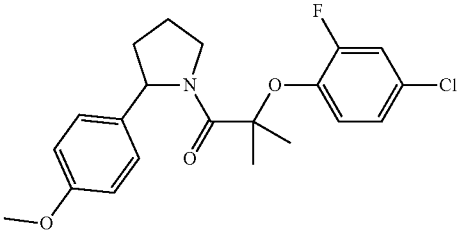 [SMILES: COc1ccc(C2CCCN2C(=O)C(C)(C)Oc2ccc(Cl)cc2F)cc1] |
| QY-2-100 | 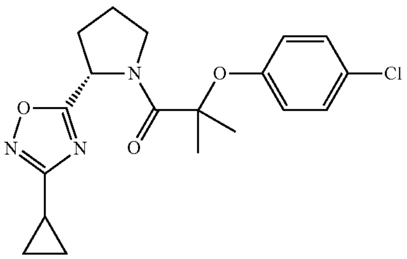 [SMILES: CC(C)(Oc1ccc(Cl)cc1)C(=O)N1CCC[C@H]1c1nc(C2CC2)no1] | QY-4-88 | 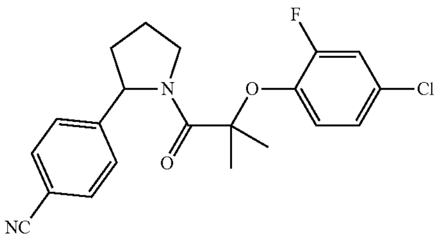 [SMILES: CC(C)(Oc1ccc(Cl)cc1F)C(=O)N1CCCC1c1ccc(C#N)cc1] |

-continued
| Compound number | Chemical structure | Compound number | Chemical structure |
| --- | --- | --- | --- |
| QY-2-103 | 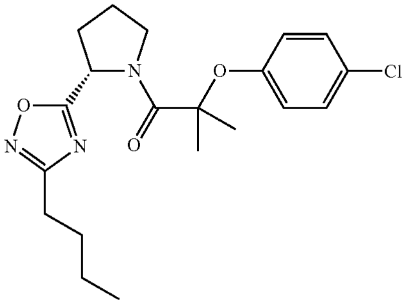 [SMILES: CCCCc1noc([C@@H]2CCCN2C(=O)C(C)(C)Oc2ccc(Cl)cc2)n1] | QY-4-96 | 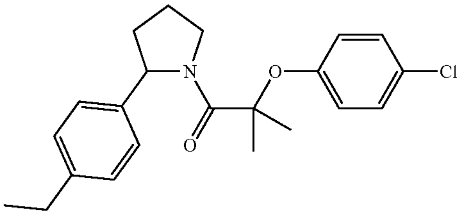 [SMILES: CCc1ccc(C2CCCN2C(=O)C(C)(C)Oc2ccc(Cl)cc2)cc1] |
| QY-2-104 | 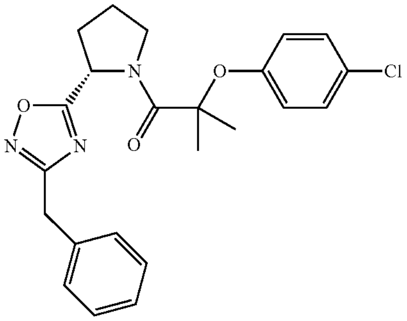 [SMILES: CC(C)(Oc1ccc(Cl)cc1)C(=O)N1CCC[C@H]1c1nc(Cc2ccccc2)no1] | QY-4-99 | 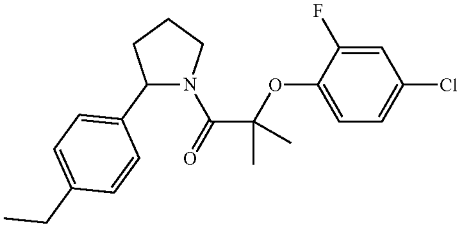 [SMILES: CCc1ccc(C2CCCN2C(=O)C(C)(C)Oc2ccc(Cl)cc2F)cc1] |
| QY-3-4 | 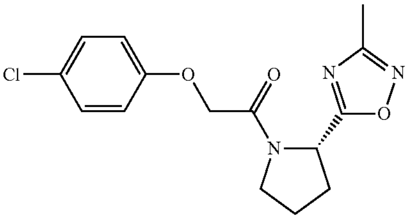 [SMILES: Cc1noc([C@@H]2CCCN2C(=O)COc2ccc(Cl)cc2)n1] | QY-5-1 | 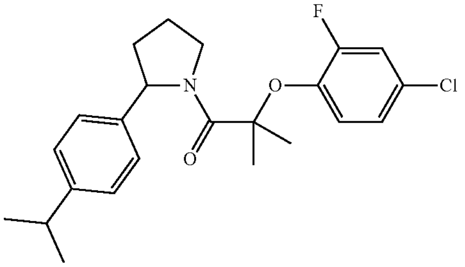 [SMILES: CC(C)c1ccc(C2CCCN2C(=O)C(C)(C)Oc2ccc(Cl)cc2F)cc1] |
| QY-3-11 | 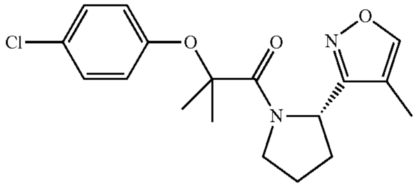 [SMILES: Cc1conc1[C@@H]1CCCN1C(=O)C(C)(C)Oc1ccc(Cl)cc1] | QY-5-4 | 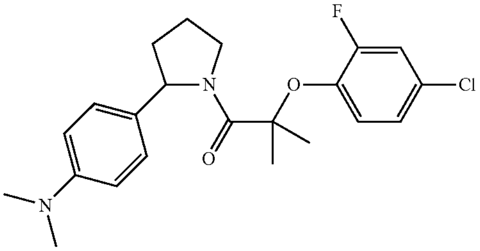 |
| QY-3-17 | 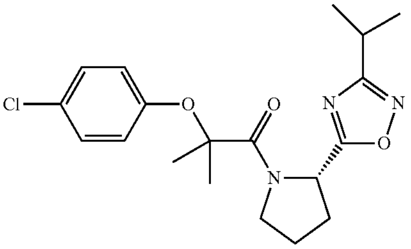 [SMILES: CC(C)c1noc([C@@H]2CCCN2C(=O)C(C)(C)Oc2ccc(Cl)cc2)n1] | QY-5-21 | 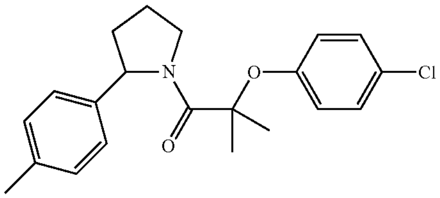 [SMILES: Cc1ccc(C2CCCN2C(=O)C(C)(C)Oc2ccc(Cl)cc2)cc1] |

-continued
| Compound number | Chemical structure | Compound number | Chemical structure |
|---|---|---|---|
| QY-3-26 | 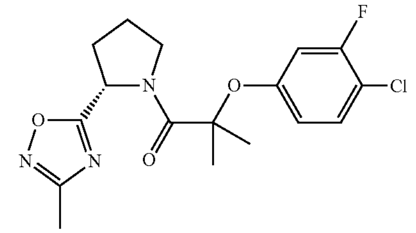 [SMILES: Cc1noc([C@@H]2CCCN2C(=O)C(C)(C)Oc2ccc(Cl)c(F)c2)n1] | QY-5-22 | 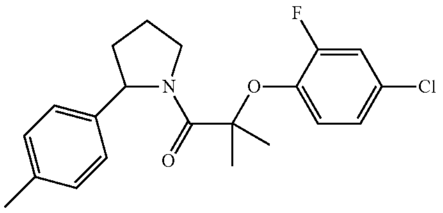 |
| QY-3-27 | 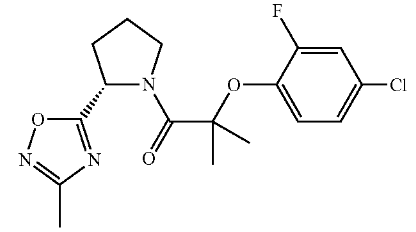 [SMILES: Cc1noc([C@@H]2CCCN2C(=O)C(C)(C)Oc2ccc(Cl)cc2F)n1] | QY-5-79 | 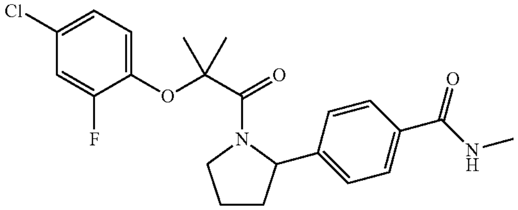 [SMILES: CNC(=O)c1ccc(C2CCCN2C(=O)C(C)(C)Oc2ccc(Cl)cc2F)cc1] |
| QY-3-28 | 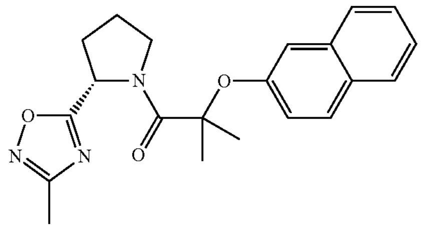 [SMILES: Cc1noc([C@@H]2CCCN2C(=O)C(C)(C)Oc2ccc3ccccc3c2)n1] | QY-5-83 | 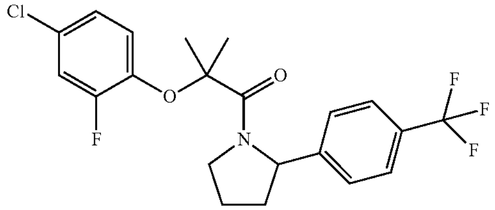 [SMILES: CC(C)(Oc1ccc(Cl)cc1F)C(=O)N1CCCC1c1ccc(C(F)(F)F)cc1] |
| QY-3-29 | 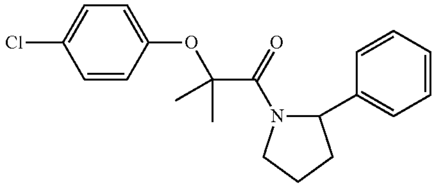 [SMILES: CC(C)(Oc1ccc(Cl)cc1)C(=O)N1CCCC1c1ccccc1] | QY-5-85 | 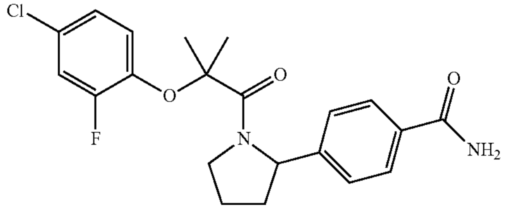 [SMILES: CC(C)(Oc1ccc(Cl)cc1F)C(=O)N1CCCC1c1ccc(C(N)=O)cc1] |
| QY-3-35 | 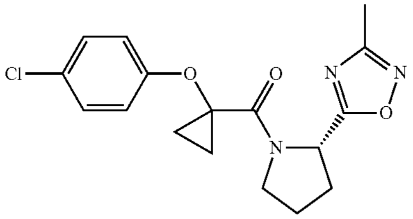 [SMILES: Cc1noc([C@@H]2CCCN2C(=O)C2(Oc3ccc(Cl)cc3)CC2)n1] | QY-6-47 | 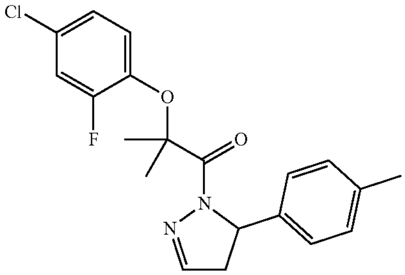 [SMILES: Cc1ccc(C2CC=NN2C(=O)C(C)(C)Oc2ccc(Cl)cc2F)cc1] |
| QY-3-36 | 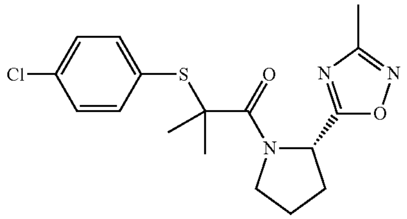 [SMILES: Cc1noc([C@@H]2CCCN2C(=O)C(C)(C)Sc2ccc(Cl)cc2)n1] | QY-6-60 | 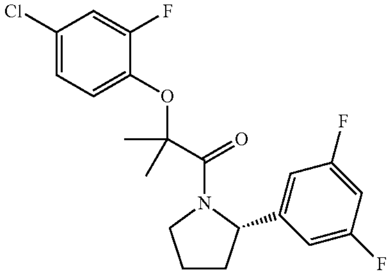 [SMILES: CC(C)(Oc1ccc(Cl)cc1F)C(=O)N1CCC[C@H]1c1cc(F)cc(F)c1] |

-continued
| Compound number | Chemical structure | Compound number | Chemical structure |
|---|---|---|---|
| QY-3-39 | 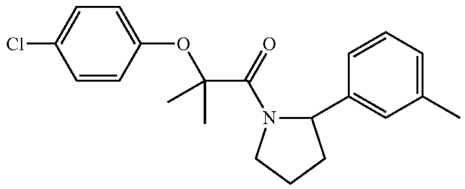 [SMILES: Cc1cccc(C2CCCN2C(=O)C(C)(C)Oc2ccc(Cl)cc2)c1] | QY-6-61 | 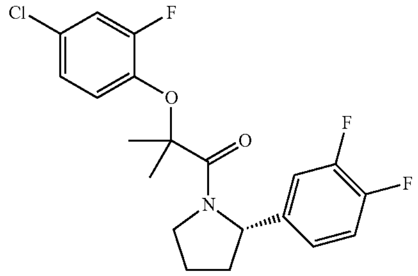 [SMILES: CC(C)(Oc1ccc(Cl)cc1F)C(=O)N1CCC[C@H]1c1ccc(F)c(F)c1] |
| QY-3-46 | 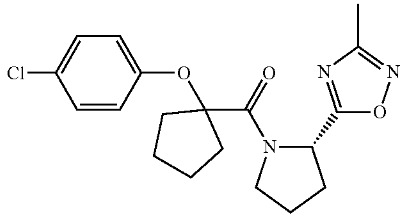 [SMILES: Cc1noc([C@@H]2CCCN2C(=O)C2(Oc3ccc(Cl)cc3)CCCC2)n1] | QY-6-62 | 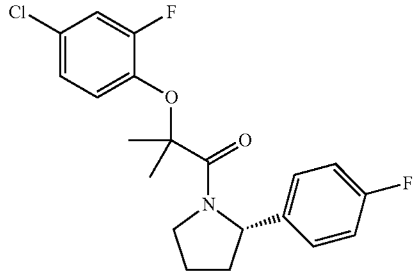 [SMILES: CC(C)(Oc1ccc(Cl)cc1F)C(=O)N1CCC[C@H]1c1ccc(F)cc1] |
| QY-3-51 | 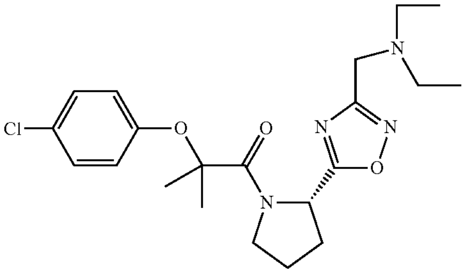 [SMILES: CCN(CC)Cc1noc([C@@H]2CCCN2C(=O)C(C)(C)Oc2ccc(Cl)cc2)n1] | QY-6-63 | 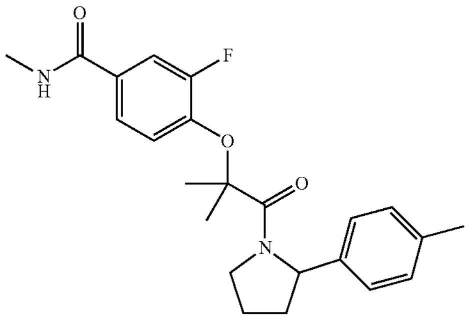 |
| QY-3-65 | 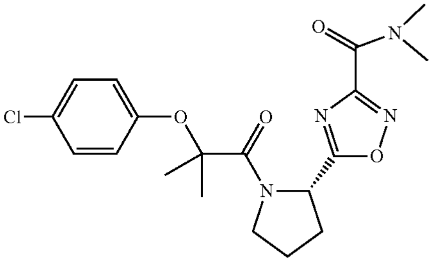 [SMILES: CN(C)C(=O)c1noc([C@@H]2CCCN2C(=O)C(C)(C)Oc2ccc(Cl)cc2)n1] | QY-6-83 | 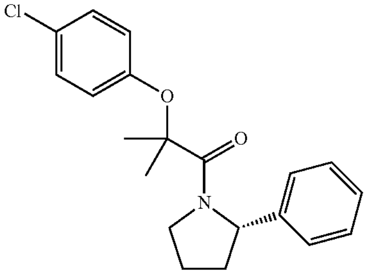 [SMILES: CC(C)(Oc1ccc(Cl)cc1)C(=O)N1CCC[C@H]1c1ccccc1] |
| QY-3-81 | 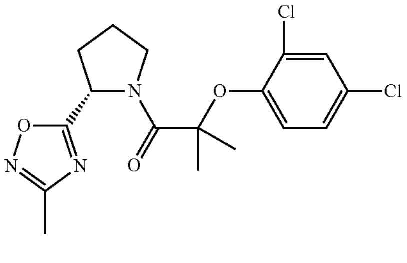 [SMILES: Cc1noc([C@@H]2CCCN2C(=O)C(C)(C)Oc2ccc(Cl)cc2Cl)n1] | QY-6-84 | 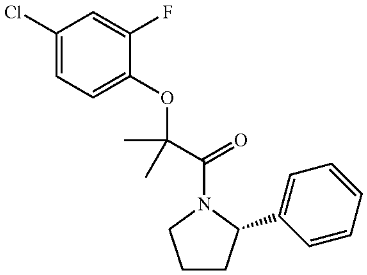 [SMILES: CC(C)(Oc1ccc(Cl)cc1F)C(=O)N1CCC[C@H]1c1ccccc1] |

-continued
| Compound number | Chemical structure | Compound number | Chemical structure |
|---|---|---|---|
| QY-3-86 | 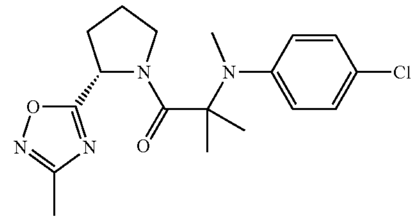 [SMILES: Cc1noc([C@@H]2CCCN2C(=O)C(C)(C)N(C)c2ccc(Cl)cc2)n1] | QY-7-7 | 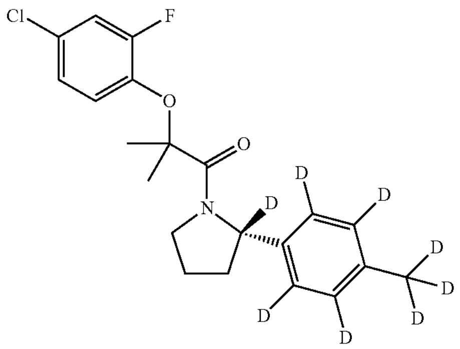 [SMILES: [2H]c1c([2H])c([C@]2([2H])CCCN2C(=O)C(C)(C)Oc2ccc(Cl)cc2F)c([2H])c([2H])c1C([2H])([2H])[2H]] |
| QY-3-94 | 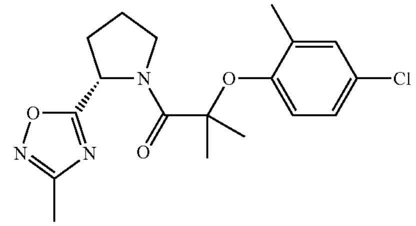 [SMILES: Cc1noc([C@@H]2CCCN2C(=O)C(C)(C)Oc2ccc(Cl)cc2C)n1] | QY-7-50 | 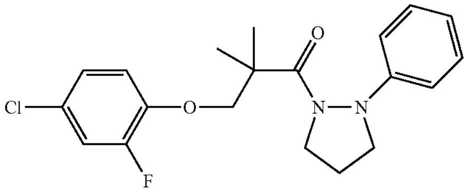 [SMILES: CC(C)(COc1ccc(Cl)cc1F)C(=O)N1CCCN1c1ccccc1] |
| QY-3-95 | 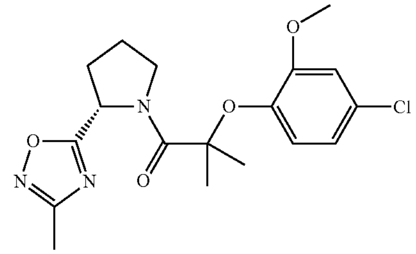 [SMILES: COc1cc(Cl)ccc1OC(C)(C)C(=O)N1CCC[C@H]1c1nc(C)no1] | QY-7-60 | 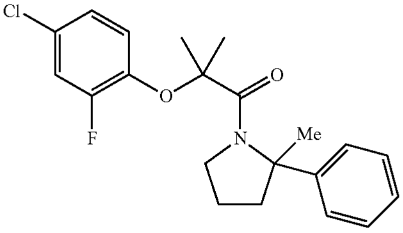 [SMILES: CC(C)(Oc1ccc(Cl)cc1F)C(=O)N1CCCC1(C)c1ccccc1] |
| QY-3-96 | 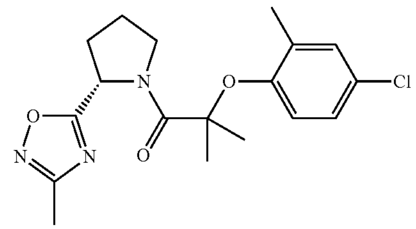 [SMILES: Cc1noc([C@@H]2CCCN2C(=O)C(C)(C)Oc2ccc(Cl)cc2C)n1] | QY-7-62 | 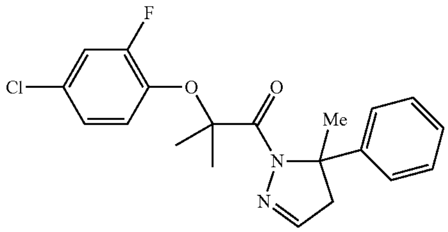 [SMILES: CC(C)(Oc1ccc(Cl)cc1F)C(=O)N1N=CCC1(C)c1ccccc1] |
| QY-3-99 | 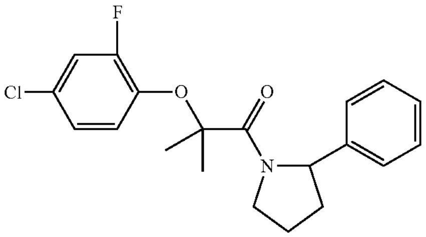 [SMILES: CC(C)(Oc1ccc(Cl)cc1F)C(=O)N1CCCC1c1ccccc1] | XHJ-3-22 | 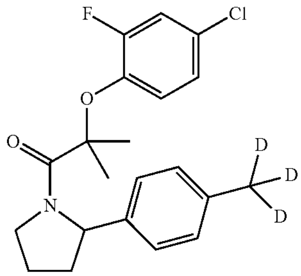 [SMILES: [2H]C([2H])([2H])c1ccc(C2CCCN2C(=O)C(C)(C)Oc2ccc(Cl)cc2F)cc1] |

-continued
| Compound number | Chemical structure | Compound number | Chemical structure |
|---|---|---|---|
| QY4-1 | 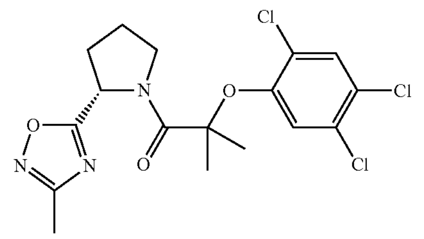 [SMILES: Cc1noc([C@@H]2CCCN2C(=O)C(C)(C)Oc2cc(Cl)c(Cl)cc2Cl)n1] | ZSQ-13-56 | 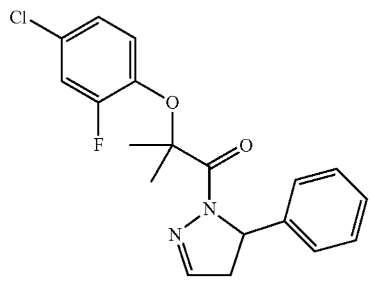 [SMILES: CC(C)(Oc1ccc(Cl)cc1F)C(=O)N1N=CCC1c1ccccc1] |
| QY4-2 | 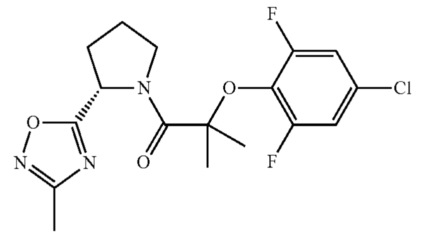 [SMILES: Cc1noc([C@@H]2CCCN2C(=O)C(C)(C)Oc2c(F)cc(Cl)cc2F)n1] | ZSQ-13-57 | 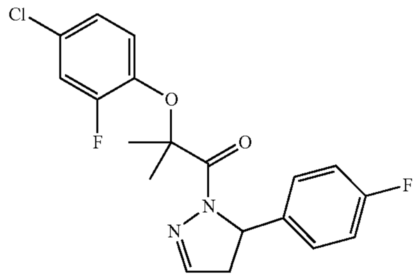 [SMILES: CC(C)(Oc1ccc(Cl)cc1F)C(=O)N1N=CCC1c1ccc(F)cc1] |
| QY-7-101 | 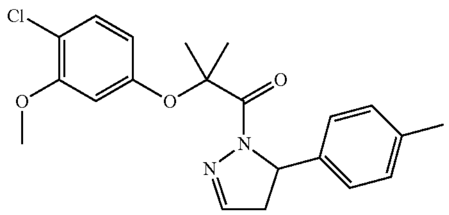 [SMILES: COc1cc(OC(C)(C)C(=O)N2N=CCC2c2ccc(C)cc2)ccc1Cl] | QY-8-101 | 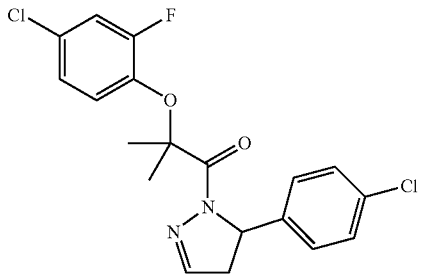 [SMILES: CC(C)(Oc1ccc(Cl)cc1F)C(=O)N1N=CCC1c1ccc(Cl)cc1] |
| QY-9-8 | 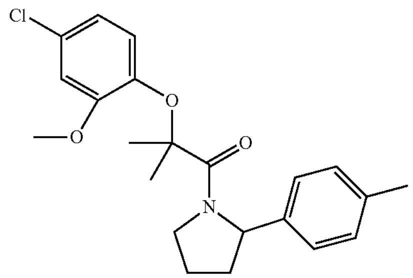 [SMILES: COc1cc(Cl)ccc1OC(C)(C)C(=O)N1CCCC1c1ccc(C)cc1] | QY-9-32 | 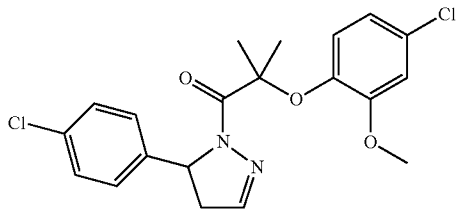 [SMILES: COc1cc(Cl)ccc1OC(C)(C)C(=O)N1N=CCC1c1ccc(Cl)cc1] |
| QY-9-43 | 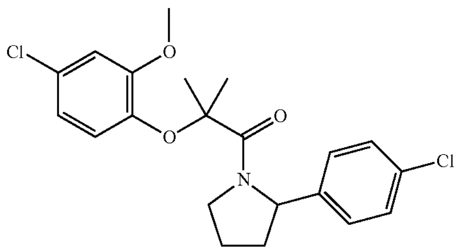 [SMILES: COc1cc(Cl)ccc1OC(C)(C)C(=O)N1CCCC1c1ccc(Cl)cc1] | QY-10-1 | 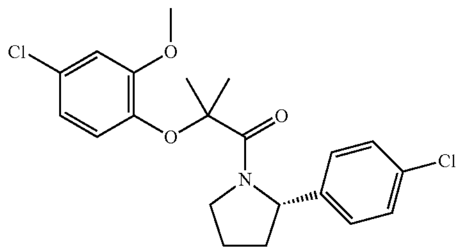 [SMILES: COc1cc(Cl)ccc1OC(C)(C)C(=O)N1CCC[C@H]1c1ccc(Cl)cc1] |

-continued
| Compound number | Chemical structure | Compound number | Chemical structure |
|---|---|---|---|
| QY-10-92 | 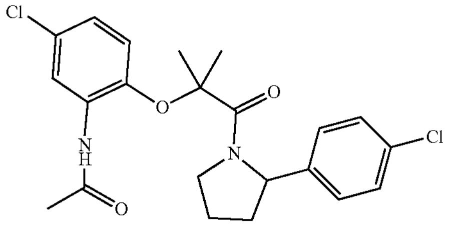 [SMILES: CC(=O)Nc1cc(Cl)ccc1OC(C)(C)C(=O)N1CCCC1c1ccc(Cl)cc1] | QY-10-96 | 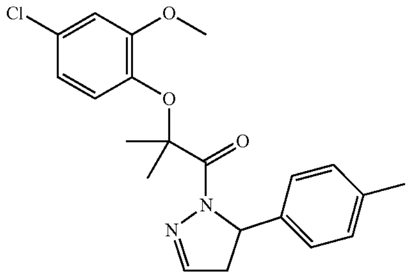 [SMILES: COc1cc(Cl)ccc1OC(C)(C)C(=O)N1N=CCC1c1ccc(C)cc1] |
| QY-10-104 | 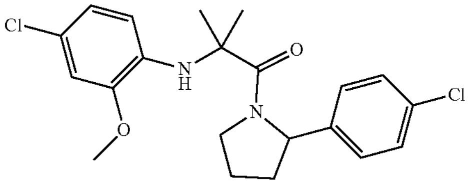 [SMILES: COc1cc(Cl)ccc1NC(C)(C)C(=O)N1CCCC1c1ccc(Cl)cc1] | QY-11-1 | 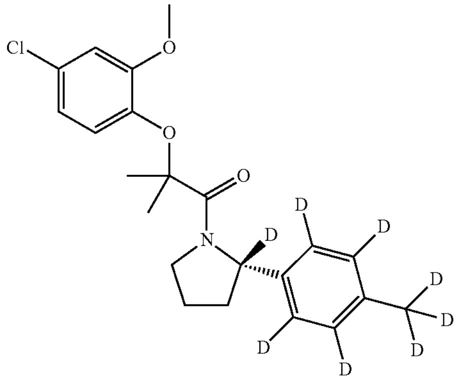 [SMILES: [2H]c1c([2H])c([C@]2([2H])CCCN2C(=O)C(C)(C)Oc2ccc(Cl)cc2OC)c([2H])c([2H])c1C([2H])([2H])[2H]] |
| QY-11-9A | 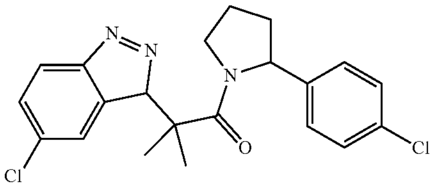 [SMILES: CC(C)(C(=O)N1CCCC1c1ccc(Cl)cc1)C1N=Nc2ccc(Cl)cc21] | QY-11-9B | 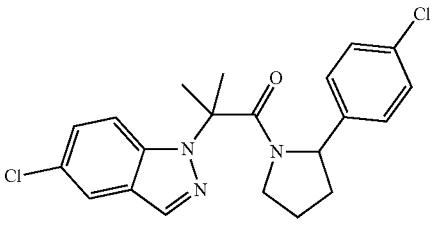 [SMILES: CC(C)(C(=O)N1CCCC1c1ccc(Cl)cc1)n1ncc2cc(Cl)ccc21] |
| QY-11-11A | 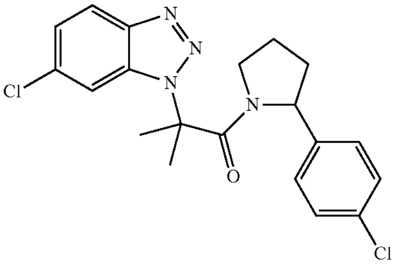 [SMILES: CC(C)(C(=O)N1CCCC1c1ccc(Cl)cc1)n1nnc2ccc(Cl)cc21] | QY-11-11B | 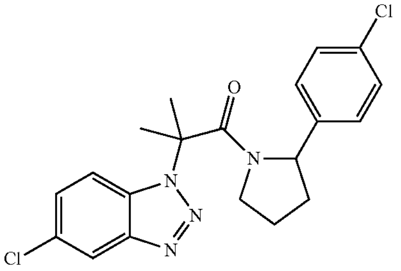 [SMILES: CC(C)(C(=O)N1CCCC1c1ccc(Cl)cc1)n1nnc2cc(Cl)ccc21] |
| QY-11-15B | 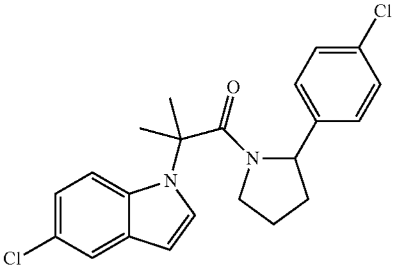 [SMILES: CC(C)(C(=O)N1CCCC1c1ccc(Cl)cc1)n1ccc2cc(Cl)ccc21] | QY-11-16A | 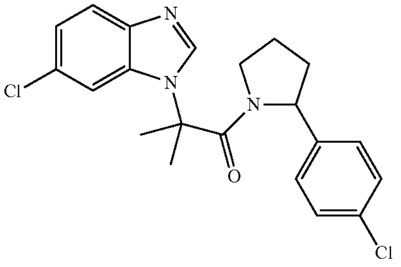 [SMILES: CC(C)(C(=O)N1CCCC1c1ccc(Cl)cc1)n1cnc2ccc(Cl)cc21] |

-continued
| Compound number | Chemical structure | Compound number | Chemical structure |
|---|---|---|---|
| QY-11-16B | 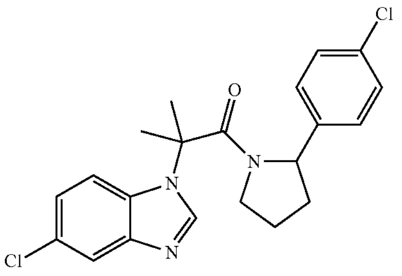 [SMILES: CC(C)(C(=O)N1CCCC1c1ccc(Cl)cc1)n1cnc2cc(Cl)ccc21] | QY-11-36 | 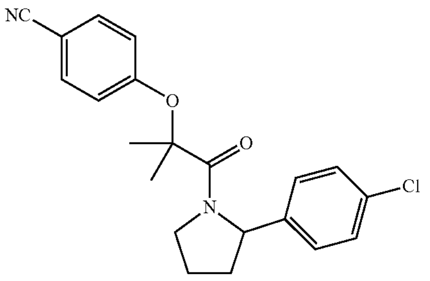 [SMILES: CC(C)(Oc1ccc(C#N)cc1)C(=O)N1CCCC1c1ccc(Cl)cc1] |
| QY-11-44 | 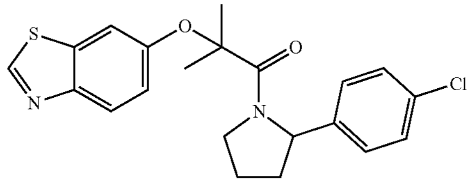 [SMILES: CC(C)(Oc1ccc2ncsc2c1)C(=O)N1CCCC1c1ccc(Cl)cc1] | QY-11-45 | 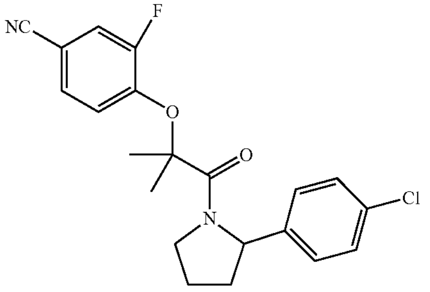 [SMILES: CC(C)(Oc1ccc(C#N)cc1F)C(=O)N1CCCC1c1ccc(Cl)cc1] |
| QY-12-11 | 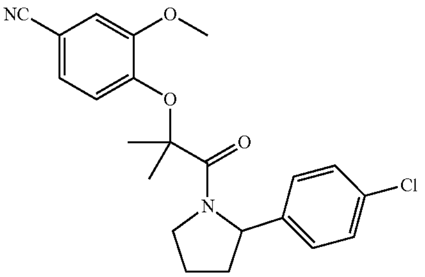 [SMILES: COc1cc(C#N)ccc1OC(C)(C)C(=O)N1CCCC1c1ccc(Cl)cc1] | QY-12-14 | 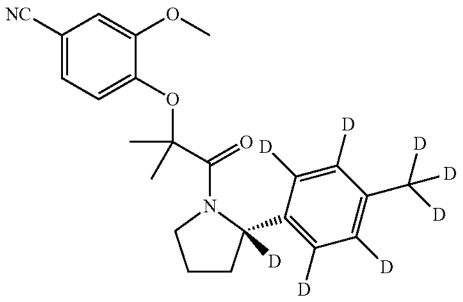 [SMILES: [2H]c1c([2H])c([C@]2([2H])CCCN2C(=O)C(C)(C)Oc2ccc(C#N)cc2OC)c([2H])c([2H])c1C([2H])([2H])[2H]] |
| QY-12-32 | 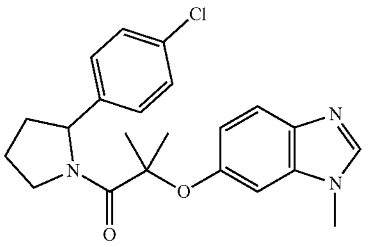 [SMILES: Cn1cnc2ccc(OC(C)(C)C(=O)N3CCCC3c3ccc(Cl)cc3)cc21] | QY-13-42 | 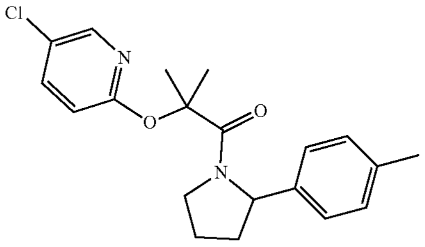 [SMILES: Cc1ccc(C2CCCN2C(=O)C(C)(C)Oc2ccc(Cl)cn2)cc1] |
| QY-13-68 | 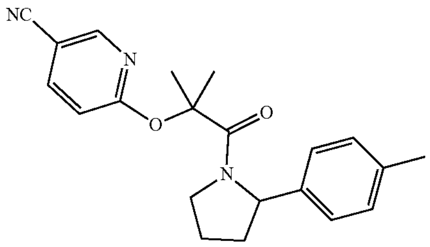 [SMILES: Cc1ccc(C2CCCN2C(=O)C(C)(C)Oc2ccc(C#N)cn2)cc1] | QY-13-70 | 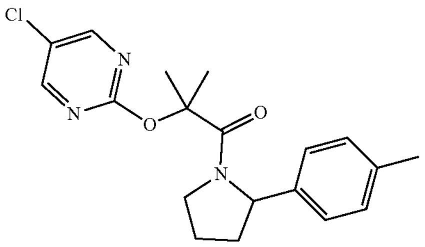 [SMILES: Cc1ccc(C2CCCN2C(=O)C(C)(C)Oc2ncc(Cl)cn2)cc1] |

-continued
| Compound number | Chemical structure | Compound number | Chemical structure |
| --- | --- | --- | --- |
| QY-13-86 | 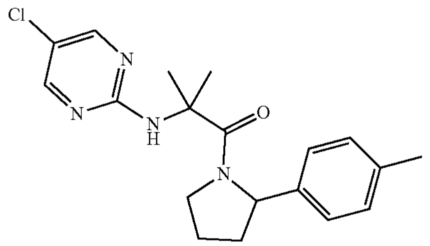 [SMILES: Cc1ccc(C2CCCN2C(=O)C(C)(C)Nc2ncc(Cl)cn2)cc1] | QY-14-8 | 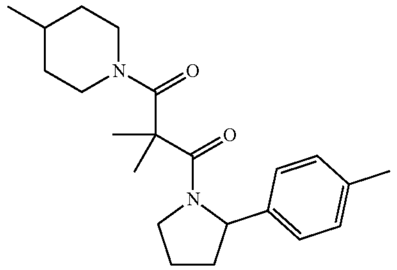 |
| QY-14-9 | 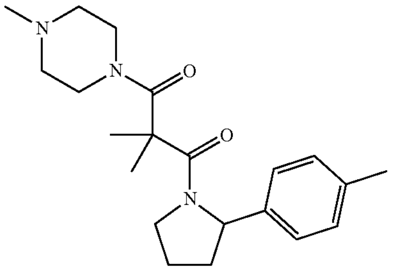 | QY-14-17 | 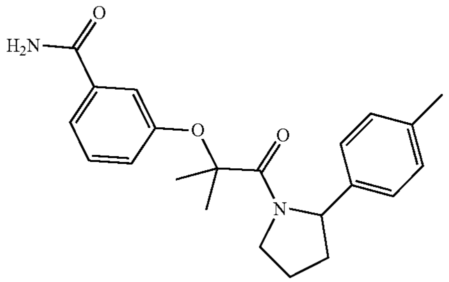 [SMILES: Cc1ccc(C2CCCN2C(=O)C(C)(C)Oc2cccc(C(N)=O)c2)cc1] |
| QY-14-24 | 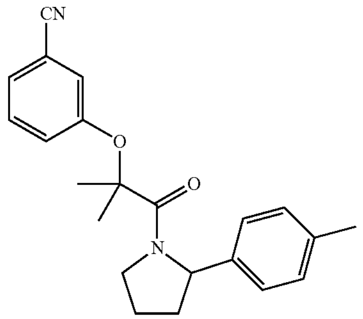 [SMILES: Cc1ccc(C2CCCN2C(=O)C(C)(C)Oc2cccc(C#N)c2)cc1] | QY-14-25 | 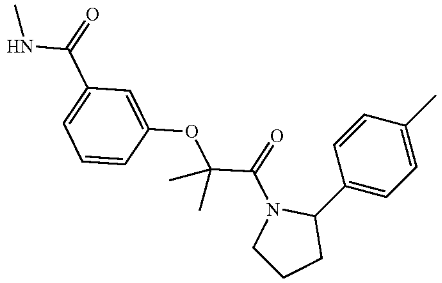 |
| QY-14-27 | 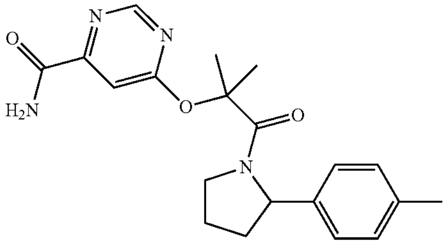 [SMILES: Cc1ccc(C2CCCN2C(=O)C(C)(C)Oc2cc(C(N)=O)ncn2)cc1] | QY-14-29 | 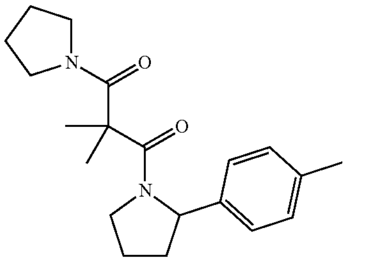 [SMILES: Cc1ccc(C2CCCN2C(=O)C(C)(C)C(=O)N2CCCC2)cc1] |
| QY-14-30 | 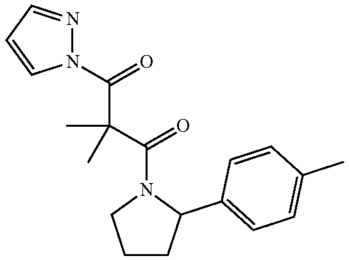 [SMILES: Cc1ccc(C2CCCN2C(=O)C(C)(C)C(=O)n2cccn2)cc1] | QY-14-31 | 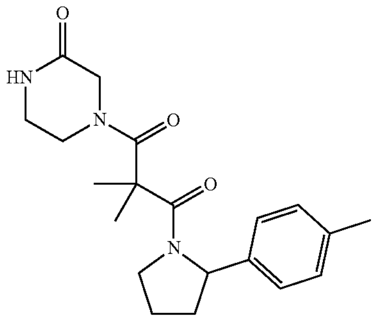 [SMILES: Cc1ccc(C2CCCN2C(=O)C(C)(C)C(=O)N2CCNC(=O)C2)cc1] |

-continued
| Compound number | Chemical structure | Compound number | Chemical structure |
| --- | --- | --- | --- |
| QY-14-33 | 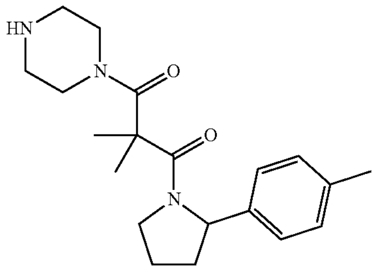 [SMILES: Cc1ccc(C2CCCN2C(=O)C(C)(C)C(=O)N2CCNCC2)cc1] | QY-14-34 | 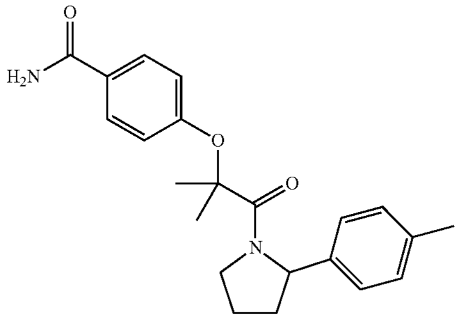 [SMILES: Cc1ccc(C2CCCN2C(=O)C(C)(C)Oc2ccc(C(N)=O)cc2)cc1] |
| QY-14-35 | 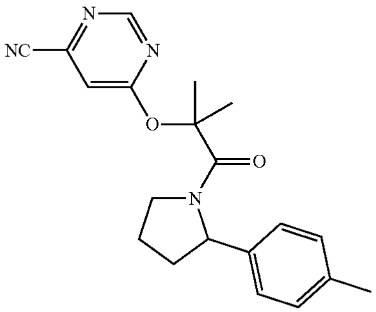 [SMILES: Cc1ccc(C2CCCN2C(=O)C(C)(C)Oc2cc(C#N)ncn2)cc1] | QY-14-40 | 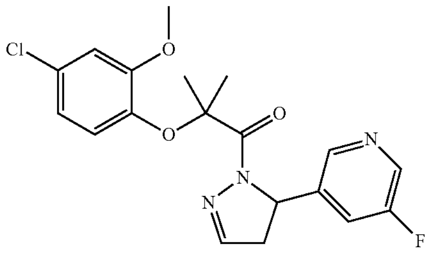 [SMILES: COc1cc(Cl)ccc1OC(C)(C)C(=O)N1N=CCC1c1cncc(F)c1] |
| QY-14-44 | 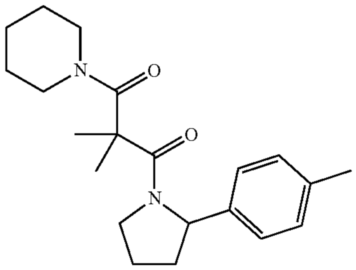 [SMILES: Cc1ccc(C2CCCN2C(=O)C(C)(C)C(=O)N2CCCCC2)cc1] | QY-14-59 | 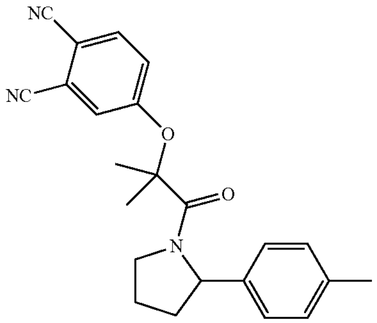 [SMILES: Cc1ccc(C2CCCN2C(=O)C(C)(C)Oc2ccc(C#N)c(C#N)c2)cc1] |
| QY-14-60 | 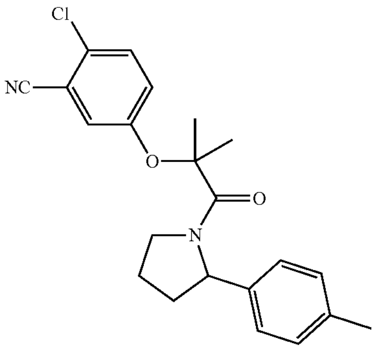 [SMILES: Cc1ccc(C2CCCN2C(=O)C(C)(C)Oc2ccc(Cl)c(C#N)c2)cc1] | QY-14-68 | 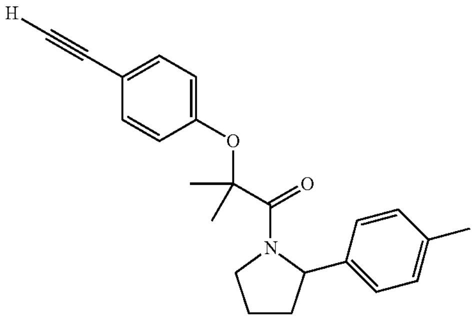 [SMILES: C#Cc1ccc(OC(C)(C)C(=O)N2CCCC2c2ccc(C)cc2)cc1] |

-continued
| Compound number | Chemical structure | Compound number | Chemical structure |
|---|---|---|---|
| QY-15-11 | 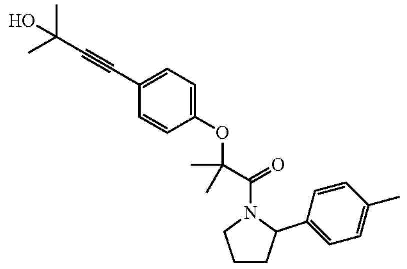 [SMILES: Cc1ccc(C2CCCN2C(=O)C(C)(C)Oc2ccc(C#CC(C)(C)O)cc2)cc1] | QY-15-12 | 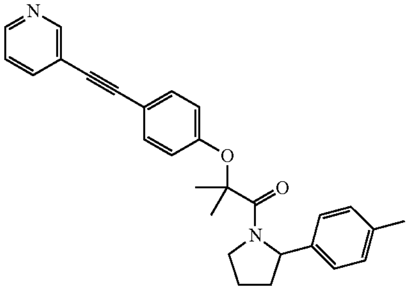 [SMILES: Cc1ccc(C2CCCN2C(=O)C(C)(C)Oc2ccc(C#Cc3cccnc3)cc2)cc1] |
| QY-15-31 | 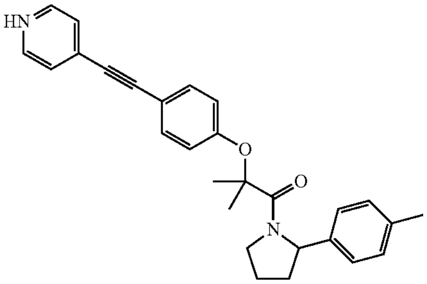 [SMILES: Cc1ccc(C2CCCN2C(=O)C(C)(C)Oc2ccc(C#Cc3ccncc3)cc2)cc1] | QY-16-60 | 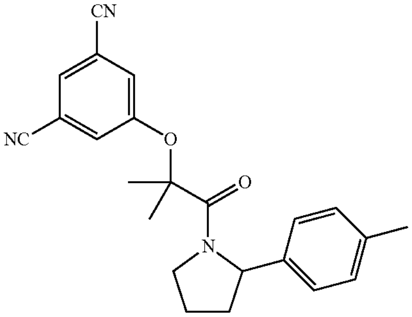 [SMILES: Cc1ccc(C2CCCN2C(=O)C(C)(C)Oc2cc(C#N)cc(C#N)c2)cc1] |
| QY-16-61 | 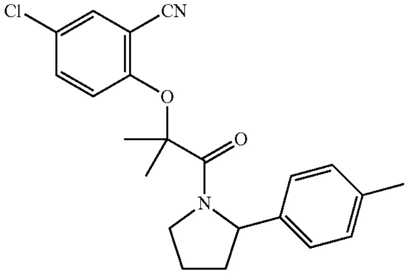 [SMILES: Cc1ccc(C2CCCN2C(=O)C(C)(C)Oc2ccc(Cl)cc2C#N)cc1] | QY-16-66 | 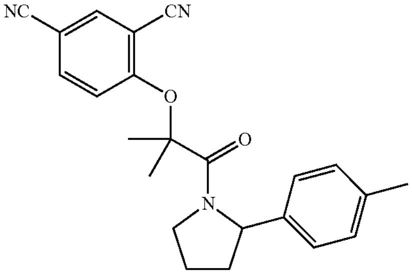 [SMILES: Cc1ccc(C2CCCN2C(=O)C(C)(C)Oc2ccc(C#N)cc2C#N)cc1] |
| QY-16-75 | 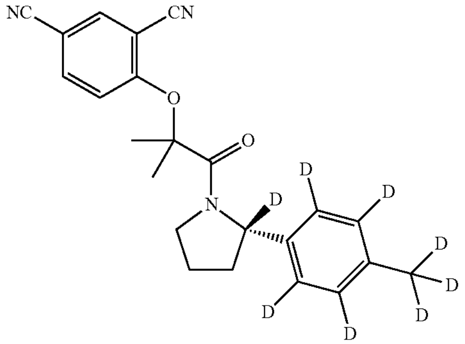 [SMILES: [2H]c1c([2H])c([C@]2([2H])CCCN2C(=O)C(C)(C)Oc2ccc(C#N)cc2C#N)c([2H])c([2H])c1C([2H])([2H])[2H]] | QY-16-76 | 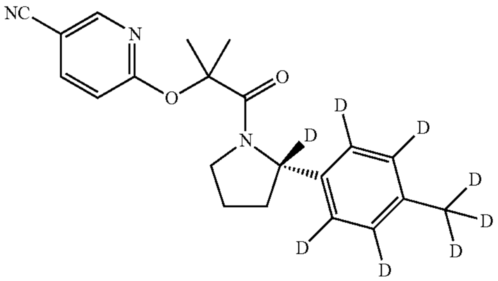 [SMILES: [2H]c1c([2H])c([C@]2([2H])CCCN2C(=O)C(C)(C)Oc2ccc(C#N)cn2)c([2H])c([2H])c1C([2H])([2H])[2H]] |
| QY-16-77 | 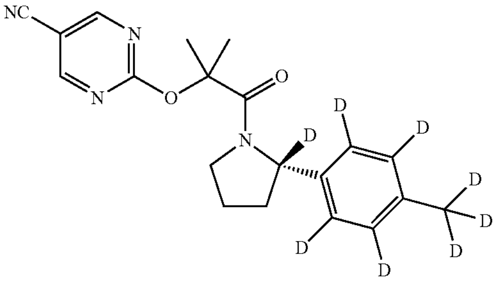 [SMILES: [2H]c1c([2H])c([C@]2([2H])CCCN2C(=O)C(C)(C)Oc2ncc(C#N)cn2)c([2H])c([2H])c1C([2H])([2H])[2H]] | QY-16-82 | 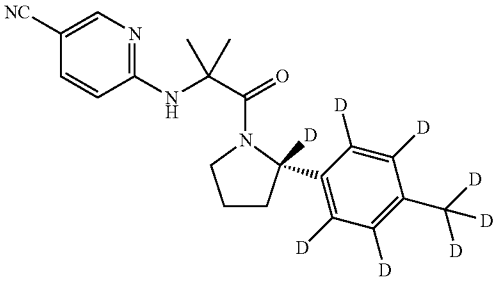 [SMILES: [2H]c1c([2H])c([C@]2([2H])CCCN2C(=O)C(C)(C)Nc2ccc(C#N)cn2)c([2H])c([2H])c1C([2H])([2H])[2H]] |

-continued

| Compound number | Chemical structure | Compound number | Chemical structure |
| --- | --- | --- | --- |
| QY-16-84 | 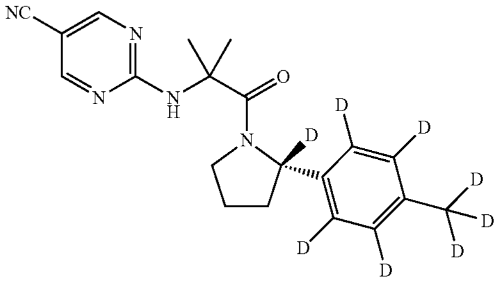 [SMILES: [2H]c1c([2H])c([C@]2([2H])CCCN2C(=O)C(C)(C)Nc2ncc(C#N)cn2)c([2H])c([2H])c1C([2H])([2H])[2H]] | | |

Compound Test Data:

QY-1-98

$^1$H NMR (400 MHz, DMSO-d6) δ 7.36-7.21 (m, 2H), 6.99-6.84 (m, 2H), 5.29-5.21 (m, 1H), 3.81-3.66 (m, 2H), 2.34 (d, J=2.1 Hz, 3H), 2.25-2.16 (m, 1H), 1.92 (m, 2H), 1.83-1.75 (m, 1H), 1.50 (s, 3H), 1.46 (s, 3H); ESI-MS m/z 350.1 $(M+H)^+$.

QY-2-25

$^1$H NMR (400 MHz, DMSO-d6) δ 7.32-7.24 (m, 2H), 7.00 (t, J=7.3 Hz, 1H), 6.87 (m, 2H), 5.25 (dd, J=8.4, 4.5 Hz, 1H), 3.82-3.72 (m, 2H), 2.33 (s, 3H), 2.23-2.16 (m, 1H), 1.90 (m, 2H), 1.82-1.74 (m, 1H), 1.50 (s, 3H), 1.45 (s, 3H); ESI-MS m/z 316.1 $(M+H)^+$.

QY-2-26

$^1$H NMR (400 MHz, DMSO-d6) δ 7.10 (m, 2H), 6.95-6.87 (m, 2H), 5.25 (d, J=3.9 Hz, 1H), 3.79 (m, 2H), 2.33 (d, J=4.9 Hz, 3H), 2.26-2.18 (m, 1H), 1.99-1.90 (m, 2H), 1.82-1.75 (m, 1H), 1.48 (s, 3H), 1.42 (s, 3H); ESI-MS m/z 334.1 $(M+H)^+$.

QY-2-27

$^1$H NMR (400 MHz, DMSO-d6) δ 6.89 (m, 4H), 5.25 (dd, J=8.4, 4.5 Hz, 1H), 3.83 (m, 2H), 2.95 (m, 6H), 2.35 (s, 3H), 2.28-2.20 (m, 1H), 2.00-1.89 (m, 2H), 1.80 (m, 1H), 1.46 (s, 3H), 1.41 (s, 3H); ESI-MS m/z 359.2 $(M+H)^+$.

QY-2-34

$^1$H NMR (400 MHz, DMSO-d6) δ 7.55 (s, 2H), 7.33-7.26 (m, 2H), 6.86-6.78 (m, 2H), 5.26 (dd, J=7.9, 3.4 Hz, 1H), 3.60-3.51 (m, 2H), 2.11 (dd, J=7.1, 3.7 Hz, 1H), 2.04-1.87 (m, 2H), 1.83 (m, 1H), 1.50 (s, 6H); ESI-MS m/z 367.1 $(M+H)^+$.

QY-2-38 $^1$H NMR (400 MHz, DMSO-d6) δ 7.33-7.26 (m, 2H), 6.86-6.80 (m, 2H), 5.27 (dd, J=8.0, 2.5 Hz, 1H), 3.67 (t, J=6.6 Hz, 2H), 2.29 (s, 3H), 2.20 (s, 3H), 2.07-2.00 (m, 1H), 1.89 (m, 2H), 1.80 (m, 1H), 1.52 (s, 3H), 1.49 (s, 3H); ESI-MS m/z 379.0 $(M+H)^+$.

QY-2-39

$^1$H NMR (400 MHz, DMSO-d6) δ 7.71 (d, J=3.2 Hz, 1H), 7.60 (d, J=3.2 Hz, 1H), 7.34-7.27 (m, 2H), 6.90-6.81 (m, 2H), 5.43 (dd, J=8.1, 2.7 Hz, 1H), 3.70 (dd, J=9.5, 4.6 Hz, 2H), 2.17-2.07 (m, 1H), 1.98 (m, 2H), 1.87-1.81 (m, 1H), 1.53 (s, 3H), 1.50 (s, 3H); ESI-MS m/z 351.1 $(M+H)^+$.

QY-2-52

$^1$H NMR (400 MHz, DMSO-d6) δ 7.35-7.25 (m, 2H), 7.11 (m, 1H), 6.90-6.78 (m, 2H), 5.35 (m, 1H), 3.69 (t, J=6.3 Hz, 2H), 2.30 (m, 3H), 2.14-2.04 (m, 1H), 1.97-1.87 (m, 2H), 1.80 (dd, J=13.0, 6.6 Hz, 1H), 1.52 (s, 3H), 1.50 (s, 3H); ESI-MS m/z 365.1 $(M+H)^+$.

QY-2-53

$^1$H NMR (400 MHz, DMSO-d6) δ 7.33-7.26 (m, 2H), 6.79 (m, 2H), 5.99 (s, 1H), 5.22 (dd, J=8.2, 3.1 Hz, 1H), 3.65 (d, J=3.0 Hz, 2H), 2.20 (s, 3H), 2.00 (m, 2H), 1.88-1.80 (m, 2H), 1.52 (s, 3H), 1.49 (s, 3H); ESI-MS m/z 349.1 $(M+H)^+$.

QY-2-54

$^1$H NMR (400 MHz, DMSO-d6) δ 6.84 (m, 4H), 5.25 (dd, J=8.4, 4.4 Hz, 1H), 3.84 (td, J=6.8, 2.5 Hz, 2H), 3.71 (s, 3H), 2.34 (s, 3H), 2.28-2.20 (m, 1H), 2.00-1.90 (m, 2H), 1.85-1.77 (m, 1H), 1.44 (s, 3H), 1.39 (s, 3H); ESI-MS m/z 346.2 $(M+H)^+$.

QY-2-55

$^1$H NMR (400 MHz, DMSO-d6) δ 7.81-7.72 (m, 2H), 7.03-6.94 (m, 2H), 5.24 (dd, J=8.4, 4.7 Hz, 1H), 3.72-3.56 (m, 2H), 2.34 (s, 3H), 2.21-2.14 (m, 1H), 1.88 (m, 2H), 1.79-1.72 (m, 1H), 1.57 (s, 3H), 1.52 (s, 3H); ESI-MS m/z 341.1 $(M+H)^+$.

QY-2-56

$^1$H NMR (400 MHz, DMSO-d6) δ 7.65-7.56 (m, 4H), 7.44 (t, J=7.7 Hz, 2H), 7.33 (m, 1H), 6.99-6.93 (m, 2H), 5.27 (dd, J=8.4, 4.5 Hz, 1H), 3.84-3.73 (m, 2H), 2.34 (s, 3H), 2.25-2.16 (m, 1H), 1.92 (m, 2H), 1.84-1.76 (m, 1H), 1.54 (s, 3H), 1.50 (s, 3H); ESI-MS m/z 392.1 $(M+H)^+$.

QY-2-75

$^1$H NMR (400 MHz, DMSO-d6) δ 7.58 (d, J=8.9 Hz, 2H), 6.69 (d, J=8.9 Hz, 2H), 5.24 (dd, J=8.4, 4.5 Hz, 1H), 3.71 (m, 2H), 2.33 (s, 3H), 2.20 (m, 1H), 1.91 (m, 2H), 1.82-1.74 (m, 1H), 1.50 (s, 3H), 1.46 (s, 3H); ESI-MS m/z 442.0 $(M+H)^+$.

QY-2-76

$^1$H NMR (400 MHz, DMSO-d6) δ 7.32-7.24 (m, 2H), 6.96 (d, J=9.1 Hz, 2H), 5.25 (dd, J=8.5, 4.5 Hz, 1H), 3.81-3.68 (m, 2H), 2.33 (s, 3H), 2.24-2.17 (m, 1H), 1.97-1.88 (m, 2H), 1.82-1.76 (m, 1H), 1.51 (s, 3H), 1.47 (s, 3H); ESI-MS m/z 400.1 $(M+H)^+$.

QY-2-77

$^1$H NMR (400 MHz, DMSO-d6) δ 7.06 (d, J=8.2 Hz, 2H), 6.80-6.73 (m, 2H), 5.26-5.22 (m, 1H), 3.77 (d, J=4.9 Hz, 2H), 2.34 (s, 3H), 2.24 (s, 3H), 2.21-2.16 (m, 1H), 1.98-1.87 (m, 2H), 1.79 (m, 1H), 1.47 (s, 3H), 1.42 (s, 3H); ESI-MS m/z 330.2 $(M+H)^+$.

QY-2-78

$^1$H NMR (400 MHz, DMSO-d6) δ 7.37 (m, 2H), 7.11 (d, J=7.4 Hz, 1H), 6.98-6.95 (m, 2H), 6.95-6.90 (m, 4H), 5.25 (d, J=4.0 Hz, 1H), 3.83 (d, J=6.7 Hz, 2H), 2.29 (s, 3H), 2.26-2.20 (m, 1H), 2.00-1.91 (m, 2H), 1.85-1.77 (m, 1H), 1.49 (s, 3H), 1.44 (s, 3H); ESI-MS m/z 408.2 $(M+H)^+$.

QY-2-79

$^1$H NMR (400 MHz, DMSO-d6) δ 7.31 (t, J=8.2 Hz, 1H), 7.08 (m, 1H), 6.91 (t, J=2.2 Hz, 1H), 6.84 (m, 1H), 5.24 (dd, J=8.4, 4.9 Hz, 1H), 3.79 (s, 1H), 3.68 (s, 1H), 2.33 (s, 3H), 2.26-2.18 (m, 1H), 1.97-1.88 (m, 2H), 1.78 (m, 1H), 1.53 (s, 3H), 1.45 (s, 3H); ESI-MS m/z 350.1 $(M+H)^+$.

QY-2-100 $^1$H NMR (400 MHz, $CDCl_3$) δ 7.25-7.19 (m, 2H), 6.86-6.80 (m, 2H), 5.28 (dd, J=8.8, 4.5 Hz, 1H), 3.85-3.75 (m, 2H), 2.24-2.14 (m, 1H), 2.11-2.01 (m, 2H), 1.94-1.88 (m, 2H), 1.58 (s, 3H), 1.56 (s, 3H), 1.09-0.99 (m, 4H); ESI-MS m/z 376.1 $(M+H)^+$.

QY-2-103

$^1$H NMR (400 MHz, DMSO-d6) δ 7.36-7.26 (m, 2H), 6.94-6.85 (m, 2H), 5.24 (m, 1H), 3.72 (m, 2H), 2.73-2.67 (m, 2H), 2.21 (m, 1H), 1.96-1.86 (m, 2H), 1.81-1.73 (m, 1H), 1.67-1.59 (m, 2H), 1.50 (s, 3H), 1.45 (s, 3H), 1.34 (m, 2H), 0.90 (t, J=7.4 Hz, 3H); ESI-MS m/z 392.1 $(M+H)^+$.

QY-2-104

$^1$H NMR (400 MHz, DMSO-d6) δ 7.37-7.22 (m, 5H), 7.18-7.13 (m, 2H), 6.86-6.78 (m, 2H), 5.23 (dd, J=8.3, 5.2 Hz, 1H), 4.11 (s, 2H), 3.75 (s, 1H), 3.63 (s, 1H), 2.20 (m, 1H), 1.89 (d, J=5.6 Hz, 2H), 1.79-1.71 (m, 1H), 1.49 (s, 3H), 1.41 (s, 3H); ESI-MS m/z 426.1 $(M+H)^+$.

QY-3-4

$^1$H NMR (400 MHz, DMSO-d6) δ 7.32-7.29 (m, 2H), 6.95-6.89 (m, 2H), 5.18 (dd, J=8.4, 3.8 Hz, 1H), 4.85 (s, 2H), 3.79-3.61 (m, 2H), 2.32 (d, J=7.0 Hz, 1H), 2.30 (s, 3H), 2.08-2.01 (m, 2H), 1.95 (m, 1H); ESI-MS m/z 321.9 $(M+H)^+$.

QY-3-11

$^1$H NMR (400 MHz, DMSO-d6) δ 7.33-7.27 (m, 2H), 6.86-6.79 (m, 2H), 5.97 (d, J=0.7 Hz, 1H), 5.14 (dd, J=8.1, 3.2 Hz, 1H), 3.66 (s, 2H), 2.37 (d, J=0.6 Hz, 3H), 2.02 (m, 1H), 1.89-1.72 (m, 3H), 1.51 (s, 3H), 1.49 (s, 3H); ESI-MS m/z 349.1 $(M+H)^+$.

QY-3-17

$^1$H NMR (400 MHz, DMSO-d6) δ 7.35-7.25 (m, 2H), 6.94-6.86 (m, 2H), 5.25 (dd, J=8.4, 4.8 Hz, 1H), 3.75 (s, 2H), 3.11-3.01 (m, 1H), 2.25-2.16 (m, 1H), 1.96-1.87 (m, 2H), 1.77 (m, 1H), 1.50 (s, 3H), 1.46 (s, 3H), 1.27 (d, J=1.3 Hz, 3H), 1.25 (d, J=1.3 Hz, 3H); ESI-MS m/z 378.1 $(M+H)^+$.

QY-3-26

$^1$H NMR (400 MHz, DMSO-d6) δ 7.47 (t, J=8.9 Hz, 1H), 6.92 (m, 1H), 6.75 (m, 1H), 5.24 (dd, J=8.4, 4.9 Hz, 1H), 3.84-3.61 (m, 2H), 2.33 (s, 3H), 2.23 (dd, J=12.6, 8.3 Hz, 1H), 1.98-1.89 (m, 2H), 1.77 (m, 1H), 1.55 (s, 3H), 1.46 (s, 3H); ESI-MS m/z 368.2 $(M+H)^+$.

QY-3-27

$^1$H NMR (400 MHz, DMSO-d6) δ 7.51 (m, 1H), 7.16 (m, 1H), 7.03 (m, 1H), 5.26 (dd, J=8.5, 4.6 Hz, 1H), 3.86-3.74 (m, 2H), 2.34 (s, 3H), 2.27-2.18 (m, 1H), 1.96 (m, 2H), 1.85-1.77 (m, 1H), 1.52 (s, 3H), 1.46 (s, 3H); ESI-MS m/z 368.2 $(M+H)^+$.

QY-3-28

$^1$H NMR (400 MHz, DMSO-d6) δ 7.86 (d, J=8.1 Hz, 2H), 7.77 (d, J=8.0 Hz, 1H), 7.51-7.45 (m, 1H), 7.39 (m, 1H), 7.20-7.13 (m, 2H), 5.28 (dd, J=8.3, 5.2 Hz, 1H), 3.91-3.63 (m, 2H), 2.35 (s, 3H), 2.24-2.16 (m, 1H), 1.94-1.86 (m, 2H), 1.75 (m, 1H), 1.60 (s, 3H), 1.52 (s, 3H); ESI-MS m/z 366.1 $(M+H)^+$.

QY-3-29

$^1$H NMR (400 MHz, DMSO-d6) δ 7.29 (m, 5H), 7.11-7.05 (m, 2H), 6.84-6.74 (m, 2H), 5.06 (dd, J=8.1, 4.2 Hz, 1H), 3.84-3.67 (m, 2H), 2.09 (m, 1H), 1.87-1.57 (m, 3H), 1.56 (s, 3H), 1.48 (s, 3H); ESI-MS m/z 344.1 $(M+H)^+$.

QY-3-35

$^1$H NMR (400 MHz, DMSO-d6) δ 7.42-7.31 (m, 2H), 7.01-6.86 (m, 2H), 5.13 (dd, J=8.0, 5.5 Hz, 1H), 3.77 (m, 2H), 2.25 (s, 3H), 2.09 (m, 1H), 2.02-1.95 (m, 2H), 1.78 (d, J=6.6 Hz, 1H), 1.38-1.30 (m, 2H), 1.23 (m, 2H); ESI-MS m/z 348.2 $(M+H)^+$.

QY-3-36

$^1$H NMR (400 MHz, DMSO-d6) δ 7.39 (m, 4H), 5.15 (dd, J=7.9, 4.6 Hz, 1H), 4.16 (s, 2H), 2.32 (s, 3H), 2.31-2.23 (m, 1H), 2.09 (s, 2H), 1.85 (m, 1H), 1.43 (s, 3H), 1.39 (s, 3H); ESI-MS m/z 366.1 $(M+H)^+$.

QY-3-39

$^1$H NMR (400 MHz, DMSO-d6) δ 7.34-7.24 (m, 2H), 7.16 (m, 1H), 7.01 (m, 1H), 6.90-6.76 (m, 4H), 5.02 (dd, J=8.1, 4.3 Hz, 1H), 3.82 (m, 2H), 2.25 (s, 3H), 2.07 (s, 1H), 1.71 (m, 2H), 1.67-1.55 (m, 1H), 1.56-1.53 (s, 3H), 1.50 (s, 3H); ESI-MS m/z 358.1 $(M+H)^+$.

QY-3-46

$^1$H NMR (400 MHz, DMSO-d6) δ 7.33-7.24 (m, 2H), 6.87-6.76 (m, 2H), 5.19 (m, 1H), 3.66 (d, J=3.7 Hz, 2H), 2.31 (s, 3H), 2.27-1.87 (m, 7H), 1.63 (d, J=5.7 Hz, 5H); ESI-MS m/z 376.1 $(M+H)^+$.

QY-3-51

$^1$H NMR (400 MHz, DMSO-d6) δ 7.40-7.31 (m, 2H), 6.89-6.83 (m, 2H), 5.34 (dd, J=8.5, 4.7 Hz, 1H), 4.62 (s, 2H), 3.80-3.70 (m, 2H), 3.19 (s, 4H), 2.29-2.20 (m, 1H), 1.94 (m, 3H), 1.51 (s, 3H), 1.48 (s, 3H), 1.25 (t, J=5.9 Hz, 6H); ESI-MS m/z 421.2 $(M+H)^+$.

QY-3-65

$^1$H NMR (400 MHz, DMSO-d6) δ 7.37-7.28 (m, 2H), 6.93-6.86 (m, 2H), 5.35 (dd, J=8.7, 4.2 Hz, 1H), 3.80-3.70 (m, 2H), 3.04 (s, 3H), 2.98 (s, 3H), 2.28-2.20 (m, 1H), 2.00-1.88 (m, 3H), 1.51 (s, 3H), 1.45 (s, 3H); ESI-MS m/z 407.1 $(M+H)^+$.

QY-3-81

$^1$H NMR (400 MHz, DMSO-d6) δ 7.65 (d, J=2.6 Hz, 1H), 7.30 (dd, J=8.9, 2.6 Hz, 1H), 6.97 (d, J=8.9 Hz, 1H), 5.26 (m, 1H), 3.74 (m, 2H), 2.34 (s, 3H), 2.23 (m, 1H), 1.93 (m, 2H), 1.83-1.76 (m, 1H), 1.55 (s, 3H), 1.48 (s, 3H); ESI-MS m/z 384.0 $(M+H)^+$.

QY-3-86

$^1$H NMR (400 MHz, DMSO-d6) δ 7.22-7.14 (m, 2H), 6.83-6.75 (m, 2H), 5.15 (dd, J=8.4, 4.3 Hz, 1H), 3.64-3.54 (m, 2H), 2.85 (s, 3H), 2.31 (s, 3H), 2.15-2.06 (m, 1H), 1.96-1.73 (m, 3H), 1.33 (s, 6H); ESI-MS m/z 363.2 $(M+H)^+$.

QY-3-94 $^1$H NMR (400 MHz, DMSO-d6) δ 7.32-7.24 (m, 1H), 7.09 (dd, J=8.8, 2.7 Hz, 1H), 6.72 (d, J=8.8 Hz, 1H), 5.25 (dd, J=8.5, 4.6 Hz, 1H), 3.76-3.65 (m, 2H), 2.34 (s, 3H), 2.18 (s, 3H), 2.05-1.94 (m, 1H), 1.94-1.84 (m, 2H), 1.82-1.73 (m, 1H), 1.51 (s, 3H), 1.45 (s, 3H); ESI-MS m/z 364.1 $(M+H)^+$.

QY-3-95

$^1$H NMR (400 MHz, DMSO-d6) δ 7.09 (d, J=2.1 Hz, 1H), 6.87-6.81 (m, 2H), 5.25 (dd, J=8.5, 4.4 Hz, 1H), 3.82-3.74 (m, 5H), 2.33 (s, 3H), 2.26-2.17 (m, 1H), 1.97-1.78 (m, 3H), 1.44 (s, 3H), 1.42 (s, 3H); ESI-MS m/z 380.1 $(M+H)^+$.

QY-3-96

$^1$H NMR (400 MHz, DMSO-d6) δ 7.88 (d, J=2.6 Hz, 1H), 7.34 (dd, J=8.8, 2.6 Hz, 1H), 6.83 (d, J=8.8 Hz, 1H), 5.25 (dd, J=8.5, 4.7 Hz, 1H), 3.79-3.63 (m, 2H), 2.50 (s, 3H), 2.34 (s, 3H), 2.26-2.17 (m, 1H), 1.93 (m, 2H), 1.78 (m, 1H), 1.56 (s, 3H), 1.48 (s, 3H); ESI-MS m/z 364.1 $(M+H)^+$.

QY-3-99

$^1$H NMR (400 MHz, DMSO-d6) δ 7.53 (m, 1H), 7.29 (t, J=7.4 Hz, 2H), 7.22-7.09 (m, 4H), 6.79 (t, J=9.0 Hz, 1H), 5.07 (dd, J=8.1, 4.3 Hz, 1H), 3.88-3.74 (m, 2H), 2.18-2.08 (m, 1H), 1.97-1.61 (m, 3H), 1.58 (s, 3H), 1.48 (s, 3H); ESI-MS m/z 362.0 $(M+H)^+$.

QY-4-1

$^1$H NMR (400 MHz, DMSO-d6) δ 7.93 (s, 1H), 7.11 (s, 1H), 5.25 (dd, J=8.3, 5.5 Hz, 1H), 3.90 (m, 1H), 3.58 (m, 1H), 2.33 (s, 3H), 2.28 (m, 1H), 1.99-1.93 (m, 2H), 1.79 (m, 1H), 1.62 (s, 3H), 1.44 (s, 3H); ESI-MS m/z 418.0 (M+H)$^+$.

QY-4-2

$^1$H NMR (400 MHz, DMSO-d6) δ 7.48 (d, J=8.1 Hz, 2H), 5.22 (dd, J=8.4, 4.2 Hz, 1H), 3.99 (dd, J=9.8, 4.5 Hz, 2H), 2.31 (s, 3H), 2.25 (dd, J=9.9, 5.7 Hz, 1H), 2.07-1.98 (m, 2H), 1.91-1.85 (m, 1H), 1.48 (s, 3H), 1.33 (s, 3H); ESI-MS m/z 386.1 (M+H)$^+$.

QY-4-6

$^1$H NMR (400 MHz, DMSO-d6) δ 7.39-7.30 (m, 4H), 7.12 (d, J=8.4 Hz, 2H), 6.82-6.74 (m, 2H), 5.03 (dd, J=8.1, 4.6 Hz, 1H), 3.81-3.65 (m, 2H), 2.14-2.06 (m, 1H), 1.88-1.56 (m, 3H), 1.55 (s, 3H), 1.48 (s, 3H); ESI-MS m/z 378.0 (M+H)$^+$.

QY-4-7

$^1$H NMR (400 MHz, DMSO-d6) δ 7.36-7.29 (m, 2H), 7.15-7.07 (m, 4H), 6.81-6.75 (m, 2H), 5.05 (dd, J=8.1, 4.5 Hz, 1H), 3.82-3.66 (m, 2H), 2.12-2.04 (m, 1H), 1.86-1.56 (m, 3H), 1.54 (s, 3H), 1.48 (s, 3H); ESI-MS m/z 362.1 (M+H)$^+$.

QY-4-8

$^1$H NMR (400 MHz, DMSO-d6) δ 7.32 (d, J=9.0 Hz, 2H), 7.08 (d, J=7.9 Hz, 2H), 6.96 (d, J=8.0 Hz, 2H), 6.81-6.75 (m, 2H), 5.02 (dd, J=8.0, 4.3 Hz, 1H), 3.81-3.63 (m, 2H), 2.27 (s, 3H), 2.10-2.00 (m, 1H), 1.87-1.55 (m, 3H), 1.54 (s, 3H), 1.48 (s, 3H); ESI-MS m/z 358.1 (M+H)$^+$.

QY-4-11

$^1$H NMR (400 MHz, DMSO-d6) δ 7.26 (d, J=9.0 Hz, 2H), 6.76 (d, J=9.0 Hz, 2H), 5.32 (dd, J=7.5, 4.2 Hz, 1H), 4.14 (s, 3H), 3.82-3.70 (m, 2H), 2.24-2.12 (m, 2H), 1.92-1.82 (m, 2H), 1.48 (s, 3H), 1.38 (s, 3H); ESI-MS m/z 350.1 (M+H)$^+$.

QY-4-12

$^1$H NMR (400 MHz, DMSO-d6) δ 7.36-7.27 (m, 2H), 6.91-6.82 (m, 2H), 5.35 (dd, J=8.2, 3.8 Hz, 1H), 4.33 (s, 3H), 3.80-3.68 (m, 2H), 2.21-2.11 (m, 1H), 1.89 (m, 2H), 1.73-1.66 (m, 1H), 1.50 (s, 3H), 1.43 (s, 3H); ESI-MS m/z 350.1 (M+H)$^+$.

QY-4-14

$^1$H NMR (400 MHz, DMSO-d6) δ 7.30 (t, J=8.7 Hz, 2H), 5.22 (dd, J=8.4, 4.3 Hz, 1H), 4.01 (m, 2H), 2.31 (s, 3H), 2.11-1.83 (m, 4H), 1.47 (s, 3H), 1.32 (s, 3H); ESI-MS m/z 370.1 (M+H)$^+$.

QY-4-27

$^1$H NMR (400 MHz, DMSO-d6) δ 7.37-7.31 (m, 2H), 7.15-7.06 (m, 3H), 6.83-6.76 (m, 3H), 5.20 (dd, J=8.2, 4.1 Hz, 1H), 3.81-3.74 (m, 2H), 2.33 (s, 3H), 2.15-1.69 (m, 4H), 1.56 (s, 3H), 1.48 (s, 3H); ESI-MS m/z 358.1 (M+H)$^+$.

QY-4-32

$^1$H NMR (400 MHz, DMSO-d6) δ 7.47-7.33 (m, 3H), 7.29-7.21 (m, 2H), 6.98-6.90 (m, 1H), 6.87-6.79 (m, 2H), 5.34 (dd, J=8.3, 3.6 Hz, 1H), 3.89-3.70 (m, 2H), 2.19-1.69 (m, 4H), 1.60 (s, 3H), 1.47 (s, 3H); ESI-MS m/z 378.0 (M+H)$^+$.

QY-4-35

$^1$H NMR (400 MHz, DMSO-d6) δ 7.37-7.20 (m, 4H), 7.08 (t, J=3.9 Hz, 2H), 6.83-6.73 (m, 2H), 5.03 (dd, J=8.1, 4.8 Hz, 1H), 3.86-3.63 (m, 2H), 2.11 (m, 1H), 1.89-1.57 (m, 3H), 1.55 (s, 3H), 1.50 (s, 3H); ESI-MS m/z 378.0 (M+H)$^+$.

QY-4-39

$^1$H NMR (400 MHz, DMSO-d6) δ 7.38-7.25 (m, 3H), 7.01 (m, 2H), 6.88-6.76 (m, 3H), 5.06 (dd, J=8.1, 4.4 Hz, 1H), 3.83-3.67 (m, 2H), 2.15-2.06 (m, 1H), 1.90-1.58 (m, 3H), 1.56 (s, 3H), 1.49 (s, 3H); ESI-MS m/z 362.1 (M+H)$^+$.

QY-4-66

$^1$H NMR (400 MHz, DMSO-d6) δ 8.00 (d, J=2.7 Hz, 1H), 7.62 (m, 1H), 7.08 (d, J=7.9 Hz, 2H), 6.95 (d, J=8.0 Hz, 2H), 6.74 (d, J=9.1 Hz, 1H), 5.01 (dd, J=8.0, 4.6 Hz, 1H), 3.77-3.62 (m, 2H), 2.28 (s, 3H), 2.12-2.04 (m, 1H), 1.93-1.62 (m, 3H), 1.61 (s, 3H), 1.57 (s, 3H); ESI-MS m/z 383.2 (M+H)$^+$.

QY-4-67

$^1$H NMR (400 MHz, DMSO-d6) δ 7.74 (d, J=2.6 Hz, 1H), 7.60 (dd, J=9.0, 2.6 Hz, 1H), 7.10 (d, J=7.9 Hz, 2H), 6.99 (d, J=8.1 Hz, 2H), 6.72 (d, J=9.0 Hz, 1H), 5.03 (dd, J=8.0, 4.5 Hz, 1H), 3.76-3.62 (m, 2H), 2.28 (s, 3H), 2.14-2.05 (m, 1H), 1.89-1.58 (m, 3H), 1.56 (s, 3H), 1.52 (s, 3H); ESI-MS m/z 426.0 (M+H)$^+$.

QY-4-69

$^1$H NMR (400 MHz, DMSO-d6) δ 7.69 (m, 1H), 7.52 (m, 4H), 7.16 (m, 1H), 6.76 (t, J=9.0 Hz, 1H), 5.07 (dd, J=8.1, 5.1 Hz, 1H), 3.92-3.75 (m, 2H), 2.17 (m, 1H), 1.91-1.61 (m, 3H), 1.57 (s, 3H), 1.49 (s, 3H); ESI-MS m/z 387.2 (M+H)$^+$.

QY-4-70

$^1$H NMR (400 MHz, DMSO-d6) δ 7.51 (m, 1H), 7.20 (t, J=7.9 Hz, 1H), 7.13 (m, 1H), 6.83-6.76 (m, 2H), 6.66 (m, 2H), 5.05 (dd, J=8.1, 4.2 Hz, 1H), 3.80 (m, 2H), 3.73 (s, 3H), 2.17-2.08 (m, 1H), 1.89-1.61 (m, 3H), 1.58 (s, 3H), 1.47 (s, 3H); ESI-MS m/z 392.1 (M+H)$^+$.

QY-4-75

$^1$H NMR (400 MHz, DMSO-d6) δ 7.51 (m, 1H), 7.15 (m, 1H), 7.09 (d, J=7.9 Hz, 2H), 6.98 (d, J=8.0 Hz, 2H), 6.78 (t, J=9.0 Hz, 1H), 5.03 (dd, J=8.0, 4.4 Hz, 1H), 3.87-3.70 (m, 2H), 2.27 (s, 3H), 2.13-2.07 (m, 1H), 1.93-1.59 (m, 3H), 1.56 (s, 3H), 1.48 (s, 3H); ESI-MS m/z 376.1 (M+H)$^+$.

QY-4-78

$^1$H NMR (400 MHz, DMSO-d6) δ 7.52 (dd, J=11.0, 2.6 Hz, 1H), 7.30-7.25 (m, 1H), 7.15 (m, 3H), 7.02 (m, 1H), 6.83 (t, J=9.0 Hz, 1H), 5.26 (dd, J=8.2, 4.4 Hz, 1H), 3.83 (m, 2H), 2.21-2.12 (m, 1H), 1.81 (m, 3H), 1.59 (s, 3H), 1.46 (s, 3H); ESI-MS m/z 380.1 (M+H)$^+$.

QY-4-87

$^1$H NMR (400 MHz, DMSO-d6) δ 7.51 (m, 1H), 7.14 (m, 1H), 7.02 (d, J=8.6 Hz, 2H), 6.84 (d, J=8.7 Hz, 2H), 6.75 (d, J=9.0 Hz, 1H), 5.02 (dd, J=8.0, 4.4 Hz, 1H), 3.86-3.70 (m, 5H), 2.13-2.05 (m, 1H), 1.92-1.61 (m, 3H), 1.55 (s, 3H), 1.48 (s, 3H); ESI-MS m/z 392.2 (M+H)$^+$.

QY-4-88

$^1$H NMR (400 MHz, DMSO-d6) δ 7.78 (d, J=8.3 Hz, 2H), 7.52 (m, 1H), 7.32 (d, J=8.2 Hz, 2H), 7.24-7.21 (m, 1H), 6.79 (m, 1H), 5.09 (dd, J=8.1, 5.0 Hz, 1H), 3.91-3.76 (m, 2H), 2.19 (m, 1H), 1.93-1.60 (m, 3H), 1.57 (s, 3H), 1.47 (s, 3H); ESI-MS m/z 387.1 (M+H)$^+$.

QY-4-96

$^1$H NMR (400 MHz, DMSO-d6) δ 7.34-7.29 (m, 2H), 7.11 (d, J=8.1 Hz, 2H), 6.98 (d, J=8.1 Hz, 2H), 6.81-6.76 (m, 2H), 5.03 (dd, J=8.1, 4.1 Hz, 1H), 3.80-3.65 (m, 2H), 2.58 (q, J=7.5 Hz, 2H), 2.10-2.01 (m, 1H), 1.88-1.57 (m, 3H), 1.55 (s, 3H), 1.48 (s, 3H), 1.18 (t, J=7.6 Hz, 3H); ESI-MS m/z 372.1 (M+H)$^+$.

QY-4-99

$^1$H NMR (400 MHz, DMSO-d6) δ 7.52 (m, 1H), 7.17-7.10 (m, 3H), 7.00 (d, J=8.0 Hz, 2H), 6.78 (t, J=9.0 Hz, 1H), 5.05 (dd, J=8.0, 4.2 Hz, 1H), 3.87-3.72 (m, 2H), 2.57 (q, J=7.6 Hz, 2H), 2.14-2.05 (m, 1H), 1.80 (m, 3H), 1.57 (s, 3H), 1.48 (s, 3H), 1.18 (t, J=7.6 Hz, 3H); ESI-MS m/z 390.0 (M+H)$^+$.

QY-5-1

$^1$H NMR (400 MHz, DMSO-d6) δ 7.52 (m, 1H), 7.15 (d, J=8.1 Hz, 2H), 7.12 (dd, J=2.5, 1.6 Hz, 1H), 7.01 (d, J=8.1 Hz, 2H), 6.79 (t, J=9.0 Hz, 1H), 5.06 (dd, J=8.1, 4.1 Hz, 1H), 3.86-3.70 (m, 2H), 2.86 (m, 1H), 2.15-2.05 (m, 1H), 1.98-

1.61 (m, 3H), 1.57 (s, 3H), 1.48 (s, 3H), 1.20 (d, J=6.9 Hz, 6H); ESI-MS m/z 404.2 $(M+H)^+$.

QY-5-4

$^1$H NMR (400 MHz, DMSO-d6) δ 7.51 (m, 1H), 7.12 (m, 4H), 6.76 (t, J=9.0 Hz, 2H), 5.03 (dd, J=8.0, 4.3 Hz, 1H), 3.79 (m, 2H), 2.97 (s, 6H), 2.09 (m, 1H), 1.87-1.58 (m, 3H), 1.55 (s, 3H), 1.48 (s, 3H); ESI-MS m/z 405.1 $(M+H)^+$.

QY-5-21

$^1$H NMR (400 MHz, DMSO-d6) δ 7.34-7.29 (m, 2H), 7.08 (d, J=7.8 Hz, 2H), 6.96 (d, J=8.0 Hz, 2H), 6.81-6.76 (m, 2H), 5.02 (dd, J=8.0, 4.3 Hz, 1H), 3.81-3.64 (m, 2H), 2.27 (s, 3H), 2.09-2.02 (m, 1H), 1.86-1.56 (m, 3H), 1.54 (s, 3H), 1.48 (s, 3H); ESI-MS m/z 358.1 $(M+H)^+$.

QY-5-22

$^1$H NMR (400 MHz, DMSO-d6) δ 7.52 (m, 1H), 7.15 (m, 1H), 7.09 (d, J=7.9 Hz, 2H), 6.98 (d, J=8.0 Hz, 2H), 6.78 (t, J=9.0 Hz, 1H), 5.03 (dd, J=8.0, 4.4 Hz, 1H), 3.86-3.69 (m, 2H), 2.27 (s, 3H), 2.09 (m, 1H), 1.92-1.59 (m, 3H), 1.56 (s, 3H), 1.48 (s, 3H); ESI-MS m/z 376.2 $(M+H)^+$.

QY-5-79

$^1$H NMR (400 MHz, DMSO-d6) δ 8.38 (d, J=4.5 Hz, 1H), 7.74 (d, J=8.3 Hz, 2H), 7.53 (m, 1H), 7.21-7.15 (m, 3H), 6.79 (t, J=9.0 Hz, 1H), 5.08 (dd, J=8.0, 4.8 Hz, 1H), 3.90-3.73 (m, 2H), 2.78 (d, J=4.5 Hz, 3H), 2.20-2.12 (m, 1H), 1.92-1.59 (m, 3H), 1.57 (s, 3H), 1.48 (s, 3H); ESI-MS m/z 419.1 $(M+H)^+$.

QY-5-83

$^1$H NMR (400 MHz, DMSO-d6) δ 7.66 (d, J=8.1 Hz, 2H), 7.53 (m, 1H), 7.35 (d, J=8.1 Hz, 2H), 7.22-7.19 (m, 1H), 6.81 (t, J=9.0 Hz, 1H), 5.12 (dd, J=8.1, 4.8 Hz, 1H), 3.90-3.77 (m, 2H), 2.23-2.14 (m, 1H), 1.95-1.61 (m, 3H), 1.59 (s, 3H), 1.47 (s, 3H); ESI-MS m/z 430.0 $(M+H)^+$.

QY-5-85

$^1$H NMR (400 MHz, DMSO-d6) δ 7.93 (s, 1H), 7.79 (d, J=8.3 Hz, 2H), 7.53 (dd, J=11.0, 2.6 Hz, 1H), 7.32 (s, 1H), 7.22-7.16 (m, 3H), 6.79 (t, J=9.0 Hz, 1H), 5.08 (dd, J=8.1, 4.8 Hz, 1H), 3.89-3.74 (m, 2H), 2.16 (dd, J=12.4, 7.2 Hz, 1H), 1.92-1.60 (m, 3H), 1.57 (s, 3H), 1.48 (s, 3H); ESI-MS m/z 405.1 $(M+H)^+$.

QY-6-47

$^1$H NMR (400 MHz, DMSO-d6) δ 7.40 (m, 1H), 7.26 (s, 1H), 7.11 (d, J=7.9 Hz, 2H), 6.98-6.92 (m, 3H), 6.70 (t, J=9.0 Hz, 1H), 5.31 (m, 1H), 3.39 (m, 1H), 2.63-2.57 (m, 1H), 2.28 (s, 3H), 1.63 (s, 3H), 1.61 (s, 3H); ESI-MS m/z 375.0 $(M+H)^+$.

QY-6-60

$^1$H NMR (400 MHz, DMSO-d6) δ 7.53 (m, 1H), 7.14-7.03 (m, 2H), 6.85-6.77 (m, 3H), 5.05 (dd, J=8.1, 4.6 Hz, 1H), 3.82 (m, 2H), 2.19-2.10 (m, 1H), 1.92-1.61 (m, 3H), 1.59 (s, 3H), 1.49 (s, 3H); ESI-MS m/z 398.1 $(M+H)^+$.

QY-6-61

$^1$H NMR (400 MHz, DMSO-d6) δ 7.52 (dd, J=11.0, 2.6 Hz, 1H), 7.35 (dt, J=10.7, 8.5 Hz, 1H), 7.18-7.09 (m, 2H), 7.01-6.95 (m, 1H), 6.77 (t, J=9.0 Hz, 1H), 5.03 (dd, J=8.1, 4.7 Hz, 1H), 3.89-3.73 (m, 2H), 2.18-2.09 (m, 1H), 1.92-1.60 (m, 3H), 1.57 (s, 3H), 1.48 (s, 3H); ESI-MS m/z 398.2 $(M+H)^+$.

QY-6-62

$^1$H NMR (400 MHz, DMSO-d6) δ 7.52 (m, 1H), 7.20-7.08 (m, 5H), 6.77 (t, J=9.0 Hz, 1H), 5.06 (dd, J=8.0, 4.6 Hz, 1H), 3.87-3.72 (m, 2H), 2.17-2.09 (m, 1H), 1.93-1.59 (m, 3H), 1.56 (s, 3H), 1.48 (s, 3H); ESI-MS m/z 380.1 $(M+H)^+$.

QY-6-63

$^1$H NMR (400 MHz, DMSO-d6) δ 8.42 (d, J=4.5 Hz, 1H), 7.73 (m, 1H), 7.57 (dd, J=8.6, 1.0 Hz, 1H), 7.08 (d, J=7.9 Hz, 2H), 6.97 (d, J=8.0 Hz, 2H), 6.79 (t, J=8.5 Hz, 1H), 5.02 (dd, J=8.0, 4.5 Hz, 1H), 3.83-3.65 (m, 2H), 2.78 (t, J=4.8 Hz, 3H), 2.28 (s, 3H), 2.11-1.66 (m, 4H), 1.58 (s, 3H), 1.53 (s, 3H); ESI-MS m/z 399.1 $(M+H)^+$.

QY-6-83

$^1$H NMR (400 MHz, DMSO-d6) δ 7.35-7.26 (m, 4H), 7.23-7.19 (m, 1H), 7.10-7.06 (m, 2H), 6.83-6.76 (m, 2H), 5.06 (dd, J=8.1, 4.2 Hz, 1H), 3.81-3.68 (m, 2H), 2.12-2.04 (m, 1H), 1.87-1.57 (m, 3H), 1.56 (s, 3H), 1.48 (s, 3H); ESI-MS m/z 344.1 $(M+H)^+$.

QY-6-84

$^1$H NMR (400 MHz, DMSO-d6) δ 7.53 (m, 1H), 7.29 (t, J=7.3 Hz, 2H), 7.22-7.09 (m, 4H), 6.79 (t, J=9.0 Hz, 1H), 5.07 (dd, J=8.1, 4.3 Hz, 1H), 3.86-3.75 (m, 2H), 2.20-2.10 (m, 1H), 1.91-1.60 (m, 3H), 1.58 (s, 3H), 1.48 (s, 3H); ESI-MS m/z 362.1 $(M+H)^+$.

QY-7-7

$^1$H NMR (400 MHz, DMSO-d6) δ 7.52 (m, 1H), 7.15 (m, 1H), 6.77 (t, J=9.0 Hz, 1H), 3.87-3.70 (m, 2H), 2.13-2.05 (m, 1H), 1.91-1.58 (m, 3H), 1.55 (s, 3H), 1.48 (s, 3H); ESI-MS m/z 384.2 $(M+H)^+$.

QY-7-101

$^1$H NMR (400 MHz, DMSO-d6) δ 7.22 (d, J=1.5 Hz, 1H), 7.11 (d, J=8.7 Hz, 1H), 7.06 (d, J=7.9 Hz, 2H), 6.89 (d, J=8.0 Hz, 2H), 6.44 (d, J=2.7 Hz, 1H), 6.23 (dd, J=8.7, 2.7 Hz, 1H), 5.29 (m, 1H), 3.56 (s, 3H), 3.36 (m, 1H), 2.56 (m, 1H), 2.27 (s, 3H), 1.62 (d, J=2.6 Hz, 6H); ESI-MS m/z 387.0 $(M+H)^+$.

QY-8-101

$^1$H NMR (400 MHz, DMSO-d6) δ 7.41 (m, 1H), 7.38 (d, J=8.5 Hz, 2H), 7.28 (d, J=1.5 Hz, 1H), 7.13-7.07 (m, 2H), 6.98 (m, 1H), 6.71 (t, J=9.0 Hz, 1H), 5.37 (m, 1H), 3.46-3.35 (m, 1H), 2.69-2.61 (m, 1H), 1.62 (d, J=10.1 Hz, 6H); ESI-MS m/z 395.1 $(M+H)^+$.

QY-9-8

$^1$H NMR (400 MHz, DMSO-d6) δ 7.11-7.06 (m, 3H), 6.98 (d, J=8.1 Hz, 2H), 6.85 (dd, J=8.6, 2.5 Hz, 1H), 6.64-6.59 (m, 1H), 5.02 (dd, J=8.0, 4.2 Hz, 1H), 3.87-3.81 (m, 1H), 3.79 (s, 3H), 3.71 (m, 1H), 2.27 (s, 3H), 2.13-2.03 (m, 1H), 1.76 (m, 2H), 1.56 (m, 1H), 1.51 (s, 3H), 1.42 (s, 3H); ESI-MS m/z 388.0 $(M+H)^+$.

QY-9-32

$^1$H NMR (400 MHz, DMSO-d6) δ 7.42-7.35 (m, 2H), 7.24 (d, J=1.5 Hz, 1H), 7.15-7.10 (m, 2H), 7.00 (d, J=2.5 Hz, 1H), 6.70 (dd, J=8.6, 2.5 Hz, 1H), 6.54 (d, J=8.6 Hz, 1H), 5.37 (m, 1H), 3.74 (s, 3H), 3.35 (m, 1H), 2.63 (m, 1H), 1.57 (s, 3H), 1.54 (s, 3H); ESI-MS m/z 406.9 $(M+H)^+$.

QY-9-43

$^1$H NMR (400 MHz, DMSO-d6) δ 7.37-7.31 (m, 2H), 7.13 (d, J=8.4 Hz, 2H), 7.10 (d, J=2.5 Hz, 1H), 6.89 (m, 1H), 6.62 (d, J=8.6 Hz, 1H), 5.04 (m, 1H), 3.89-3.81 (m, 1H), 3.79 (s, 3H), 3.72 (m, 1H), 2.18-2.09 (m, 1H), 1.84-1.70 (m, 2H), 1.57 (d, J=6.1 Hz, 1H), 1.52 (s, 3H), 1.41 (s, 3H); ESI-MS m/z 408.1 $(M+H)^+$.

QY-10-1

$^1$H NMR (400 MHz, DMSO-d6) δ 7.36-7.32 (m, 2H), 7.13 (d, J=8.4 Hz, 2H), 7.09 (d, J=2.5 Hz, 1H), 6.88 (dd, J=8.6, 2.5 Hz, 1H), 6.62 (d, J=8.6 Hz, 1H), 5.04 (m, 1H), 3.84 (s, 1H), 3.79 (s, 3H), 3.71 (m, 1H), 2.16-2.08 (m, 1H), 1.73 (d, J=5.9 Hz, 2H), 1.60-1.54 (m, 1H), 1.52 (s, 3H), 1.41 (s, 3H); ESI-MS m/z 408.1 $(M+H)^+$.

QY-10-92

$^1$H NMR (400 MHz, DMSO-d6) δ 9.13 (s, 1H), 8.08 (d, J=1.9 Hz, 1H), 7.38-7.32 (m, 2H), 7.14 (d, J=8.5 Hz, 2H), 7.03 (m, 1H), 6.55 (d, J=8.8 Hz, 1H), 5.03 (dd, J=8.1, 4.9 Hz, 1H), 3.88-3.79 (m, 1H), 3.64 (m, 1H), 2.14 (s, 3H), 2.03 (m, 1H), 1.91-1.65 (m, 3H), 1.58 (s, 3H), 1.51 (s, 3H); ESI-MS m/z 435.1 $(M+H)^+$.

QY-10-96

$^1$H NMR (400 MHz, DMSO-d6) δ 7.22 (t, J=1.5 Hz, 1H), 7.11 (d, J=7.8 Hz, 2H), 6.99 (d, J=2.6 Hz, 2H), 6.97 (s, 1H), 6.67 (dd, J=8.6, 2.5 Hz, 1H), 6.54 (d, J=8.6 Hz, 1H), 5.32 (m, 1H), 3.74 (s, 3H), 3.41-3.34 (m, 1H), 2.59 (m, 1H), 2.28 (s, 3H), 1.56 (s, 3H), 1.54 (s, 3H); ESI-MS m/z 387.0 $(M+H)^+$.

QY-10-104

$^1$H NMR (400 MHz, DMSO-d6) δ7.31 (d, J=8.4 Hz, 2H), 7.08 (d, J=8.4 Hz, 2H), 6.92 (d, J=2.3 Hz, 1H), 6.76 (m, 1H), 6.15 (d, J=8.5 Hz, 1H), 5.02 (d, J=5.3 Hz, 1H), 3.84 (s, 3H), 3.80-3.57 (m, 3H), 2.04-1.97 (m, 1H), 1.75-1.49 (m, 3H), 1.45 (s, 3H), 1.40 (s, 3H); ESI-MS m/z 407.0 $(M+H)^+$.

QY-11-1 $^1$H NMR (400 MHz, DMSO-d6) δ 7.09 (d, J=2.5 Hz, 1H), 6.85 (dd, J=8.6, 2.5 Hz, 1H), 6.62 (d, J=8.6 Hz, 1H), 3.79 (s, 3H), 3.74-3.60 (m, 2H), 2.12-2.04 (m, 1H), 1.86-1.68 (m, 2H), 1.59-1.53 (m, 1H), 1.51 (s, 3H), 1.42 (s, 3H); ESI-MS m/z 396.1 $(M+H)^+$.

QY-11-9A $^1$H NMR (400 MHz, DMSO-d6) δ 8.60 (s, 1H), 7.85 (d, J=1.5 Hz, 1H), 7.80 (d, J=9.1 Hz, 1H), 7.39 (d, J=8.4 Hz, 2H), 7.27 (dd, J=13.5, 5.1 Hz, 3H), 5.11-5.06 (m, 1H), 2.39 (t, J=5.6 Hz, 2H), 2.08-2.01 (m, 1H), 1.83 (d, J=6.8 Hz, 6H), 1.53-1.43 (m, 3H); ESI-MS m/z 402.1 $(M+H)^+$.

QY-11-9B $^1$H NMR (400 MHz, DMSO-d6) δ 8.20 (s, 1H), 7.96 (d, J=1.9 Hz, 1H), 7.45 (dd, J=8.9, 1.6 Hz, 1H), 7.35 (d, J=8.3 Hz, 2H), 7.20 (d, J=8.9 Hz, 1H), 7.11 (d, J=8.4 Hz, 2H), 5.02 (dd, J=7.9, 4.3 Hz, 1H), 2.58 (m, 1H), 2.34-2.27 (m, 1H), 1.94 (m, 1H), 1.84 (s, 3H), 1.74 (s, 3H), 1.58-1.51 (m, 1H), 1.41 (m, 2H); ESI-MS m/z 402.1 $(M+H)^+$.

QY-11-11A $^1$H NMR (400 MHz, DMSO-d6) δ 8.21 (d, J=8.9 Hz, 1H), 7.54 (dd, J=8.9, 1.2 Hz, 1H), 7.33 (d, J=8.4 Hz, 3H), 7.10 (d, J=8.3 Hz, 2H), 5.02 (dd, J=7.7, 5.6 Hz, 1H), 2.69 (m, 1H), 2.41-2.35 (m, 1H), 2.00 (s, 3H), 1.89 (s, 3H), 1.52 (m, 4H); ESI-MS m/z 403.0 $(M+H)^+$.

QY-11-11B $^1$H NMR (400 MHz, DMSO-d6) δ 8.24 (d, J=1.1 Hz, 1H), 8.12 (m, 1H), 7.53 (dd, J=9.1, 1.7 Hz, 1H), 7.40 (d, J=8.3 Hz, 2H), 7.24 (d, J=8.3 Hz, 2H), 5.09 (m, 1H), 2.35 (t, J=6.7 Hz, 2H), 2.10-2.03 (m, 1H), 1.92 (s, 6H), 1.56-1.44 (m, 3H); ESI-MS m/z 403.0 $(M+H)^+$.

QY-11-15B $^1$H NMR (400 MHz, DMSO-d6) δ 7.67 (t, J=2.9 Hz, 2H), 7.37-7.31 (m, 2H), 7.15 (m, 1H), 7.09 (d, J=8.4 Hz, 2H), 7.03 (d, J=8.8 Hz, 1H), 6.57 (d, J=3.2 Hz, 1H), 5.03 (m, 1H), 2.73-2.64 (m, 1H), 2.31 (m, 1H), 1.91-1.83 (m, 1H), 1.80 (s, 3H), 1.69 (s, 3H), 1.58-1.50 (m, 1H), 1.45-1.37 (m, 2H); ESI-MS m/z 401.1 $(M+H)^+$.

QY-11-16A $^1$H NMR (400 MHz, DMSO-d6) δ 8.67 (s, 1H), 7.79 (d, J=8.6 Hz, 1H), 7.39-7.31 (m, 3H), 7.07 (dd, J=5.2, 3.2 Hz, 3H), 5.02 (m, 1H), 2.87-2.78 (m, 1H), 1.98 (m, 1H), 1.87 (s, 3H), 1.80 (s, 3H), 1.64-1.42 (m, 4H); ESI-MS m/z 402.0 $(M+H)^+$.

QY-11-16B $^1$H NMR (400 MHz, DMSO-d6) δ 8.57 (s, 1H), 7.77 (d, J=1.9 Hz, 1H), 7.32-7.22 (m, 3H), 7.03 (m, 3H), 4.96 (m, 1H), 2.71 (s, 1H), 1.93 (m, 1H), 1.80 (s, 3H), 1.72 (s, 3H), 1.44 (m, 4H); ESI-MS m/z 402.0 $(M+H)^+$.

QY-11-36

$^1$H NMR (400 MHz, DMSO-d6) δ 7.88-7.71 (m, 2H), 7.43-7.29 (m, 2H), 7.14-7.02 (m, 2H), 6.95-6.79 (m, 2H), 5.00 (dd, J=8.1, 4.9 Hz, 1H), 3.73 (m, 1H), 3.58 (m, 1H), 2.08 (m, 1H), 1.74 (m, 3H), 1.58 (s, 3H), 1.55 (s, 3H); ESI-MS m/z 369.1 $(M+H)^+$; ESI-MS m/z 369.1 $(M+H)^+$.

QY-11-44

$^1$H NMR (400 MHz, DMSO-d6) δ 9.25 (s, 1H), 8.00 (d, J=8.9 Hz, 1H), 7.36 (d, J=2.5 Hz, 1H), 7.34-7.25 (m, 2H), 7.14-7.08 (m, 2H), 7.05 (dd, J=8.9, 2.6 Hz, 1H), 5.06 (dd, J=8.1, 4.9 Hz, 1H), 3.93 (m, 1H), 3.65 (m, 1H), 2.22-2.01 (m, 1H), 1.77 (m, 2H), 1.58 (s, 3H), 1.55 (s, 3H), 1.51 (m, 1H); ESI-MS m/z 401.2 $(M+H)^+$.

QY-11-45

$^1$H NMR (400 MHz, DMSO-d6) δ 7.94 (dd, J=11.2, 2.1 Hz, 1H), 7.64 (dt, J=8.7, 1.5 Hz, 1H), 7.40-7.30 (m, 2H), 7.16-7.05 (m, 2H), 6.82 (t, J=8.6 Hz, 1H), 5.01 (dd, J=8.1, 4.9 Hz, 1H), 3.76 (m, 1H), 3.63 (m, 1H), 2.11 (m, 1H), 1.78 (m, 2H), 1.61 (s, 3H), 1.57 (s, 3H), 1.53 (m, 1H); ESI-MS m/z 387.2 $(M+H)^+$.

QY-12-11

$^1$H NMR (400 MHz, DMSO-d6) δ 7.49 (d, J=2.0 Hz, 1H), 7.42-7.29 (m, 3H), 7.17-7.02 (m, 2H), 6.67 (d, J=8.4 Hz, 1H), 5.01 (dd, J=8.1, 4.8 Hz, 1H), 3.84 (s, 3H), 3.78-3.67 (m, 1H), 3.59 (m, 1H), 2.18-2.03 (m, 1H), 1.80 (m, 1H), 1.68 (m, 1H), 1.57 (s, 3H), 1.54 (m, 1H), 1.51 (s, 3H); ESI-MS m/z 399.1 $(M+H)^+$.

QY-12-14

$^1$H NMR (400 MHz, DMSO-d6) δ 7.49 (d, J=2.0 Hz, 1H), 7.32 (dt, J=8.4, 1.4 Hz, 1H), 6.67 (d, J=8.4 Hz, 1H), 3.84 (s, 3H), 3.78-3.66 (m, 1H), 3.57 (m, 1H), 2.12-1.97 (m, 1H), 1.72 (m, 2H), 1.56 (s, 3H), 1.52 (s, 3H), 1.48 (m, 1H); ESI-MS m/z 387.2 $(M+H)^+$.

QY-12-32

$^1$H NMR (400 MHz, DMSO-d6) δ 8.09 (s, 1H), 7.54 (d, J=8.7 Hz, 1H), 7.33-7.23 (m, 2H), 7.15-7.05 (m, 2H), 6.86 (d, J=2.3 Hz, 1H), 6.72 (dd, J=8.8, 2.4 Hz, 1H), 5.09 (dd, J=8.2, 4.2 Hz, 1H), 3.95 (m, 1H), 3.78 (m, 1H), 3.67 (s, 3H), 2.12 (m, 1H), 1.89-1.66 (m, 2H), 1.58 (s, 3H), 1.53 (m, 1H), 1.50 (s, 3H); ESI-MS m/z 398.1 $(M+H)^+$.

QY-13-42

$^1$H NMR (400 MHz, Chloroform-d) δ 8.00 (d, J=2.7 Hz, 1H), 7.56 (dd, J=8.8, 2.7 Hz, 1H), 7.08 (d, J=7.8 Hz, 2H), 6.99 (d, J=7.8 Hz, 2H), 6.72 (d, J=8.7 Hz, 1H), 5.15 (dd, J=8.2, 4.1 Hz, 1H), 3.69 (m, 1H), 3.52-3.37 (m, 1H), 2.31 (s, 3H), 2.16-2.04 (m, 1H), 1.87 (m, 1H), 1.73 (q, J=6.2 Hz, 2H), 1.68 (s, 3H), 1.64 (s, 3H); ESI-MS m/z 359.2 $(M+H)^+$.

QY-13-68

$^1$H NMR (400 MHz, DMSO-d6) δ 8.56 (d, J=2.3 Hz, 1H), 8.23 (dd, J=8.7, 2.4 Hz, 1H), 7.08 (d, J=8.2 Hz, 3H), 6.92 (d, J=7.8 Hz, 2H), 4.97 (dd, J=8.1, 4.1 Hz, 1H), 3.55 (m, 1H), 3.32 (m, 1H), 2.28 (s, 3H), 2.01 (m, 1H), 1.69 (m, 2H), 1.63 (s, 3H), 1.59 (s, 3H), 1.49 (m, 1H); ESI-MS m/z 350.2 $(M+H)^+$.

QY-13-70

$^1$H NMR (400 MHz, DMSO-d6) δ 8.67 (s, 2H), 7.07 (d, J=7.8 Hz, 2H), 6.92 (d, J=7.7 Hz, 2H), 4.97 (dd, J=8.1, 4.1 Hz, 1H), 3.63-3.51 (m, 1H), 3.38 (m, 1H), 2.27 (s, 3H), 2.01 (m, 1H), 1.71 (m, 2H), 1.63 (s, 3H), 1.59 (s, 3H), 1.50 (m, 1H); ESI-MS m/z 360.1 $(M+H)^+$.

QY-13-86

$^1$H NMR (400 MHz, DMSO-d6) δ 7.94 (s, 1H), 7.37 (d, J=7.8 Hz, 1H), 7.27 (d, J=7.8 Hz, 1H), 7.04 (d, J=7.7 Hz, 2H), 6.92 (d, J=7.7 Hz, 2H), 4.97 (dd, J=8.0, 3.8 Hz, 1H), 3.63 (m, 1H), 3.35-3.18 (m, 1H), 2.26 (s, 3H), 2.00 (m, 2H), 1.77-1.63 (m, 2H), 1.49 (s, 3H), 1.46 (s, 3H); ESI-MS m/z 359.1 $(M+H)^+$.

QY-14-8

$^1$H NMR (400 MHz, DMSO-d6) δ 7.08 (d, J=7.7 Hz, 2H), 7.03 (d, J=8.3 Hz, 2H), 5.14-4.82 (m, 1H), 3.44 (m, 4H), 2.88 (m, 1H), 2.56 (m, 1H), 2.25 (s, 3H), 2.16 (m, 1H), 2.01-1.75 (m, 2H), 1.74-1.47 (m, 4H), 1.28 (s, 3H), 1.24 (s,

1H), 1.19 (s, 3H), 0.93 (m, 1H), 0.90 (d, J=6.1 Hz, 3H), 0.87-0.77 (m, 1H); ESI-MS m/z 357.2 $(M+H)^+$.

QY-14-9

$^1$H NMR (400 MHz, DMSO-d6) δ 7.09 (d, J=8.0 Hz, 2H), 7.04 (d, J=8.0 Hz, 2H), 4.98 (s, 1H), 3.77-3.09 (m, 8H), 2.97 (s, 2H), 2.83 (s, 3H), 2.26 (s, 1H), 2.01-1.76 (m, 2H), 1.64 (s, 1H), 1.32 (s, 3H), 1.25 (s, 3H); ESI-MS m/z 358.1 $(M+H)^+$.

QY-14-17

$^1$H NMR (400 MHz, DMSO-d6) δ 7.96 (s, 1H), 7.50 (d, J=7.8 Hz, 1H), 7.42-7.30 (m, 3H), 7.08 (d, J=7.7 Hz, 2H), 6.95 (d, J=7.8 Hz, 2H), 6.85 (dd, J=8.1, 2.6 Hz, 1H), 5.02 (dd, J=8.0, 4.2 Hz, 1H), 3.81 (m, 1H), 3.69-3.63 (m, 1H), 2.27 (s, 3H), 2.09-2.01 (m, 1H), 1.73 (m, 2H), 1.57 (s, 3H), 1.53 (m, 1H), 1.50 (s, 3H); ESI-MS m/z 367.1 $(M+H)^+$.

QY-14-24

$^1$H NMR (400 MHz, DMSO-d6) δ 7.54-7.47 (m, 2H), 7.13-7.06 (m, 4H), 6.94 (d, J=7.7 Hz, 2H), 5.00 (dd, J=8.1, 4.9 Hz, 1H), 3.82 (m, 1H), 3.54 (s, 1H), 2.27 (s, 3H), 2.09 (m, 1H), 1.76 (m, 3H), 1.54 (s, 6H); ESI-MS m/z 349.0 $(M+H)^+$.

QY-14-25

$^1$H NMR (400 MHz, DMSO-d6) δ 8.42 (d, J=4.7 Hz, 1H), 7.45 (d, J=7.7 Hz, 1H), 7.38-7.26 (m, 2H), 7.06 (d, J=7.9 Hz, 2H), 6.94 (d, J=7.9 Hz, 2H), 6.85 (dd, J=8.2, 2.5 Hz, 1H), 5.02 (dd, J=8.0, 4.3 Hz, 1H), 3.82 (m, 1H), 3.63 (m, 1H), 2.77 (d, J=4.4 Hz, 3H), 2.27 (s, 3H), 2.05 (m, 1H), 1.73 (m, 2H), 1.57 (s, 3H), 1.53 (m, 1H), 1.50 (s, 3H); ESI-MS m/z 381.1 $(M+H)^+$.

QY-14-27

$^1$H NMR (400 MHz, DMSO-d6) δ 8.78 (s, 1H), 8.25 (s, 1H), 7.96 (s, 1H), 7.38 (s, 1H), 7.07 (d, J=7.7 Hz, 2H), 6.93 (d, J=7.7 Hz, 2H), 4.98 (dd, J=8.1, 4.3 Hz, 1H), 3.38-3.32 (m, 1H), 2.27 (s, 3H), 2.04-1.96 (m, 1H), 1.71 (m, 2H), 1.66 (s, 3H), 1.62 (s, 3H), 1.53-1.47 (m, 1H); ESI-MS m/z 369.2 $(M+H)^+$.

QY-14-29

$^1$H NMR (400 MHz, DMSO-d6) δ 7.08 (d, J=7.9 Hz, 2H), 7.02 (d, J=8.0 Hz, 2H), 4.96 (dd, J=8.3, 4.2 Hz, 1H), 3.49 (m, 1H), 3.42-3.26 (m, 3H), 3.24-3.14 (m, 1H), 2.99 (m, 1H), 2.25 (s, 3H), 2.18 (m, 1H), 1.89 (m, 1H), 1.85-1.64 (m, 5H), 1.60 (m, 1H), 1.28 (s, 3H), 1.19 (s, 3H); ESI-MS m/z 329.2 $(M+H)^+$.

QY-14-30

$^1$H NMR (400 MHz, DMSO-d6) δ 8.48 (d, J=2.8 Hz, 1H), 7.92 (s, 1H), 7.08 (d, J=7.8 Hz, 2H), 6.99 (d, J=7.8 Hz, 2H), 6.66 (t, J=2.2 Hz, 1H), 4.97 (dd, J=8.3, 3.3 Hz, 1H), 3.18 (s, 1H), 2.99 (m, 1H), 2.26 (s, 3H), 1.98 (m, 1H), 1.74-1.62 (m, 2H), 1.54 (m, 1H), 1.51 (s, 3H), 1.46 (s, 3H); ESI-MS m/z 326.1 $(M+H)^+$.

QY-14-31

$^1$H NMR (400 MHz, DMSO-d6) δ 8.12 (s, 1H), 7.08 (d, J=7.7 Hz, 2H), 7.04-6.92 (m, 2H), 4.97 (s, 1H), 3.89-3.05 (m, 8H), 2.25 (s, 3H), 2.16 (m, 1H), 1.80 (s, 2H), 1.60 (s, 1H), 1.31 (s, 3H), 1.22 (d, J=8.7 Hz, 3H); ESI-MS m/z 358.2 $(M+H)^+$.

QY-14-33

$^1$H NMR (400 MHz, DMSO-d6) δ 7.09 (d, J=7.8 Hz, 2H), 7.03 (d, J=7.9 Hz, 2H), 5.00 (dd, J=8.3, 3.9 Hz, 1H), 3.54-2.81 (m, 10H), 2.26 (s, 3H), 2.17 (m, 1H), 1.95-1.79 (m, 2H), 1.68-1.62 (m, 1H), 1.32 (s, 3H), 1.25 (s, 3H); ESI-MS m/z 344.1 $(M+H)^+$.

QY-14-34

$^1$H NMR (400 MHz, DMSO-d6) δ 7.87 (s, 1H), 7.81 (d, J=8.6 Hz, 2H), 7.25 (s, 1H), 7.08 (d, J=7.8 Hz, 2H), 6.95 (d, J=7.8 Hz, 2H), 6.83-6.76 (m, 2H), 5.01 (dd, J=8.1, 4.4 Hz, 1H), 3.77 (m, 1H), 3.61 (m, 1H), 2.28 (s, 3H), 2.04 (m, 1H), 1.78 (m, 1H), 1.66 (m, 1H), 1.56 (s, 3H), 1.52 (s, 3H), 1.50 (s, 1H); ESI-MS m/z 367.2 $(M+H)^+$.

QY-14-35

$^1$H NMR (400 MHz, DMSO-d6) δ 8.82 (s, 1H), 7.78 (s, 1H), 7.07 (d, J=7.7 Hz, 2H), 6.92 (d, J=7.7 Hz, 2H), 5.00-4.92 (m, 1H), 3.56 (mz, 2H), 2.27 (s, 3H), 2.04 (m, 2H), 1.75-1.70 (m, 2H), 1.66 (s, 3H), 1.63 (s, 3H); ESI-MS m/z 351.0 $(M+H)^+$.

QY-14-44

$^1$H NMR (400 MHz, DMSO-d6) δ 7.08 (d, J=7.9 Hz, 2H), 7.02 (d, J=7.8 Hz, 2H), 5.00-4.90 (m, 1H), 3.58 (m, 2H), 3.42-3.15 (m, 4H), 2.25 (s, 3H), 2.17 (m, 1H), 1.85 (m, 2H), 1.67-1.52 (m, 3H), 1.44 (s, 4H), 1.28 (s, 3H), 1.19 (s, 3H); ESI-MS m/z 343.2 $(M+H)^+$.

QY-14-59

$^1$H NMR (400 MHz, DMSO-d6) δ 8.04 (d, J=8.8 Hz, 1H), 7.37 (d, J=2.6 Hz, 1H), 7.17 (dd, J=8.8, 2.6 Hz, 1H), 7.09 (d, J=7.8 Hz, 2H), 6.93 (d, J=7.5 Hz, 2H), 4.97 (dd, J=8.0, 5.1 Hz, 1H), 3.75 (m, 1H), 3.51 (m, 1H), 2.27 (s, 3H), 2.09 (m, 2H), 1.77 (m, 2H), 1.59 (d, J=4.9 Hz, 6H), 1.52 (m, 1H); ESI-MS m/z 374.1 $(M+H)^+$.

QY-14-60

$^1$H NMR (400 MHz, DMSO-d6) δ 7.64 (d, J=9.0 Hz, 1H), 7.20 (d, J=3.0 Hz, 1H), 7.10 (dd, J=12.4, 8.6 Hz, 3H), 6.94 (d, J=7.7 Hz, 2H), 4.99 (dd, J=8.1, 4.9 Hz, 1H), 3.81 (1, 1H), 3.63-3.57 (m, 1H), 2.27 (s, 3H), 2.13-2.07 (m, 1H), 1.78 (m, 2H), 1.56 (m, 1H), 1.54 (s, 6H); ESI-MS m/z 383.2 $(M+H)^+$.

QY-14-68

$^1$H NMR (400 MHz, DMSO-d6) δ 7.44-7.33 (m, 2H), 7.08 (d, J=7.8 Hz, 2H), 6.95 (d, J=7.8 Hz, 2H), 6.79-6.73 (m, 2H), 5.01 (dd, J=8.2, 4.4 Hz, 1H), 4.08 (s, 1H), 3.76 (m, 1H), 3.62 (m, 1H), 2.28 (s, 3H), 2.05 (m, 1H), 1.72 (m, 2H), 1.55 (s, 3H), 1.50 (s, 3H), 1.48 (m, 1H); ESI-MS m/z 348.1 $(M+H)^+$.

QY-15-11

$^1$H NMR (400 MHz, DMSO-d6) δ 7.31-7.24 (m, 2H), 7.08 (d, J=7.6 Hz, 2H), 6.96 (d, J=7.7 Hz, 2H), 6.75 (d, J=8.8 Hz, 2H), 5.40 (s, 1H), 5.00 (dd, J=8.1, 4.3 Hz, 1H), 3.76 (m, 1H), 3.63 (m, 1H), 2.28 (s, 3H), 2.04 (m, 1H), 1.65 (m, 2H), 1.55 (s, 3H), 1.49 (s, 3H), 1.44 (m, 1H), 1.37 (s, 6H); ESI-MS m/z 406.2 $(M+H)^+$.

QY-15-12

$^1$H NMR (400 MHz, DMSO-d6) δ 8.83 (dd, J=2.3, 1.0 Hz, 1H), 8.74 (dd, J=2.1, 1.0 Hz, 1H), 8.66 (dd, J=4.9, 1.7 Hz, 1H), 8.58 (dd, J=4.9, 1.7 Hz, 1H), 8.07 (dt, J=7.9, 1.9 Hz, 1H), 7.96 (dt, J=8.0, 1.9 Hz, 1H), 7.10 (d, J=7.8 Hz, 2H), 6.97 (d, J=7.8 Hz, 2H), 6.86-6.79 (m, 2H), 5.02 (dd, J=8.1, 4.3 Hz, 1H), 3.78 (m, 1H), 3.64 (m, 1H), 2.28 (s, 3H), 2.06 (m, 1H), 1.80 (m, 1H), 1.67 (m, 1H), 1.57 (s, 3H), 1.53 (s, 3H), 1.51 (m, 1H); ESI-MS m/z 425.1 $(M+H)^+$.

QY-15-31

$^1$H NMR (400 MHz, DMSO-d6) δ 7.31 (dd, J=9.0, 2.5 Hz, 2H), 7.08 (d, J=7.8 Hz, 2H), 6.96 (d, J=7.8 Hz, 2H), 6.77-6.70 (m, 2H), 5.01 (dd, J=8.1, 4.3 Hz, 1H), 3.75 (dt, J=11.1, 7.0 Hz, 1H), 3.64 (dt, J=11.6, 6.4 Hz, 1H), 3.19-3.15 (m, 2H), 2.93 (m, 3H), 2.28 (s, 3H), 2.01 (m, 3H), 1.72 (m, 5H), 1.55 (s, 3H), 1.49 (s, 3H); ESI-MS m/z 431.2 $(M+H)^+$.

XHJ-3-22

$^1$H NMR (400 MHz, DMSO-d6) δ 7.52 (m, 1H), 7.19-7.13 (m, 1H), 7.09 (d, J=8.1 Hz, 2H), 6.98 (d, J=8.0 Hz, 2H), 6.78 (t, J=9.0 Hz, 1H), 5.03 (dd, J=8.0, 4.4 Hz, 1H), 3.89-3.69 (m, 2H), 2.10 (m, 1H), 1.93-1.69 (m, 3H), 1.56 (s, 3H), 1.48 (s, 3H); ESI-MS m/z 379.0 $(M+H)^+$.

ZSQ-13-56

$^1$H NMR (400 MHz, DMSO-d6) δ 7.41 (m, 1H), 7.35-7.24 (m, 4H), 7.11-7.03 (m, 2H), 6.95 (m, 1H), 6.71 (t, J=9.0

Hz, 1H), 5.36 (m, 1H), 3.39 (m, 1H), 2.62 (m, 1H), 1.63 (d, J=7.7 Hz, 6H); ESI-MS m/z 361.1 $(M+H)^+$.

ZSQ-13-57

$^1$H NMR (400 MHz, DMSO-d6) δ 7.41 (m, 1H), 7.28 (s, 1H), 7.18-7.08 (m, 4H), 6.97 (m, 1H), 6.70 (t, J=9.0 Hz, 1H), 5.38 (dd, J=11.7, 4.7 Hz, 1H), 3.39-3.33 (m, 1H), 2.64 (m, 1H), 1.62 (d, J=7.4 Hz, 6H); ESI-MS m/z 378.9 $(M+H)^+$.

Biological Test Example 1. Cell Necrosis Inhibitory Activity Test for RIPK1 Inhibitor The adopted biological assay protocol was: the programmed necroptosis effect of compounds on TNF-induced in FADD (Fas-Associated Death Domain) deficient Jurkat cells and L929 cells.

In order to verify the inhibitory effect of the compounds of the present invention on programmed cell necrosis at the cellular level, cell types closely related to the RIP1 pathway, namely FADD deficient Jurkat cells (human peripheral blood leukemia T cell line) and L929 cells, were selected. Two different stimulation methods were used: tumor necrosis factor (TNFα) used alone, or TNFα used in combination with mitochondria-derived cysteine aspartate activator (SMAC). Cells viability was calculated by detecting chemiluminescence values, and the biological activity of the compound for inhibiting programmed cell necrosis can be obtained.

Methods: FADD deficient Jurkat cells: FADD deficient Jurkat cells (human peripheral blood leukemia T cell line) were cultured in vitro. After growing to the logarithmic growth phase, the cells were collected, centrifuged at 1000 rpm for 5 min, the supernatant was discarded, and the cell concentration was adjusted to $2.5\times10^5$/mL. Cells were seeded into 384-well plates, 40 μl per well. 5 μL of Smac (50 nM) diluted in cell culture medium and 5 μL of each compound were added to the corresponding wells. After pretreatment at 37° C. for 1 h, 5 μL of TNFα (50 ng/mL) diluted in cell culture medium was added to each well of the stimulation group, and 5 μL of the culture medium was added to the control group. The plate was cultured in a cell incubator (37° C., 5% $CO_2$) for 14 h, and 15 μl of Cell Titer-Glo solution was added to each well, then incubated for 30 min at room temperature, and intracellular ATP level was measured by detecting luminescence. The unstimulated DMSO control wells were taken as 100% cell viability. L929 cells: The L929 cells (mouse fibroblasts) were cultured in vitro, digested and diluted to $6.25\times10^4$/ml, and the cells were seeded into 384-well plates, 40 μl per well. The plate was placed in a cell incubator (37° C., 5% $CO_2$) for 12 hours. 5 μL of Smac (500 nM) diluted in cell culture medium and 5 μL of each compound were added to the corresponding wells. After pretreatment at 37° C. for 1 h, 5 μL of TNFα (500 ng/mL) diluted in cell culture medium was added to each well of the stimulation group, and 5 μL of the culture medium was added to the control group. After the plate was cultured for 14 h in a cell incubator (37° C., 5% $CO_2$), 15 μl of Cell Titer-Glo solution was added to each well. The plate was incubated at room temperature for 30 min, and intracellular ATP level was measured by detecting luminescence. The unstimulated DMSO control wells were taken as 100% cell viability. $EC_{50}$ values of the compounds were calculated using Prism Graphpad statistical software.

TABLE 1

The inhibitory activity test results of RIPK1 inhibitor on programmed cell necrosis

| Compound | $EC_{50}$ (μM) | | | |
|---|---|---|---|---|
| | FADD−/− Jurkat cells (human) | | L929 cells (mouse) | |
| number | TNFa | TNFa + SM164 | TNFa | TNFa + SM164 |
| 7-Cl-O-Nec-1 (Nec-1s) | 0.076 | 0.337 | 0.155 | 0.924 |
| QY-1-98 | 0.128 | 1.528 | 0.213 | 1.289 |
| QY-2-100 | 2.244 | >10 | 2.48 | >10 |
| QY-2-103 | >10 | >10 | >10 | >10 |
| QY-2-104 | >10 | >10 | >10 | >10 |
| QY-2-25 | 6.179 | >10 | 2.67 | >10 |
| QY-2-26 | 0.417 | >10 | 0.182 | 0.982 |
| QY-2-27 | 9.383 | >10 | >10 | >10 |
| QY-2-34 | >10 | >10 | >10 | >10 |
| QY-2-38 | 1.698 | >10 | 1.547 | >10 |
| QY-2-39 | 1.063 | >10 | 1.904 | 8.919 |
| QY-2-52 | 0.464 | 2.24 | 0.419 | 2.37 |
| QY-2-53 | 0.199 | 1.344 | 0.172 | 1.173 |
| QY-2-54 | >10 | >10 | 6.19 | >10 |
| QY-2-55 | 0.14 | 2.218 | 0.025 | 0.233 |
| QY-2-56 | >10 | >10 | 2.115 | >10 |
| QY-2-75 | 0.608 | 5.152 | 2.452 | >10 |
| QY-2-76 | >10 | 3.962 | >10 | >10 |
| QY-2-77 | 7.904 | >10 | 4.259 | >10 |
| QY-2-78 | 0.127 | >10 | >10 | >10 |
| QY-2-79 | 2.028 | 8.925 | 0.212 | 1.618 |
| QY-3-11 | 0.389 | 3.271 | 0.404 | 1.567 |
| QY-3-17 | 3.908 | >10 | 5.377 | 52.41 |
| QY-3-26 | 0.111 | 1.275 | 0.196 | 1.236 |
| QY-3-27 | 0.056 | 0.849 | 0.133 | 0.792 |
| QY-3-28 | 5.552 | >10 | 0.878 | 4.085 |
| QY-3-29 | 0.035 | 0.664 | 0.047 | 0.157 |
| QY-3-35 | 10.52 | >10 | 160.4 | >10 |
| QY-3-36 | 0.983 | 8.355 | 2.25 | 9.404 |
| QY-3-39 | 0.712 | 5.282 | 0.386 | 1.477 |
| QY-3-4 | >10 | >10 | >10 | 59.13 |

TABLE 1-continued

The inhibitory activity test results of RIPK1 inhibitor on programmed cell necrosis

| Compound | EC$_{50}$ (μM) | | | |
|---|---|---|---|---|
| | FADD−/− Jurkat cells (human) | | L929 cells (mouse) | |
| number | TNFa | TNFa + SM164 | TNFa | TNFa + SM164 |
| QY-3-46 | 0.789 | 5.826 | 2.013 | >10 |
| QY-3-51 | 59.24 | >10 | >10 | >10 |
| QY-3-65 | >10 | >10 | >10 | >10 |
| QY-3-81 | 0.326 | 1.962 | 0.704 | 2.723 |
| QY-3-86 | 13.46 | 8.676 | >10 | >10 |
| QY-3-94 | 0.516 | 2.955 | 1.411 | 5.225 |
| QY-3-95 | 0.102 | 1.141 | 0.135 | 1.004 |
| QY-3-96 | 2.789 | 9.223 | >10 | >10 |
| QY-3-99 | 0.061 | 0.444 | 0.062 | 0.244 |
| QY-4-1 | 10.34 | >10 | 12.7 | >10 |
| QY-4-11 | 0.061 | 1.706 | >10 | >10 |
| QY-4-12 | 0.607 | 5.886 | 1.608 | 9.534 |
| QY-4-14 | 17.97 | 40.59 | 5.89 | >10 |
| QY-4-2 | 1.061 | 7.726 | 3.946 | 16.91 |
| QY-4-27 | 2.901 | >10 | 3.666 | >10 |
| QY-4-3 | >10 | >10 | >10 | >10 |
| QY-4-32 | 0.712 | 2.676 | 0.52 | 1.648 |
| QY-4-35 | 4.088 | >10 | 3.703 | >10 |
| QY-4-39 | 0.274 | 1.186 | 0.189 | 0.675 |
| QY-4-6 | 0.116 | 0.776 | 0.065 | 0.292 |
| QY-4-66 | 0.544 | 2.188 | 0.392 | 1.277 |
| QY-4-67 | 1.332 | 5.159 | 1.385 | 3.927 |
| QY-4-69 | 1.541 | 9.381 | 0.65 | 3.627 |
| QY-4-7 | 0.126 | 0.825 | 0.111 | 0.652 |
| QY-4-70 | >10 | >10 | 1.776 | >10 |
| QY-4-75 | 0.083 | 0.704 | 0.043 | 0.188 |
| QY-4-78 | 0.205 | 1.104 | 0.156 | 0.724 |
| QY-4-8 | 0.091 | 0.568 | 0.05 | 0.139 |
| QY-4-87 | 2.375 | >10 | 2.395 | >10 |
| QY-4-88 | 0.746 | 4.003 | 1.155 | 3.096 |
| QY-4-96 | 1.465 | 6.933 | 2.096 | 8.128 |
| QY-4-99 | 1.447 | 9.203 | 2.507 | 9.121 |
| QY-5-1 | >10 | >10 | >10 | >10 |
| QY-5-21 | 0.093 | 0.696 | 0.0599 | 0.208 |
| QY-5-22 | 0.098 | 0.683 | 0.062 | 0.262 |
| QY-5-4 | >10 | >10 | >10 | >10 |
| QY-5-79 | 9.229 | 1.062 | >10 | >10 |
| QY-5-83 | 1.291 | 7.724 | 8.752 | >10 |
| QY-5-85 | 5.345 | >10 | >10 | >10 |
| QY-6-47 | 0.005 | 0.09 | 0.018 | 0.049 |
| QY-6-48 | >10 | 0.153 | >10 | >10 |
| QY-6-60 | 0.017 | 0.707 | 0.13 | 0.402 |
| QY-6-61 | 0.012 | 0.379 | 0.075 | 0.218 |
| QY-6-62 | 0.003 | 0.117 | 0.044 | 0.174 |
| QY-6-63 | 4.292 | >10 | 3.15 | 7.805 |
| QY-6-83 | 0.056 | 0.613 | 0.04 | 0.323 |
| QY-6-84 | 0.027 | 0.439 | 0.025 | 0.216 |
| QY-7-7 | 0.005 | 0.2 | 0.001 | 0.024 |
| XHJ-3-22 | 0.177 | 1.457 | 0.04 | 0.302 |
| ZSQ13-56 | 0.049 | 0.424 | 0.028 | 0.201 |
| ZSQ13-57 | 0.026 | 0.37 | 0.01 | 0.112 |
| QY-7-101 | 0.63 | 1.1 | 0.011 | 0.01 |
| QY-8-101 | 0.015 | 0.692 | 0.0058 | 0.015 |
| QY-9-8 | 0.00043 | 0.0016 | 0.00044 | 0.138 |
| QY-9-32 | 0.0266 | 0.842 | 0.0357 | |
| QY-9-43 | 0.00016 | 1.15 | 0.021 | |
| QY-10-1 | >10 | >10 | 0.00079 | 0.0036 |
| QY-10-92 | >10 | >10 | >10 | >10 |
| QY-10-96 | 0.01344 | 0.633 | 0.0001508 | 0.006307 |
| QY-10-104 | 0.1063 | 0.794 | 0.01364 | 0.06623 |
| QY-11-1 | 0.004047 | 0.000000297 | 0.00008034 | 0.00266 |
| QY-11-9A | >10 | >10 | 2.53 | >10 |
| QY-11-9B | 2.83 | 3.34 | 0.000001713 | 3.44 |
| QY-11-11A | >10 | >10 | 0.00001883 | 0.0000772 |
| QY-11-11B | >10 | >10 | 0.00001924 | 0.0001197 |
| QY-11-15B | >10 | >10 | >10 | >10 |
| QY-11-16A | >10 | >10 | >10 | >10 |
| QY-11-16B | >10 | >10 | >10 | >10 |
| QY-11-36 | 0.1366 | 0.8852 | | 0.09951 |
| QY-11-44 | 0.2123 | 1.318 | 0.00001052 | 0.6772 |
| QY-11-45 | 0.1391 | 0.9148 | 0.0007005 | 0.1081 |
| QY-12-11 | 0.006717 | 0.1785 | 0.006061 | 0.01661 |

TABLE 1-continued

The inhibitory activity test results of RIPK1 inhibitor on programmed cell necrosis

| Compound | $EC_{50}$ (μM) | | | |
|---|---|---|---|---|
| | FADD−/− Jurkat cells (human) | | L929 cells (mouse) | |
| number | TNFa | TNFa + SM164 | TNFa | TNFa + SM164 |
| QY-12-14 | 0.003654 | 0.04529 | 0.003161 | 0.007633 |
| QY-12-32 | 0.5352 | 2.416 | 0.2426 | 1.163 |
| QY-13-42 | 0.00003949 | 4.9 | 0.1023 | 0.3221 |
| QY-13-68 | 0.02698 | 2.42 | 0.002057 | 0.004518 |
| QY-13-70 | 0.4769 | >10 | 0.2208 | 1.93 |
| QY-13-86 | >10 | >10 | >10 | >10 |
| QY-14-8 | >10 | >10 | >10 | >10 |
| QY-14-9 | >10 | >10 | >10 | >10 |
| QY-14-17 | >10 | >10 | >10 | >10 |
| QY-14-24 | 0.02195 | 0.9389 | 0.01543 | 0.06596 |
| QY-14-25 | >10 | >10 | >10 | >10 |
| QY-14-27 | >10 | >10 | 8.45 | >10 |
| QY-14-29 | >10 | >10 | >10 | >10 |
| QY-14-30 | >10 | >10 | 4.89 | >10 |
| QY-14-31 | >10 | >10 | >10 | >10 |
| QY-14-33 | >10 | >10 | >10 | >10 |
| QY-14-34 | 2.358 | >10 | 0.8162 | >10 |
| QY-14-35 | >10 | >10 | >10 | >10 |
| QY-14-40 | >10 | >10 | >10 | >10 |
| QY-14-44 | >10 | >10 | >10 | >10 |
| QY-14-59 | 4.569 | >10 | 0.4671 | >10 |
| QY-14-60 | 0.2826 | 1.619 | 0.1412 | 0.4969 |
| QY-14-68 | 0.01725 | 0.1796 | 0.021 | 0.1019 |
| QY-15-11 | >10 | >10 | 2.843 | >10 |
| QY-15-12 | >10 | >10 | 5.16 | >10 |
| QY-15-31 | 0.8178 | >10 | 0.08242 | >10 |

Biological Test Example 2. Effects of Compounds on TNF-Induced FADD (Fas-Associated Death Domain) Deficient Jurkat Cells and L929 Cells Programmed Necrosis In order to verify the inhibitory effect of the compounds of the present invention on programmed cell necrosis at the cellular level, cell types closely related to the RIP1 pathway, namely FADD deficient Jurkat cells (human peripheral blood leukemia T cell line) and L929 cells, were selected. Two different stimulation methods were used: tumor necrosis factor (TNFα) used alone, or TNFα used in combination with mitochondria-derived cysteine aspartate activator (SMAC). Cells viability was calculated by detecting chemiluminescence values, and thus obtaining the biological activity of the compound to inhibit programmed necrosis of cells.

Studies have found that apoptosis-inducing cytokines can also induce cell necrosis when caspase activity is inhibited. For example, in mouse L929 (mouse fibrosarcoma cells), TNFα stimulate cell necrosis; after inhibition of Caspase activity with the broad-spectrum caspase inhibitor Z-VAD-FMK, TNFR1, FasR1 and TRAIL signaling pathways can all induce Jurkat (Human T cell lines) undergo cell necrosis, and the process of cell necrosis depends on the kinase activity of serine/threonine protein kinase 1 (RIPK1); the activation of Caspase-8 needs to be recruited by FADD (Fas-associated death domain), and in the absence of FADD In Jurkat cells, stimulation with TNFα also resulted in cell necrosis. In addition, studies have shown that the mitochondrial intermembrane space protein analog Smac can accelerate the necrosis process, and the co-induction of necrosis in vitro with high doses of TNF, Smac analogs and the pan-caspase inhibitor z-VAD-FMK may bypass or mask the role of mitochondria in the execution of necrosis.

The adopted biological assay protocol was: the programmed necroptosis effect of compounds on TNF-induced necroptosis in FADD (Fas-Associated Death Domain) deficient Jurkat and L929 (murine) cells.

In order to verify the inhibitory effect of the compounds of the present invention on programmed cell necrosis at the cellular level, FADD deficient Jurkat cells (human peripheral blood leukemia T cell line) and L929 cells (mouse fibroblasts) were selected, and TNF and SMAC were used. The cell viability was calculated by detecting the chemiluminescence value, and the biological activity of the compound for inhibiting programmed cell necrosis can be obtained.

Experimental Conditions and Procedures

FADD deficient Jurkat cells: FADD deficient Jurkat cells (human peripheral blood leukemia T cell line) were cultured in vitro. After growing to the logarithmic growth phase, the cells were collected, centrifuged at 1000 rpm for 5 min, the supernatant was discarded, and the cell concentration was adjusted to $2.5\times10^5$/mL. Cells were seeded into 384-well plates, 40 μl per well. 5 μL of Smac (50 nM) diluted in cell culture medium and 5 μL of each compound were added to the corresponding wells. After pretreatment at 37° C. for 1 h, 5 μL of TNFα (50 ng/mL) diluted in cell culture medium was added to each well of the stimulation group, and 5 μL of the culture medium was added to the control group. After the plate was cultured in a cell incubator (37° C., 5% $CO_2$) for 14 h, 15 μl of Cell Titer-Glo solution was added to each well. The mixture was incubated for 30 min at room temperature, and intracellular ATP level was measured by detecting luminescence. The unstimulated DMSO control wells were taken as 100% cell viability.

L929 cells: The L929 cells (mouse fibroblasts) were cultured in vitro, digested and diluted to $6.25\times10^4$/ml, and the cells were seeded into 384-well plates, 40 μl per well. The plate was placed in a cell incubator (37° C., 5% $CO_2$) for 12 hours. 5 μL of Smac (500 nM) diluted in cell culture medium and 5 μL of each compound were added to the corresponding wells. After pretreatment at 37° C. for 1 h, 5 μL of TNFα (500 ng/mL) diluted in cell culture medium was added to each well of the stimulation group, and 5 μL of the culture medium was added to the control group. After the plate was cultured for 14 h in a cell incubator (37° C., 5% $CO_2$), and 15 μl of Cell Titer-Glo solution was added to each well, then incubated at room temperature for 30 min, and intracellular ATP level was measured by detecting luminescence. The unstimulated DMSO control wells were taken as 100% cell viability.

The results are shown in FIG. 1. The results show that the compounds of the present invention can effectively ameliorate TNF-induced FADD (Fas-related death domain) deficient Jurkat cells and L929 cells programmed necrosis.

Biological Test Example 3. The Effect of Compound QY-1-98 on Key Proteins in TNF α-Induced FADD Deficient Jurkat Cell Programmed Necrosis Pathway Necroptosis induced by TNFα is mediated by a complex called Necrosome (Complex IIb), which includes TRADD, FADD, Caspase-8, RIPK1, RIPK3 and MLKL. The kinase activity of RIPK1 has been shown to play a critical role in the regulation of programmed cell necrosis. During programmed cell necrosis, RIPK1 undergoes autophosphorylation activation, with serine 166 is one of the main phosphorylation sites. After programmed cell necrosis occurs, oligomeric MLKL translocates to the cell membrane and mediates cell death by calcium influx.

In order to verify whether the compounds of the present invention can inhibit programmed cell death by inhibiting the activity of RIPK1, and to detect the activation of downstream proteins of programmed necrosis pathway, TNFα was used to stimulate FADD deficient Jurkat to produce programmed necrosis, and the compounds of the present invention were used to treat the cells at the same time. Cells were harvested after a period of time to detect phosphorylation of RIPK1 and oligomerization of MLKL using western blot.

Experimental Conditions and Procedures

FADD deficient Jurkat cells (human peripheral blood leukemia T cell line) were cultured in vitro. After growing to the logarithmic growth phase, the cells were collected, centrifuged at 1000 rpm for 5 min, the supernatant was discarded, and the cell concentration was adjusted to $1\times10^6$/mL. In a 12-well cell culture plate, 1 ml of cells was added to each well, and 0.2 μL of DMSO solution containing a concentration of 50 mM drug or pure DMSO as control was added to each well. The mixture was pretreated for 1 hour. 0.5 μL of 100 μg/ml TNFα (PBS solution) was added to each group of stimulation group. After the plate was cultured in a cell incubator (37° C., 5% $CO_2$) for 4 hours, the cells were collected by centrifuging at 3000 rpm for 3 min and washed with pre-cooled PBS solution for two times. The supernatant was removed as much as possible, and 200 μL of RIPA cell lysate was added to the cell pellet. The mixture was placed on a shaker at 4° C. for 30 minutes, and then centrifuged at 15,000 rpm for 15 minutes at 4° C. to obtain the supernatant cell lysate. The BCA protein quantification kit was used to detect the protein content of each group, and PIPA lysis buffer was used to adjust the protein amount to make the final volume of 100 μL. Samples were identified by western-blot.

Western-Blot:

25 μL of 5* protein loading buffer was added to 100 μL of cell lysate, and the mixture was heated at 95° C. for 10 min After the samples were cooled, electrophoresis was carried out using SDS-PAGE (9%) gel at 60V, and then switched to 120V after 30 min until the leading band was electrophoresed to the bottom of the gel. Using a turbo semi-dry transfer system with a constant current of 0.2 A to transfer for 80 minutes, the proteins in the gel were transferred to a PC membrane with a pore size of 0.2 μL. The transferred PC membrane was placed in 5% skim milk powder (TBST solution) for blocking for 2H, and incubated with the corresponding primary antibody at 4° C. for 12H, and washed with TBST for 3 times, 10 min each time. The sample was incubated with the corresponding secondary antibody for 2H at room temperature, washed with TBST three times, 10 min each time. The resulting sample was incubated with ECL luminescent solution and detected the luminescent signal.

Figure 2:
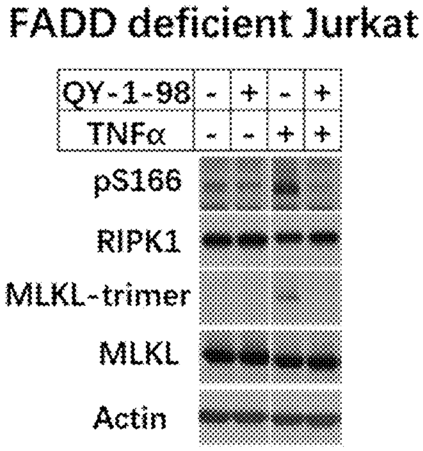
FIG. 2 shows the effect of compound QY-1-98 on key proteins in the TNFα-induced FADD deficient Jurkat cell programmed necrosis pathway in Example 3.

FIG. 2 shows the effect of compound QY-1-98 on key proteins in the TNFα-induced FADD deficient Jurkat cell programmed necrosis pathway. The experimental results show that compound QY-1-98 can inhibit the phosphorylation of RIPK1 and the oligomerization of MLKL, which together indicate that compound QY-1-98 can inhibit the activation of key proteins in programmed cell necrosis.

Biological Test Example 4. The Test Results of the Effect of Compound QY-1-98 on the Thermal Stability of RIPK1 (1-330) Protein The interaction between RIPK1 protein and compound was analyzed by studying the thermal stability of the protein. Small molecule ligands can stabilize proteins by binding to proteins, increasing the $T_m$ value of proteins. The interaction between the compound and the protein can be indirectly judged by testing the effect of the compound on the thermal stability of the protein. RIPK1 protein contains kinase domain (1-312), intermediate domain (312-582) and death domain (582-669), and RIPK1 (1-330) protein purified in vitro contains all kinase domains.

The adopted biological test protocol was to test the effect of compound QY-1-98 on the thermal stability of RIPK1 (1-330) protein using protein thermal shift assay, using the known RIPK1 inhibitor Nec-1s as a control.

Experimental Conditions and Procedures

RIPK1(1-330) protein (final concentration 2 μM) was expressed and purified in insect cells, mixed with the corresponding concentration of compound and SYRO Orange Protein gel stain dye (final concentration 5×). 10 μL of final volume was added to 384-well plate, and at least 3 duplicate wells were set in each group. After the samples were placed for 2 hours at room temperature, the 7500 Fast Real-Time PCR System was applied to test the thermal stability of the protein by differential scanning calorimetry. The temperature was set at 25° C.-95° C., 0.015° C./s. The datas were analyzed using protein thermal shift software.

Figure 3:
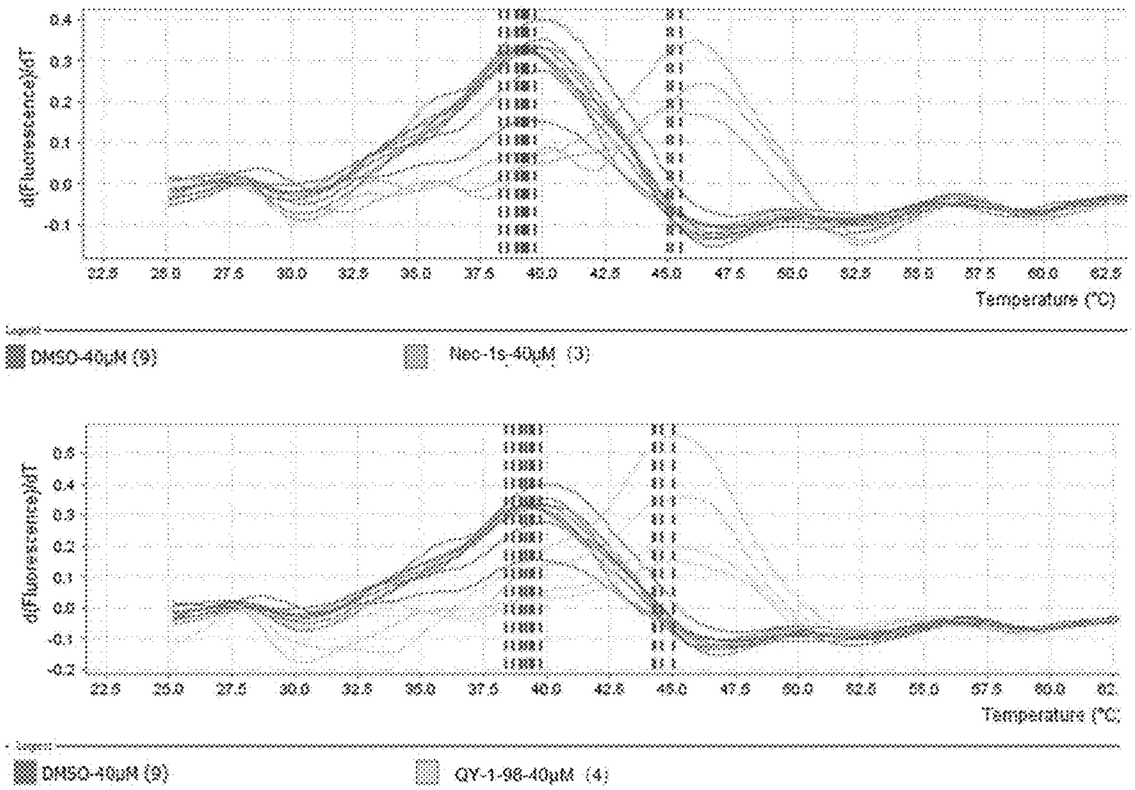
FIG. 3 shows the test results of the effect of compound QY-1-98 on the thermal stability of RIPK1 (1-330) protein in Example 4.

FIG. 3 shows the test results of the effect of compound QY-1-98 on the thermal stability of RIPK1(1-330) protein. The experimental results show that compound QY-1-98 can significantly improve the thermal stability of RIPK1 (1-330)

protein, which proves that compound QY-1-98 can be directly bind to RIPK1(1-330) protein in vitro.

Biological Test Example 5. The Effect of Compound QY-1-98 on the Kinase Activity of RIPK1(1-330) Protein The process of in vitro kinase reaction is related to the substrate concentration. The effect of substrate-competitive inhibitors will change drastically with the change of substrate concentration, while the effect of substrate-noncompetitive inhibitors does not change with the change of substrate concentration. ATP-competitive kinase inhibitors inhibit kinase activity by competing with ATP for the binding site, and ATP-competitive kinase inhibitors are generally less specific due to the conservation of ATP binding sites. In contrast, ATP-noncompetitive kinase inhibitors generally have higher specificity.

The adopted biological test protocol was: The effect of compound QY-1-98 on the kinase activity of RIPK1(1-330) protein was tested. The purified RIPK1(1-330) protein in vitro retained the complete kinase activity domain and maintained good kinase activity. Through the $IC_{50}$ of the compounds of the present invention inhibiting RIPK1 kinase activity in the environment with different concentrations of ATP, the binding mode of the compounds to RIPK1 is obtained. Nec-1s, a known ATP-noncompetitive inhibitor of RIPK1, was used as a control.

Experimental Conditions and Procedures

RIPK1(1-330) protein with a final concentration of 2 μL and ATP (1× kinase buffer) with a corresponding concentration were added to the 384-well plate, with a final concentration of 5 μL. At least 3 duplicate wells were set in each group. The reaction was carried out at 37° C. for 2H. 5 μL of ADP-Glo reagent was added, which is used to stop the kinase reaction and remove residual ATP from the reaction system. The reaction solution was placed at room temperature for 40 min 10 μL of kinase detection reagent was added, which is used to convert ADP to ATP and luciferase and luciferin were introduced to detect ATP in the system. The reaction was carried out at room temperature for 1H. Luminescence was detected using the 7500 Fast Real-Time PCR System. The $IC_{50}$ of the compounds inhibiting the kinase reaction was calculated using Prism Graphpad statistical software.

Figure 4:
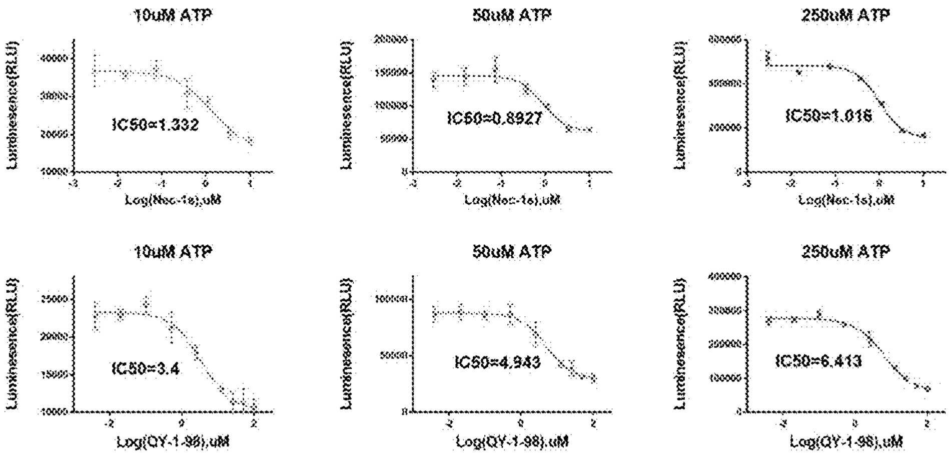
FIG. 4 shows the test results of the effect of the tested compound QY-1-98 on the kinase activity of RIPK1 (1-330) protein in Example 5.

FIG. 4 shows the kinase activity results of the effect of the tested compound QY-1-98 on RIPK1(1-330) protein. The experimental results show that the compound QY-1-98 can inhibit the activity of RIPK1 (1-330) protein kinase in vitro, and the $IC_{50}$ does not change significantly with the increase of ATP concentration. The compound in the present patent may be a kind of ATP-noncompetitive kinase inhibitor.

Biological Test Example 6. The Effect of Mutation of Serine at Position 161 of RIPK1 to Alanine (S161A) on the Compound Nec-1s binds to a hydrophobic pocket between the N-lope and C-lope of RIPK1 and is tightly bound by van der Waals force, hydrophobic interaction and hydrogen bonding. The serine at position 161 of RIPK1 forms a hydrogen bond interaction with the indole ring of Nec-1s. After mutating serine 161 to alanine, the binding of Nec-1s to RIPK1 was greatly weakened.

The biological test protocol used in this experiment was to test the effect of mutation of serine at position 161 of RIPK1 to alanine on the activity of compound QY-1-98. The experiment was verified by two aspects. On the one hand, after RIPK1 was overexpressed in 293T cells, RIPK1 would be activated by autophosphorylation, and the activity of small molecules to inhibit the phosphorylation of RIPK1 was detected at this time. On the other hand, in murine-derived MEFs cells with RIPK1 knockout, and RIPK1 (S161A) put back, RIPK1-dependent cell apoptosis can be induced by using TNFα and 5z7 (TAK1 inhibitor), and the effect of the compound to inhibit cell death was detected at this time.

The structure of 5z7 is shown in the following formula:

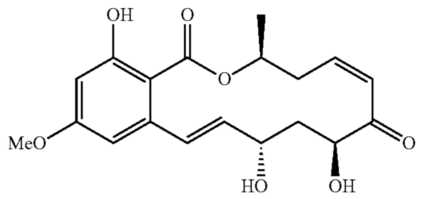 [SMILES: COc1cc(O)c2c(c1)/C=C/[C@@H](O)C[C@H](O)C(=O)/C=C\C[C@H](C)OC2=O]

Experimental Conditions and Procedures 1. 293T cells overexpressing RIPK1 experiment: RIPK1 plasmid with N-terminal 3×FLAG was constructed on PcDNA vector. 293T cells were digested, and then diluted to $8\times10^5$/ml. 1 ml of cells were added to each well of a 12-well cell culture plate, and the plate was placed in a cell culture incubator (37° C., 5% $CO_2$) for 12 hours before transfection. In 100 μL of serum-free medium, 1 μg of RIPK1 plasmid or empty vector and 3 μL of PEI transfection reagent were added respectively, and the mixture was mixed well, and allowed to stand at room temperature for 15 minutes, and then slowly added dropwise into the 12-well plate. The plate was placed in cell incubator for 12 h. The supernatant medium was aspirated and the cells were gently washed twice with pre-chilled PBS to prevent the cells from being blown up. The PBS was aspirated and lysed with 400 μL of pre-chilled RIPA lysis buffer for 30 min on a 4° C. shaker. The cell lysate was centrifuged at 15,000 rpm at 4° C. for 15 minutes, the supernatant was removed, 2× protein loading buffer was added, and the cells were heated at 95° C. for 10 minutes. After cooling, the samples were detected by western-blot after electrophoresis on SDS-PAGE gel (9%). 2. Detection of compound inhibiting RIPK1 (S161A) cell death: S161A MEFs cells were digested and then diluted to $6.25\times10^4$/ml, and the cells were seeded into 384-well plates, 40 μl per well. The plate was placed in a cell incubator (37° C., 5% $CO_2$) for 12 hours. 5z7 (3 μM) diluted in cell culture medium and 5 μl of compound (100 μM) were added to the corresponding wells. After pretreatment at 37° C. for 1 h, 5 μL of TNFα (500 ng/mL) diluted in cell culture medium was added to each well of the stimulation group. 5 μL of culture medium was added to the control group. The plate was placed in cell incubator (37° C., 5% $CO_2$) for 14 h, 15 μl of Cell Titer-Glo solution was added to each well, the mixture was incubated at room temperature for 30 min, and the luminescence value was detected to measure the level of intracellular ATP. The unstimulated DMSO control well was taken as 100% cell viability. At least three duplicate wells were set in each group.

Figure 5:
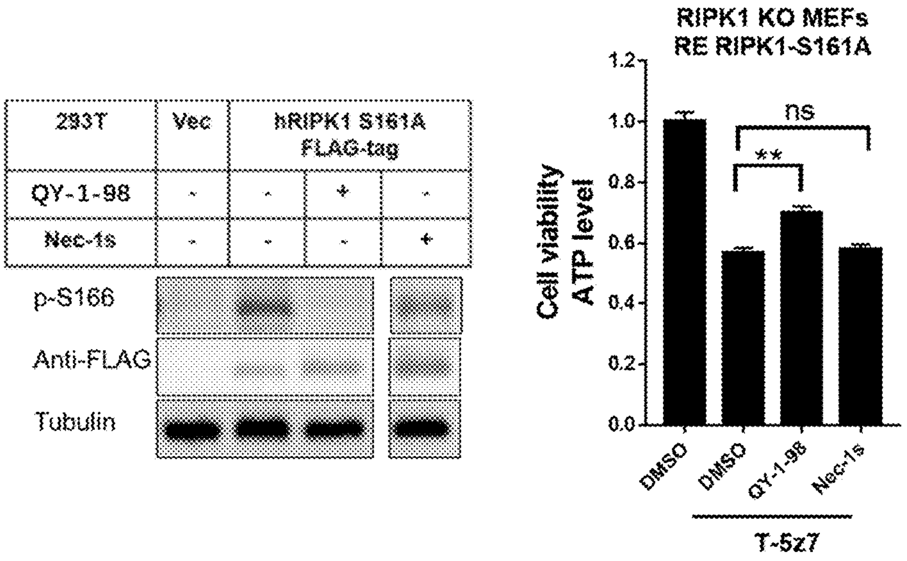
FIG. 5 shows the test result of the effect of the mutation of serine at position of 161 of RIPK1 to alanine (S161A) on the compound in Example 6.

The results are shown in FIG. 5. The experimental results show that the compound QY-1-98 can still inhibit the programmed cells necrosis after the 161 serine of RIPK1 is mutated to alanine.

Biological Test Example 7. The Effect of Mutation of Serine 161 of RIPK1 to Glutamic Acid on the Compound Mutation of serine 161 of RIPK1 to glutamic acid can mimic the phosphorylation of RIPK1, where RIPK1 is always in the activated conformation. Nec-1, on the other hand, can only act on the inactive conformation of RIPK1.

The biological test protocol used in this experiment was to test the effect of serine mutation at position 161 of RIPK1 to glutamic acid on the activity of the compound. The experiment was verified by two aspects. On the one hand, the mouse-derived MEFs cells in which RIPK1 (S161E) was put back after knocking out RIPK1 were treated with the compound of the present invention, and the phosphorylation state of RIPK1 was detected by western-blot; on the other hand, whether the compounds of the present invention have inhibitory effect on RIPK1-dependent apoptosis in the above-mentioned S161E cells was detected.

Experimental Conditions and Procedures

1. S161E MEFs cells were digested, and then diluted to $1.5\times10^5$/ml, and the cells were seeded into 6-well plates with 2 ml per well. The plate was placed in a cell incubator (37° C., 5% $CO_2$) for 12 hours. 0.4 μL of compound 4-8 (50 mM in DMSO) or 0.4 μL of Nec-1s (50 μM in DMSO) was added to the wells respectively, 0.4 μL of DMSO was added to the control group. After pretreatment at 37° C. for 1 h, 1 μL of TNFα (100 μg/ml) was added to each well, and the plate was placed in the cell incubator (37° C., 5% $CO_2$) for 2 h. The supernatant was aspirated and the cells were gently washed twice with PBS to remove residual PBS as much as possible. 150 μL of RIPA cell lysate was added to the cells, the cells were placed on a shaker at 4° C. for 30 minutes, centrifuged at 15,000 rpm for 15 minutes at 4° C., and cell lysate of the supernatant was taken. The BCA protein quantification kit was used to detect the protein content of each group, and PIPA lysis buffer was used to adjust the protein amount to make the final volume of 100 μL. Samples were identified by western-blot. 2. Detection of compound inhibition of RIPK1 (S161E) cell death: S161E MEFs were digested and then diluted to $6.25\times10^4$/ml, and the cells were seeded into 384-well plates, 40 μl per well. The plate was placed in a cell incubator (37° C., 5% $CO_2$) for 12 hours. 5z7 (3 μM) and 5 μl of compound (100 μM) diluted in cell culture medium were added to the corresponding wells. After pretreatment at 37° C. for 1 h, 5 μL of TNFα (500 ng/mL) diluted in cell culture medium was added to each well of the stimulation group. 5 μL of culture medium was added to the control group. The plate was placed in the cell incubator (37° C., 5% $CO_2$) for 5 h, 10 h, and 20 h, respectively, then 15 μl of Cell Titer-Glo solution was added to each well. The cells were incubated at room temperature for 30 min, and the luminescence value was detected to measure the level of intracellular ATP. The unstimulated DMSO control well was taken as 100% cell viability. At least three duplicate wells were set for each compound at each time point.

Figure 6:
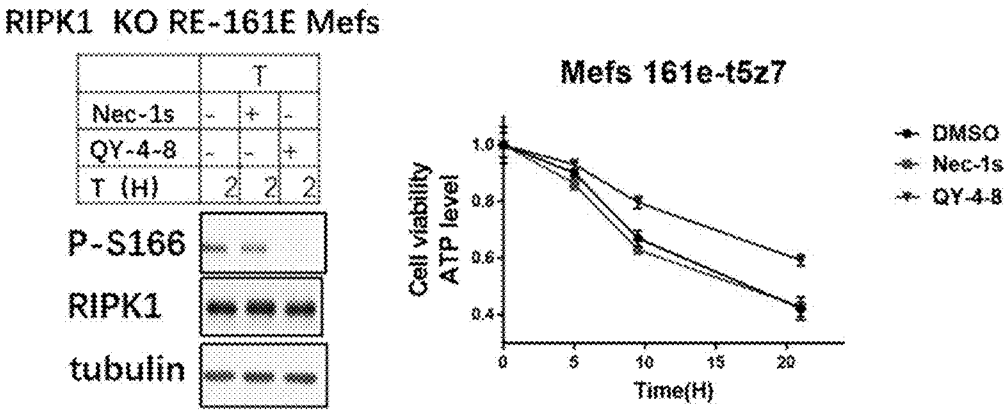
FIG. 6 shows the test result of the effect of serine mutation at position 161 of compound RIPK1 to glutamic acid on the compound in Example 7.

The results are shown in FIG. 6. The experimental results show that the compound QY-4-8 can still inhibit the programmed cells necrosis after the mutation of serine at position 161 of RIPK1 to glutamic acid.

All documents mentioned herein are incorporated by reference in this application as if each document were individually incorporated by reference. In addition, it should be understood that after reading the above teaching content of the present invention, those skilled in the art can make various changes or modifications to the present invention, and these equivalent forms also fall within the scope defined by the appended claims of the present application.

The invention claimed is:

1. A compound represented by the following Formula (I-c), or pharmaceutically acceptable salts thereof, I-c

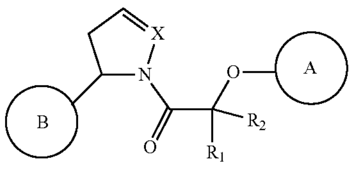

wherein:

dashed line is a chemical bond or none;

X is selected from the group consisting of $CR_2$, NR, O, S, CR, and N;

R is selected from the group consisting of H, D, and C1-C4 alkyl;

$R_1$ and $R_2$ are each independently selected from the group consisting of H and C1-C4 alkyl; or $R_1$ and $R_2$ together form a structure of substituted or unsubstituted $-(CH_2)_n-$; wherein, n is 1, 2, 3, or 4;

ring A is selected from the group consisting of substituted or unsubstituted C6-C10 aryl, and substituted or unsubstituted 5-12 membered heteroaryl;

ring B is selected from the group consisting of substituted or unsubstituted C6-C10 aryl, and substituted or unsubstituted 5-12 membered heteroaryl, wherein the substituted means that at least one hydrogen atom in a group is substituted by one or more substituents selected from the group consisting of halogen, deuterium, C1-C6 alkoxy, halogenated C1-C6 alkoxy, methyl sulfonyl, $-S(=O)_2NH_2$, oxo(=O), —CN, hydroxyl, $-NH_2$, carboxyl, C2-C6 amido (—C(—O)—$N(Rc)_2$ or—NH—C(—O)(Rc), wherein Rc is H or C1-C5 alkyl), C1-C6 alkyl-(C2-C6 amido), and substituted or unsubstituted groups selected from the group consisting of C1-C6 alkyl, C3-C8 cycloalkyl, C1-C6 amino, C6-C10 aryl, 5-10 membered heteroaryl having 1-3 heteroatoms selected from N, S and O, 5-12 membered heterocyclyl having 1-3 heteroatoms selected from N, S and O, $-(CH_2)-$C6-C10 aryl, and $-(CH_2)$-(5-10 membered heteroaryl having 1-3 heteroatoms selected from N, S and O), and the substituents are selected from the group consisting of halogen, C1-C6 alkyl, C1-C6 alkoxy, oxo, —CN, —$NH_2$, —OH, C6-C10 aryl, C1-C6 amino, C2-C6 amido, and 5-10 membered heteroaryl having 1-3 heteroatoms selected from N, S and O.

2. The compound according to claim 1, wherein the compound of Formula (I-c) has a structure selected from the group consisting of I-a and I-b:

I-a

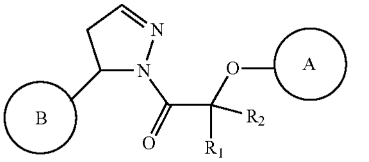

-continued

I-b

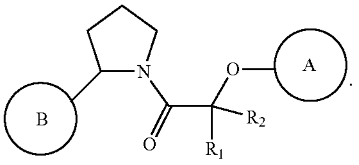

3. The compound according to claim 1, wherein the ring A is selected from the group consisting of substituted or unsubstituted phenyl and substituted or unsubstituted 5-7 membered heteroaryl; and/or ring B is selected from the group consisting of substituted or unsubstituted phenyl and substituted or unsubstituted 5-7 membered heteroaryl.

4. The compound according to claim 1, wherein the compound is selected from the following table:

| Compound number | Chemical structure | Compound number | Chemical structure |
|---|---|---|---|
| QY-1-98 | 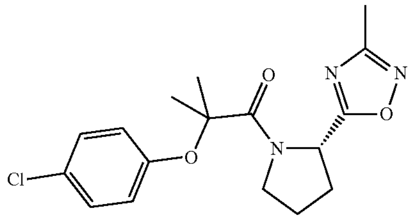 [SMILES: Cc1noc([C@@H]2CCCN2C(=O)C(C)(C)Oc2ccc(Cl)cc2)n1] | QY-4-6 | 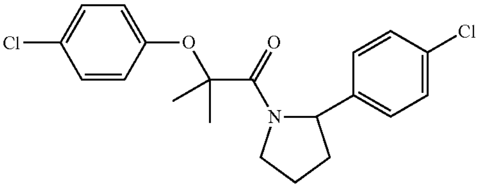 [SMILES: CC(C)(Oc1ccc(Cl)cc1)C(=O)N1CCCC1c1ccc(Cl)cc1] |
| QY-2-25 | 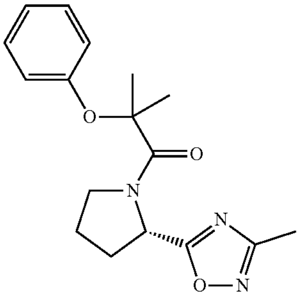 [SMILES: Cc1noc([C@@H]2CCCN2C(=O)C(C)(C)Oc2ccccc2)n1] | QY-4-7 | 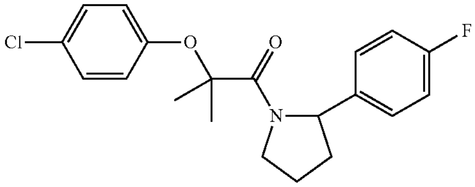 [SMILES: CC(C)(Oc1ccc(Cl)cc1)C(=O)N1CCCC1c1ccc(F)cc1] |
| QY-2-26 | 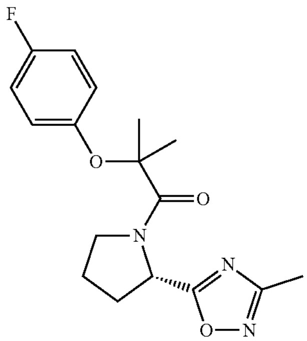 [SMILES: Cc1noc([C@@H]2CCCN2C(=O)C(C)(C)Oc2ccc(F)cc2)n1] | QY-4-8 | 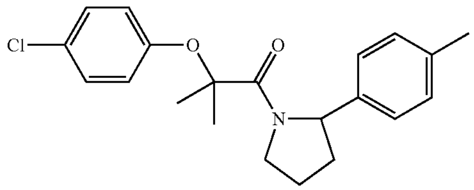 [SMILES: Cc1ccc(C2CCCN2C(=O)C(C)(C)Oc2ccc(Cl)cc2)cc1] |

-continued
| Compound number | Chemical structure | Compound number | Chemical structure |
| --- | --- | --- | --- |
| QY-2-27 | 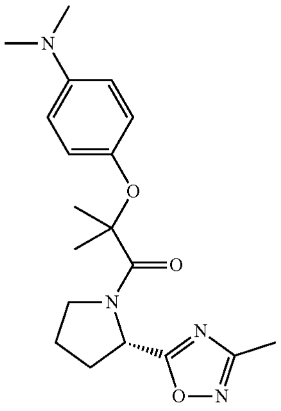 | QY-4-11 | 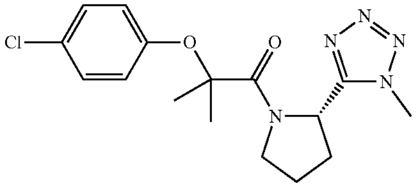 [SMILES: Cn1nnnc1[C@@H]1CCCN1C(=O)C(C)(C)Oc1ccc(Cl)cc1] |
| QY-2-34 | 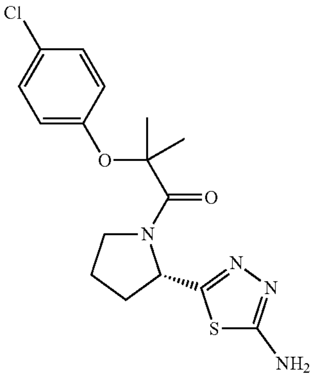 [SMILES: CC(C)(Oc1ccc(Cl)cc1)C(=O)N1CCC[C@H]1c1nnc(N)s1] | QY-4-12 | 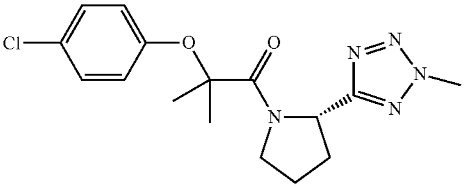 [SMILES: Cn1nnc([C@@H]2CCCN2C(=O)C(C)(C)Oc2ccc(Cl)cc2)n1] |
| QY-2-38 | 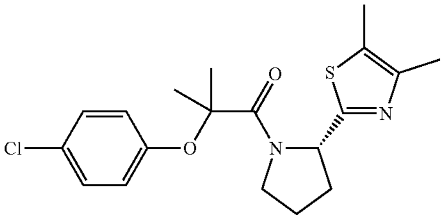 [SMILES: Cc1nc([C@@H]2CCCN2C(=O)C(C)(C)Oc2ccc(Cl)cc2)sc1C] | QY-4-14 | 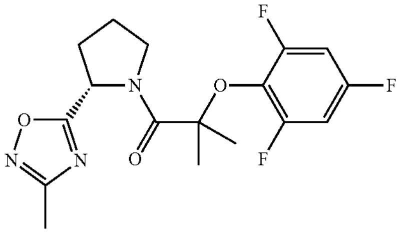 [SMILES: Cc1noc([C@@H]2CCCN2C(=O)C(C)(C)Oc2c(F)cc(F)cc2F)n1] |
| QY-2-39 | 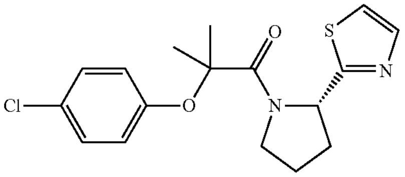 [SMILES: CC(C)(Oc1ccc(Cl)cc1)C(=O)N1CCC[C@H]1c1nccs1] | QY-4-27 | 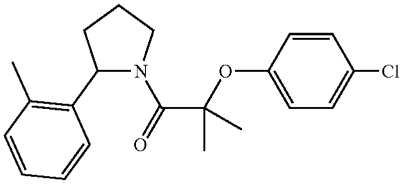 [SMILES: Cc1ccccc1C1CCCN1C(=O)C(C)(C)Oc1ccc(Cl)cc1] |
| QY-2-52 | 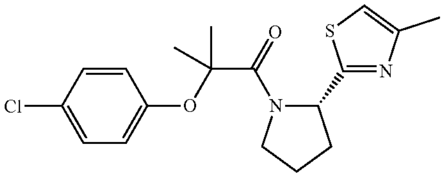 [SMILES: Cc1csc([C@@H]2CCCN2C(=O)C(C)(C)Oc2ccc(Cl)cc2)n1] | QY-4-32 | 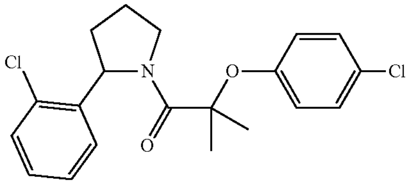 [SMILES: CC(C)(Oc1ccc(Cl)cc1)C(=O)N1CCCC1c1ccccc1Cl] |

-continued
| Compound number | Chemical structure | Compound number | Chemical structure |
|---|---|---|---|
| QY-2-53 | 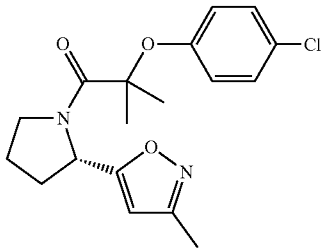 [SMILES: Cc1cc([C@@H]2CCCN2C(=O)C(C)(C)Oc2ccc(Cl)cc2)on1] | QY-4-35 | 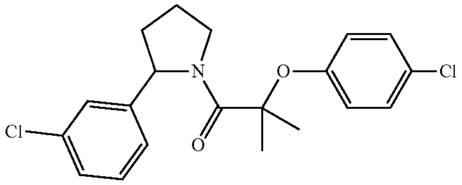 [SMILES: CC(C)(Oc1ccc(Cl)cc1)C(=O)N1CCCC1c1cccc(Cl)c1] |
| QY-2-54 | 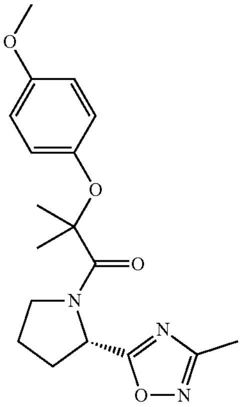 [SMILES: COc1ccc(OC(C)(C)C(=O)N2CCC[C@H]2c2nc(C)no2)cc1] | QY-4-39 | 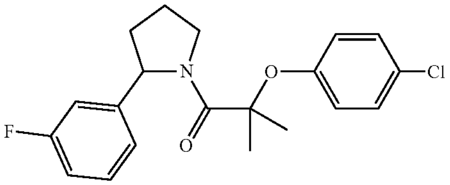 [SMILES: CC(C)(Oc1ccc(Cl)cc1)C(=O)N1CCCC1c1cccc(F)c1] |
| QY-2-55 | 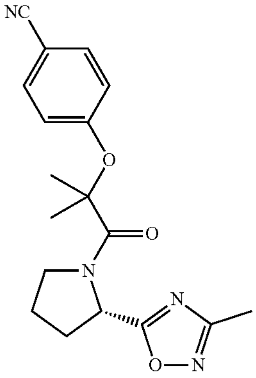 [SMILES: Cc1noc([C@@H]2CCCN2C(=O)C(C)(C)Oc2ccc(C#N)cc2)n1] | QY-4-66 | 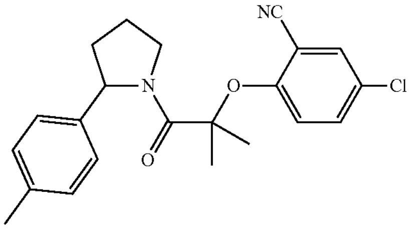 [SMILES: Cc1ccc(C2CCCN2C(=O)C(C)(C)Oc2ccc(Cl)cc2C#N)cc1] |
| QY-2-56 | 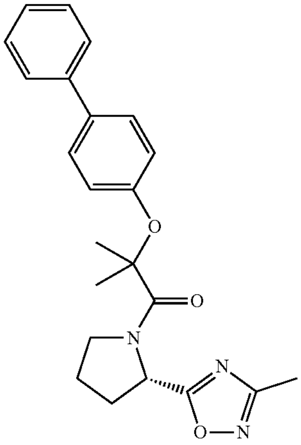 [SMILES: Cc1noc([C@@H]2CCCN2C(=O)C(C)(C)Oc2ccc(-c3ccccc3)cc2)n1] | QY-4-67 | 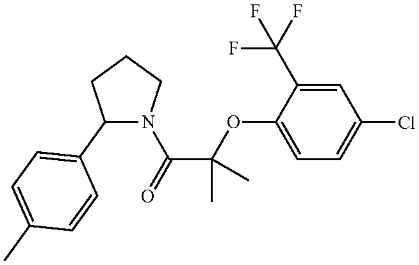 [SMILES: Cc1ccc(C2CCCN2C(=O)C(C)(C)Oc2ccc(Cl)cc2C(F)(F)F)cc1] |

-continued
| Compound number | Chemical structure | Compound number | Chemical structure |
|---|---|---|---|
| QY-2-75 | 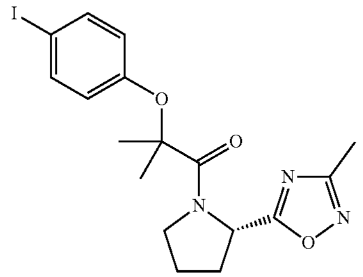 [SMILES: Cc1noc([C@@H]2CCCN2C(=O)C(C)(C)Oc2ccc(I)cc2)n1] | QY-4-69 | 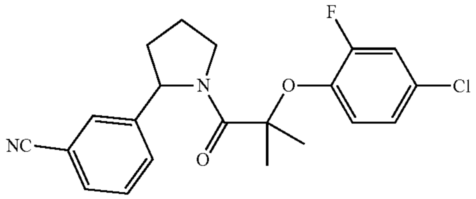 [SMILES: CC(C)(Oc1ccc(Cl)cc1F)C(=O)N1CCCC1c1cccc(C#N)c1] |
| QY-2-76 | 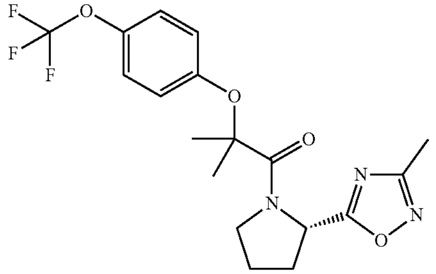 [SMILES: Cc1noc([C@@H]2CCCN2C(=O)C(C)(C)Oc2ccc(OC(F)(F)F)cc2)n1] | QY-4-70 | 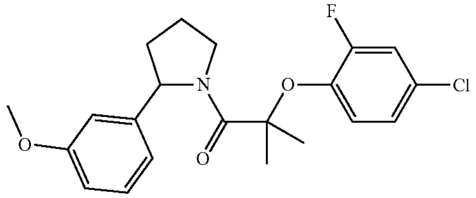 |
| QY-2-77 | 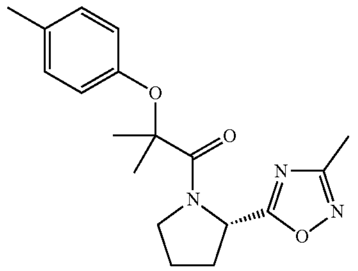 | QY-4-75 | 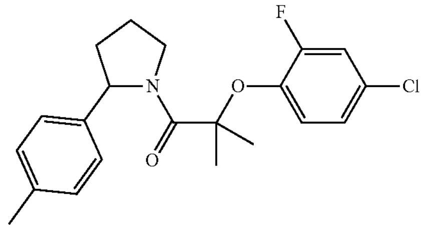 [SMILES: Cc1ccc(C2CCCN2C(=O)C(C)(C)Oc2ccc(Cl)cc2F)cc1] |
| QY-2-78 | 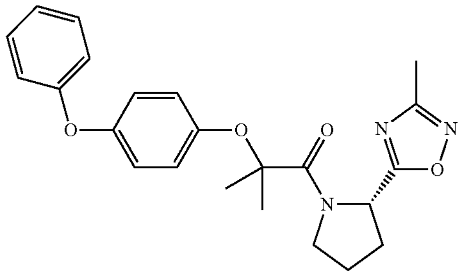 [SMILES: Cc1noc([C@@H]2CCCN2C(=O)C(C)(C)Oc2ccc(Oc3ccccc3)cc2)n1] | QY-4-78 | 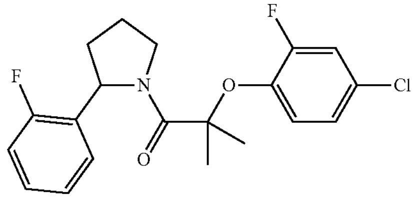 [SMILES: CC(C)(Oc1ccc(Cl)cc1F)C(=O)N1CCCC1c1ccccc1F] |
| QY-2-79 | 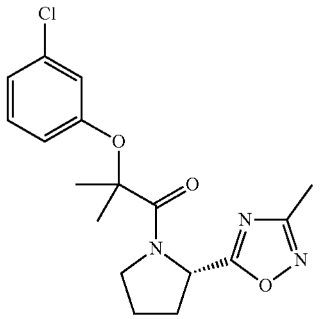 [SMILES: Cc1noc([C@@H]2CCCN2C(=O)C(C)(C)Oc2cccc(Cl)c2)n1] | QY-4-87 | 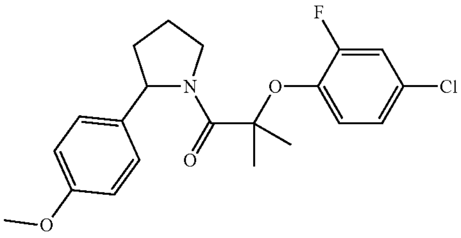 [SMILES: COc1ccc(C2CCCN2C(=O)C(C)(C)Oc2ccc(Cl)cc2F)cc1] |

-continued
| Compound number | Chemical structure | Compound number | Chemical structure |
|---|---|---|---|
| QY-2-100 | 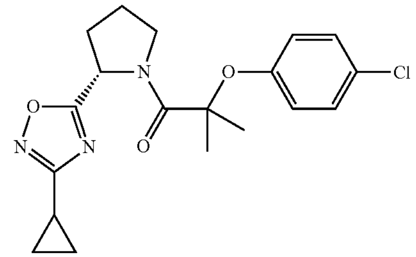 [SMILES: CC(C)(Oc1ccc(Cl)cc1)C(=O)N1CCC[C@H]1c1nc(C2CC2)no1] | QY-4-88 | 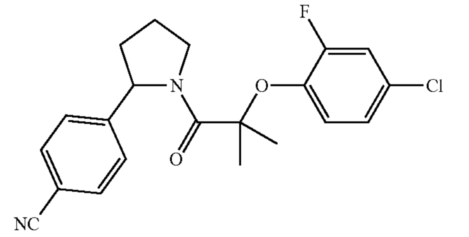 [SMILES: CC(C)(Oc1ccc(Cl)cc1F)C(=O)N1CCCC1c1ccc(C#N)cc1] |
| QY-2-103 | 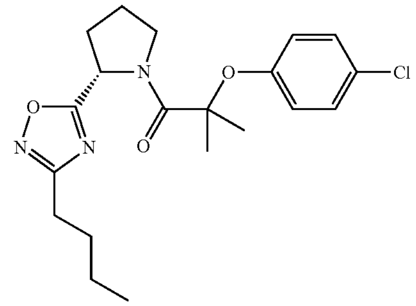 [SMILES: CCCCc1noc([C@@H]2CCCN2C(=O)C(C)(C)Oc2ccc(Cl)cc2)n1] | QY-4-96 | 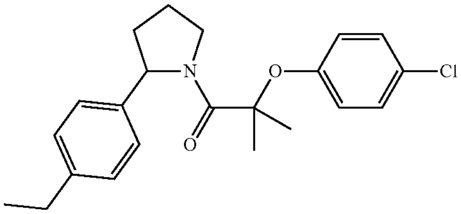 [SMILES: CCc1ccc(C2CCCN2C(=O)C(C)(C)Oc2ccc(Cl)cc2)cc1] |
| QY-2-104 | 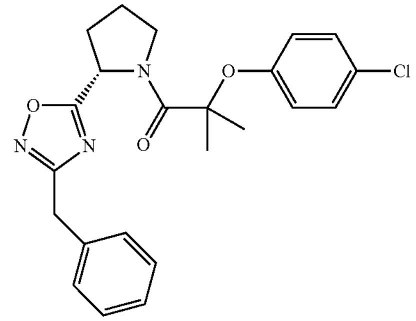 [SMILES: CC(C)(Oc1ccc(Cl)cc1)C(=O)N1CCC[C@H]1c1nc(Cc2ccccc2)no1] | QY-4-99 | 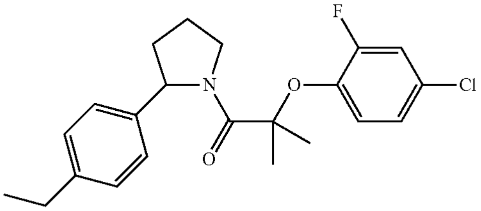 [SMILES: CCc1ccc(C2CCCN2C(=O)C(C)(C)Oc2ccc(Cl)cc2F)cc1] |
| QY-3-4 | 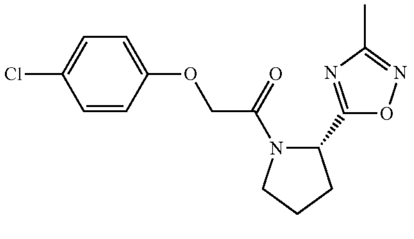 [SMILES: Cc1noc([C@@H]2CCCN2C(=O)COc2ccc(Cl)cc2)n1] | QY-5-1 | 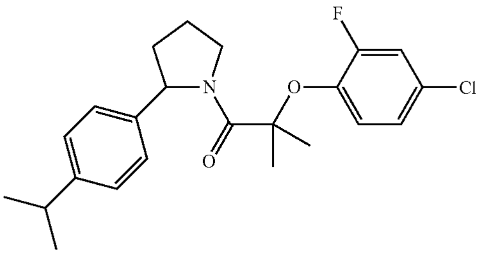 [SMILES: CC(C)c1ccc(C2CCCN2C(=O)C(C)(C)Oc2ccc(Cl)cc2F)cc1] |
| QY-3-11 | 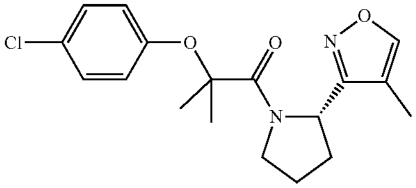 [SMILES: Cc1conc1[C@@H]1CCCN1C(=O)C(C)(C)Oc1ccc(Cl)cc1] | QY-5-4 | 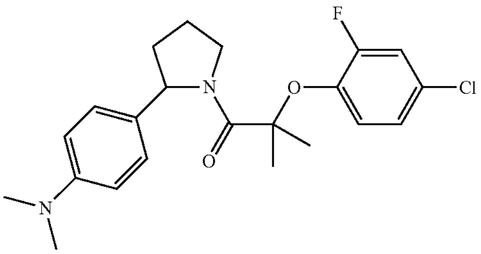 [SMILES: CN(C)c1ccc(C2CCCN2C(=O)C(C)(C)Oc2ccc(Cl)cc2F)cc1] |

-continued
| Compound number | Chemical structure | Compound number | Chemical structure |
|---|---|---|---|
| QY-3-17 | 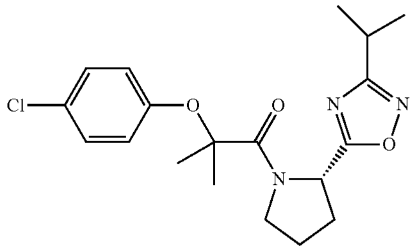 [SMILES: CC(C)c1noc([C@@H]2CCCN2C(=O)C(C)(C)Oc2ccc(Cl)cc2)n1] | QY-5-21 | 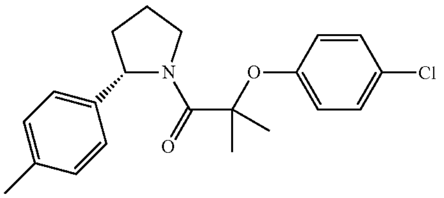 |
| QY-3-26 | 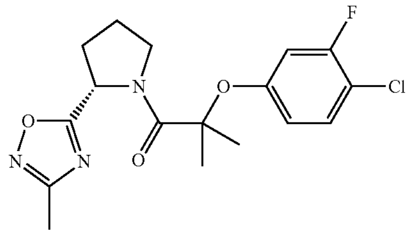 [SMILES: Cc1noc([C@@H]2CCCN2C(=O)C(C)(C)Oc2ccc(Cl)c(F)c2)n1] | QY-5-22 | 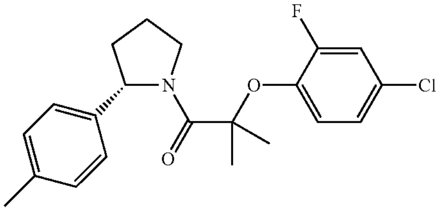 [SMILES: Cc1ccc([C@@H]2CCCN2C(=O)C(C)(C)Oc2ccc(Cl)cc2F)cc1] |
| QY-3-27 | 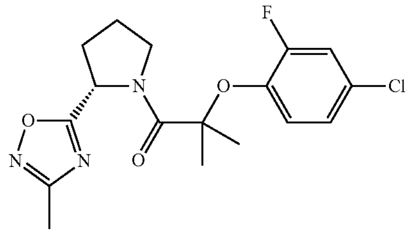 [SMILES: Cc1noc([C@@H]2CCCN2C(=O)C(C)(C)Oc2ccc(Cl)cc2F)n1] | QY-5-79 | 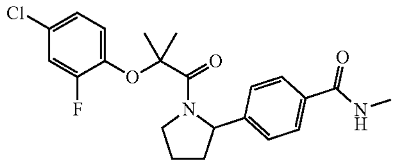 [SMILES: CNC(=O)c1ccc(C2CCCN2C(=O)C(C)(C)Oc2ccc(Cl)cc2F)cc1] |
| QY-3-28 | 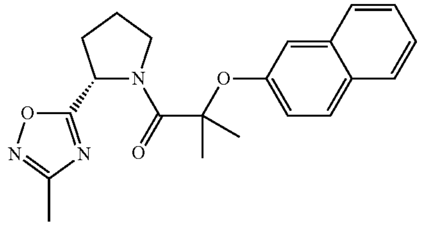 [SMILES: Cc1noc([C@@H]2CCCN2C(=O)C(C)(C)Oc2ccc3ccccc3c2)n1] | QY-5-83 | 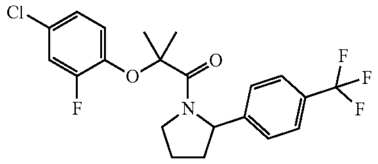 [SMILES: CC(C)(Oc1ccc(Cl)cc1F)C(=O)N1CCCC1c1ccc(C(F)(F)F)cc1] |
| QY-3-29 | 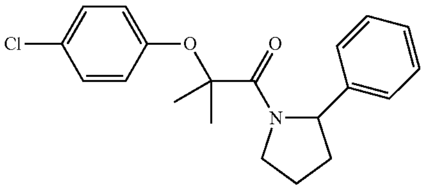 [SMILES: CC(C)(Oc1ccc(Cl)cc1)C(=O)N1CCCC1c1ccccc1] | QY-5-85 | 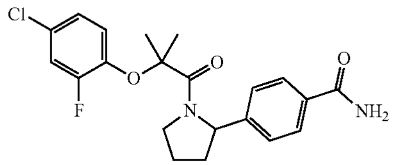 [SMILES: CC(C)(Oc1ccc(Cl)cc1F)C(=O)N1CCCC1c1ccc(C(N)=O)cc1] |
| QY-3-35 | 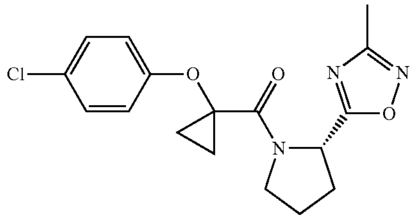 [SMILES: Cc1noc([C@@H]2CCCN2C(=O)C2(Oc3ccc(Cl)cc3)CC2)n1] | QY-6-47 | 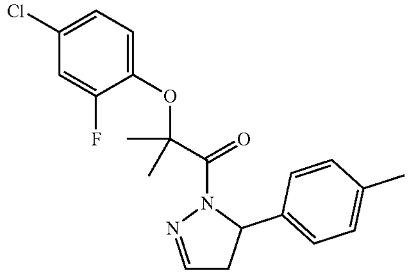 [SMILES: Cc1ccc(C2CC=NN2C(=O)C(C)(C)Oc2ccc(Cl)cc2F)cc1] |

-continued
| Compound number | Chemical structure | Compound number | Chemical structure |
|---|---|---|---|
| QY-3-36 | 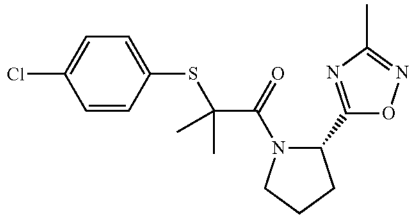 [SMILES: Cc1noc([C@@H]2CCCN2C(=O)C(C)(C)Sc2ccc(Cl)cc2)n1] | QY-6-60 | 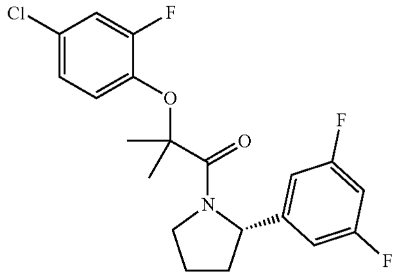 [SMILES: CC(C)(Oc1ccc(Cl)cc1F)C(=O)N1CCC[C@H]1c1cc(F)cc(F)c1] |
| QY-3-39 | 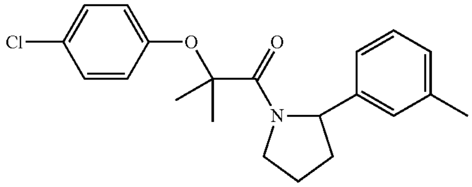 [SMILES: Cc1cccc(C2CCCN2C(=O)C(C)(C)Oc2ccc(Cl)cc2)c1] | QY-6-61 | 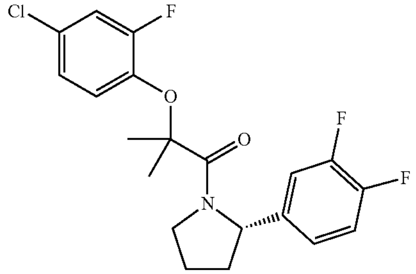 [SMILES: CC(C)(Oc1ccc(Cl)cc1F)C(=O)N1CCC[C@H]1c1ccc(F)c(F)c1] |
| QY-3-46 | 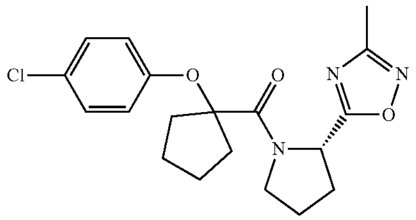 [SMILES: Cc1noc([C@@H]2CCCN2C(=O)C2(Oc3ccc(Cl)cc3)CCCC2)n1] | QY-6-62 | 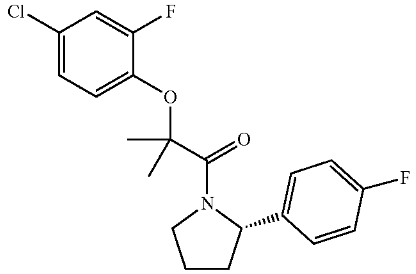 [SMILES: CC(C)(Oc1ccc(Cl)cc1F)C(=O)N1CCC[C@H]1c1ccc(F)cc1] |
| QY-3-51 | 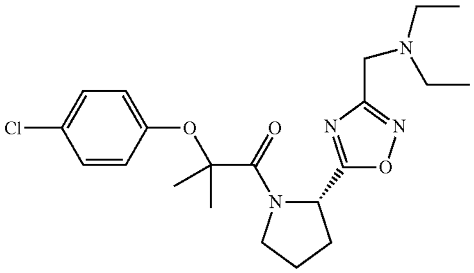 [SMILES: CCN(CC)Cc1noc([C@@H]2CCCN2C(=O)C(C)(C)Oc2ccc(Cl)cc2)n1] | QY-6-63 | 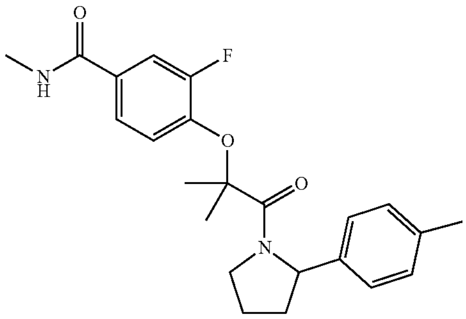 |
| QY-3-65 | 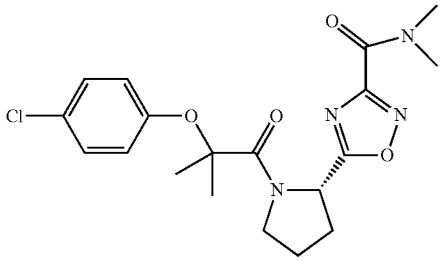 [SMILES: CN(C)C(=O)c1noc([C@@H]2CCCN2C(=O)C(C)(C)Oc2ccc(Cl)cc2)n1] | QY-6-83 | 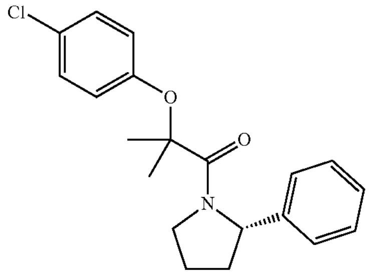 [SMILES: CC(C)(Oc1ccc(Cl)cc1)C(=O)N1CCC[C@H]1c1ccccc1] |

-continued
| Compound number | Chemical structure | Compound number | Chemical structure |
|---|---|---|---|
| QY-3-81 | 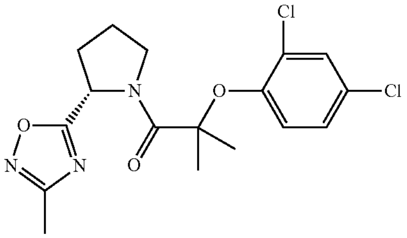 [SMILES: Cc1noc([C@@H]2CCCN2C(=O)C(C)(C)Oc2ccc(Cl)cc2Cl)n1] | QY-6-84 | 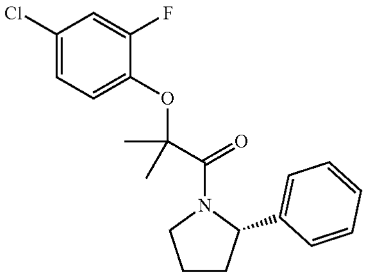 [SMILES: CC(C)(Oc1ccc(Cl)cc1F)C(=O)N1CCC[C@H]1c1ccccc1] |
| QY-3-86 | 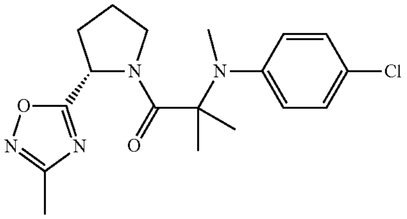 [SMILES: Cc1noc([C@@H]2CCCN2C(=O)C(C)(C)N(C)c2ccc(Cl)cc2)n1] | QY-7-7 | 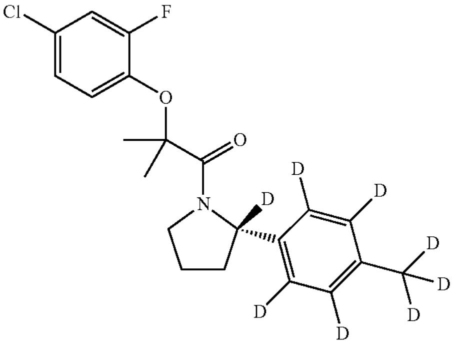 [SMILES: [2H]c1c([2H])c([C@]2([2H])CCCN2C(=O)C(C)(C)Oc2ccc(Cl)cc2F)c([2H])c([2H])c1C([2H])([2H])[2H]] |
| QY-3-94 | 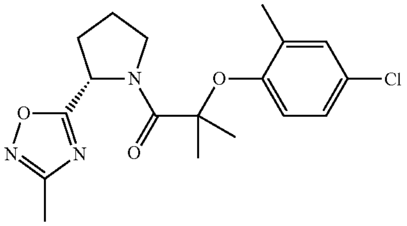 [SMILES: Cc1noc([C@@H]2CCCN2C(=O)C(C)(C)Oc2ccc(Cl)cc2C)n1] | QY-7-50 | 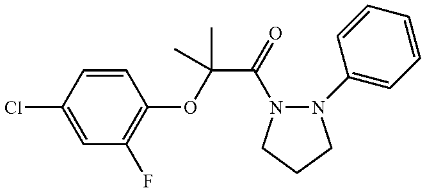 [SMILES: CC(C)(Oc1ccc(Cl)cc1F)C(=O)N1CCCN1c1ccccc1] |
| QY-3-95 | 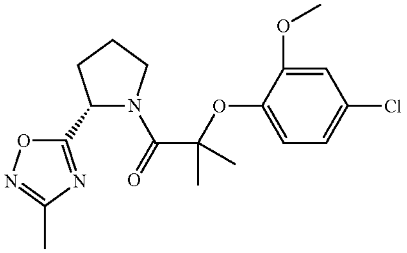 [SMILES: COc1cc(Cl)ccc1OC(C)(C)C(=O)N1CCC[C@H]1c1nc(C)no1] | QY-7-60 | 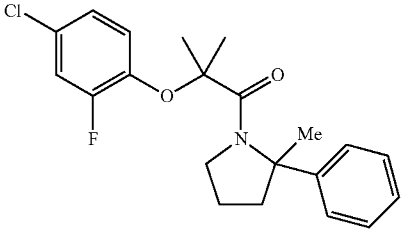 [SMILES: CC(C)(Oc1ccc(Cl)cc1F)C(=O)N1CCCC1(C)c1ccccc1] |
| QY-3-96 | 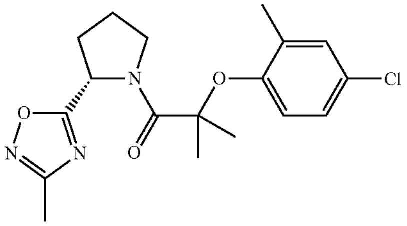 [SMILES: Cc1noc([C@@H]2CCCN2C(=O)C(C)(C)Oc2ccc(Cl)cc2C)n1] | QY-7-62 | 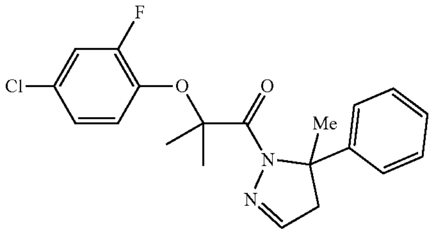 [SMILES: CC(C)(Oc1ccc(Cl)cc1F)C(=O)N1N=CCC1(C)c1ccccc1] |

-continued
| Compound number | Chemical structure | Compound number | Chemical structure |
|---|---|---|---|
| QY-3-99 | 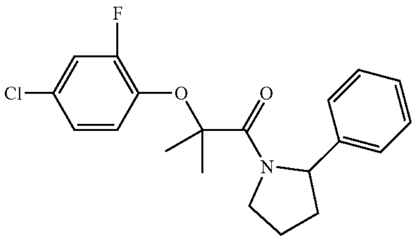 [SMILES: CC(C)(Oc1ccc(Cl)cc1F)C(=O)N1CCCC1c1ccccc1] | XHJ-3-22 | 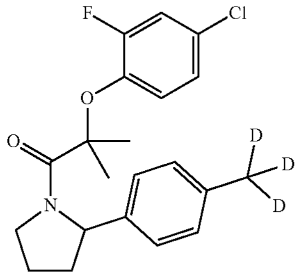 [SMILES: [2H]C([2H])([2H])c1ccc(C2CCCN2C(=O)C(C)(C)Oc2ccc(Cl)cc2F)cc1] |
| QY4-1 | 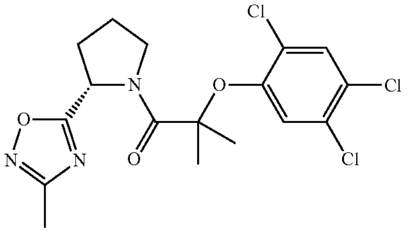 [SMILES: Cc1noc([C@@H]2CCCN2C(=O)C(C)(C)Oc2cc(Cl)c(Cl)cc2Cl)n1] | ZSQ-13-56 | 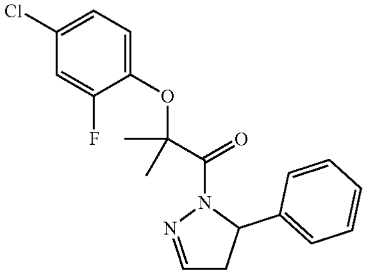 [SMILES: CC(C)(Oc1ccc(Cl)cc1F)C(=O)N1N=CCC1c1ccccc1] |
| QY4-2 | 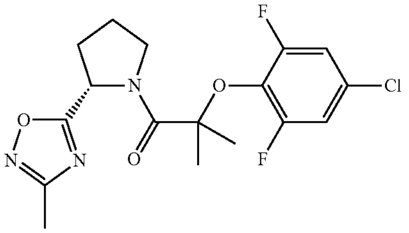 [SMILES: Cc1noc([C@@H]2CCCN2C(=O)C(C)(C)Oc2c(F)cc(Cl)cc2F)n1] | ZSQ-13-57 | 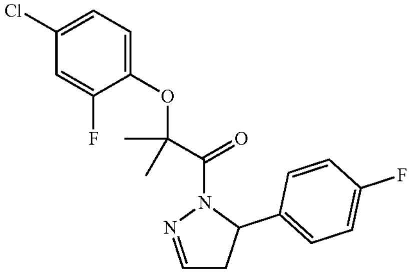 [SMILES: CC(C)(Oc1ccc(Cl)cc1F)C(=O)N1N=CCC1c1ccc(F)cc1] |
| QY-7-101 | 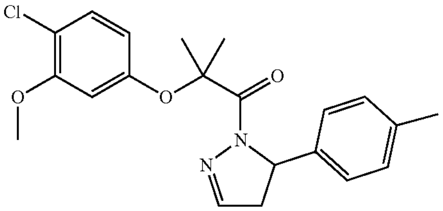 [SMILES: COc1cc(OC(C)(C)C(=O)N2N=CCC2c2ccc(C)cc2)ccc1Cl] | QY-8-101 | 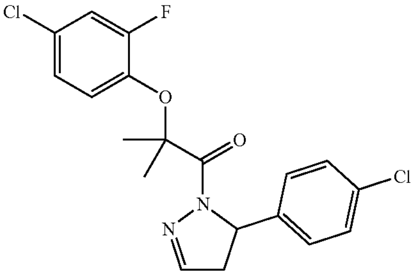 [SMILES: CC(C)(Oc1ccc(Cl)cc1F)C(=O)N1N=CCC1c1ccc(Cl)cc1] |
| QY-9-8 | 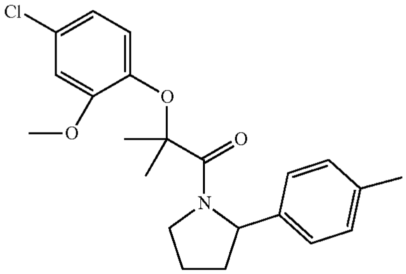 [SMILES: COc1cc(Cl)ccc1OC(C)(C)C(=O)N1CCCC1c1ccc(C)cc1] | QY-9-32 | 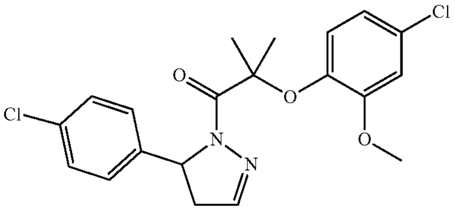 [SMILES: COc1cc(Cl)ccc1OC(C)(C)C(=O)N1N=CCC1c1ccc(Cl)cc1] |

-continued
| Compound number | Chemical structure | Compound number | Chemical structure |
|---|---|---|---|
| QY-9-43 | 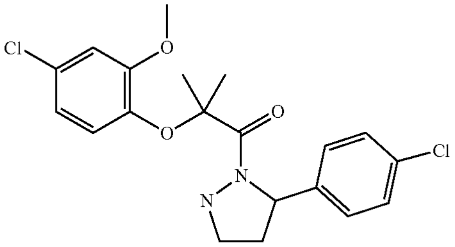 [SMILES: COc1cc(Cl)ccc1OC(C)(C)C(=O)N1NCCC1c1ccc(Cl)cc1] | QY-10-1 | 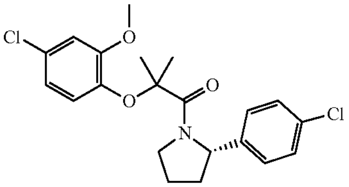 [SMILES: COc1cc(Cl)ccc1OC(C)(C)C(=O)N1CCC[C@H]1c1ccc(Cl)cc1] |
| QY-10-92 | 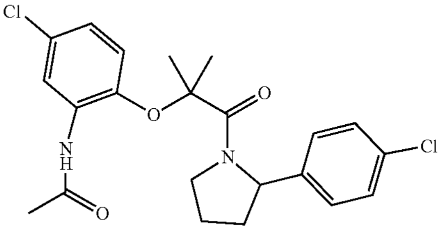 [SMILES: CC(=O)Nc1cc(Cl)ccc1OC(C)(C)C(=O)N1CCCC1c1ccc(Cl)cc1] | QY-10-96 | 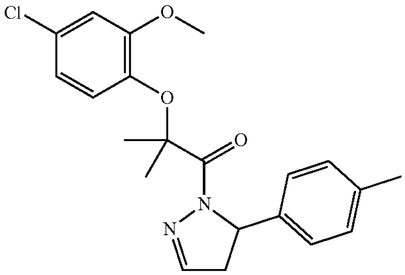 [SMILES: COc1cc(Cl)ccc1OC(C)(C)C(=O)N1N=CCC1c1ccc(C)cc1] |
| QY-10-104 | 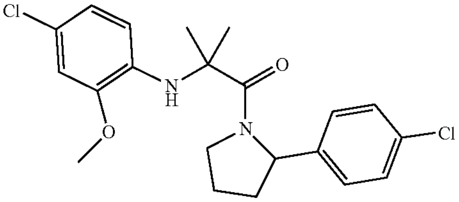 [SMILES: COc1cc(Cl)ccc1NC(C)(C)C(=O)N1CCCC1c1ccc(Cl)cc1] | QY-11-1 | 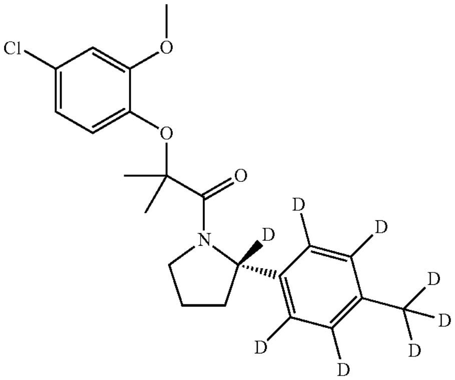 [SMILES: [2H]c1c([2H])c([C@]2([2H])CCCN2C(=O)C(C)(C)Oc2ccc(Cl)cc2OC)c([2H])c([2H])c1C([2H])([2H])[2H]] |
| QY-11-9A | 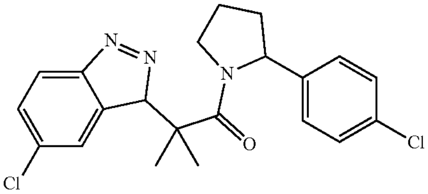 [SMILES: CC(C)(C(=O)N1CCCC1c1ccc(Cl)cc1)C1N=Nc2ccc(Cl)cc21] | QY-11-9B | 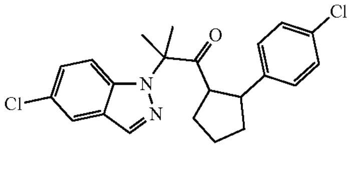 [SMILES: CC(C)(C(=O)C1CCCC1c1ccc(Cl)cc1)n1ncc2cc(Cl)ccc21] |
| QY-11-11A | 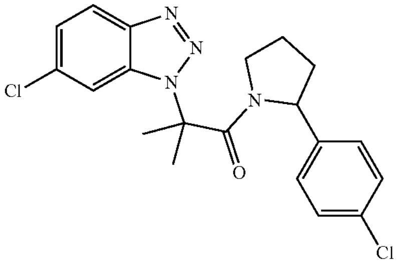 [SMILES: CC(C)(C(=O)N1CCCC1c1ccc(Cl)cc1)n1nnc2ccc(Cl)cc21] | QY-11-11B | 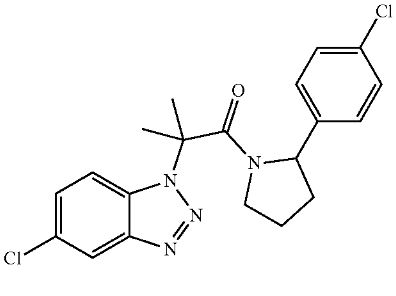 |

-continued
| Compound number | Chemical structure | Compound number | Chemical structure |
|---|---|---|---|
| QY-11-15B | 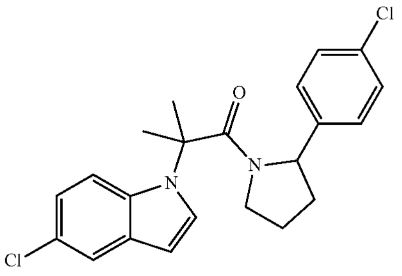 [SMILES: CC(C)(C(=O)N1CCCC1c1ccc(Cl)cc1)n1ccc2cc(Cl)ccc21] | QY-11-16A | 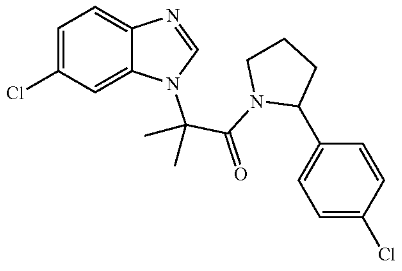 [SMILES: CC(C)(C(=O)N1CCCC1c1ccc(Cl)cc1)n1cnc2ccc(Cl)cc21] |
| QY-11-16B | 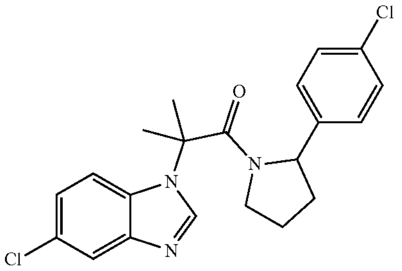 | QY-11-36 | 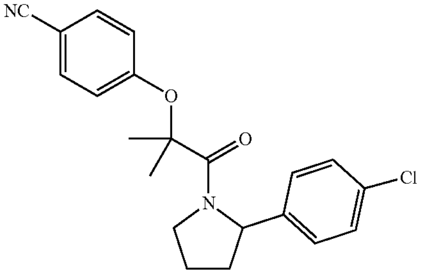 [SMILES: CC(C)(Oc1ccc(C#N)cc1)C(=O)N1CCCC1c1ccc(Cl)cc1] |
| QY-11-44 | 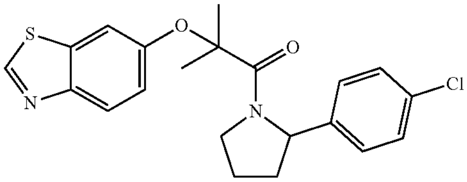 [SMILES: CC(C)(Oc1ccc2ncsc2c1)C(=O)N1CCCC1c1ccc(Cl)cc1] | QY-11-45 | 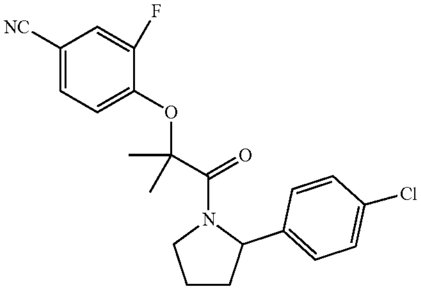 [SMILES: CC(C)(Oc1ccc(C#N)cc1F)C(=O)N1CCCC1c1ccc(Cl)cc1] |
| QY-12-11 | 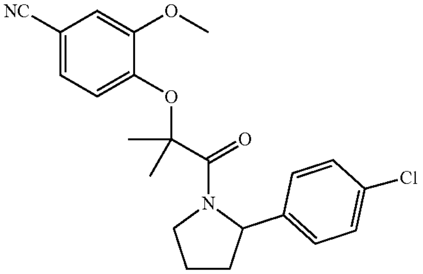 [SMILES: COc1cc(C#N)ccc1OC(C)(C)C(=O)N1CCCC1c1ccc(Cl)cc1] | QY-12-14 | 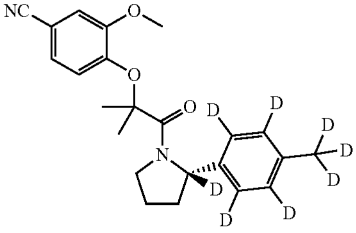 [SMILES: [2H]c1c([2H])c([C@]2([2H])CCCN2C(=O)C(C)(C)Oc2ccc(C#N)cc2OC)c([2H])c([2H])c1C([2H])([2H])[2H]] |
| QY-12-32 | 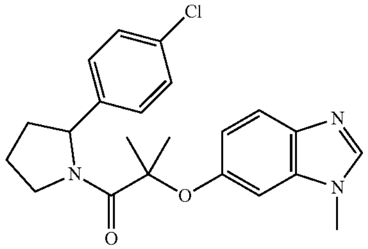 [SMILES: Cn1cnc2ccc(OC(C)(C)C(=O)N3CCCC3c3ccc(Cl)cc3)cc21] | QY-13-42 | 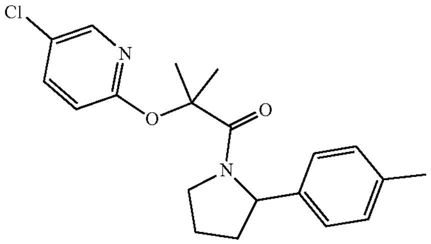 [SMILES: Cc1ccc(C2CCCN2C(=O)C(C)(C)Oc2ccc(Cl)cn2)cc1] |

-continued
| Compound number | Chemical structure | Compound number | Chemical structure |
|---|---|---|---|
| QY-13-68 | 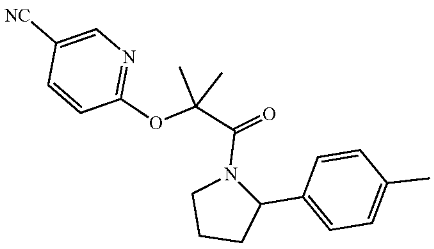 [SMILES: Cc1ccc(C2CCCN2C(=O)C(C)(C)Oc2ccc(C#N)cn2)cc1] | QY-13-70 | 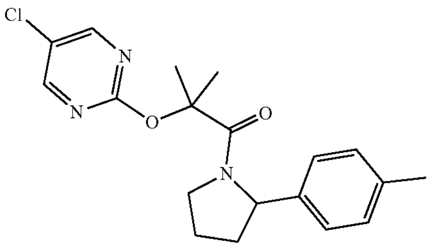 [SMILES: Cc1ccc(C2CCCN2C(=O)C(C)(C)Oc2ncc(Cl)cn2)cc1] |
| QY-13-86 | 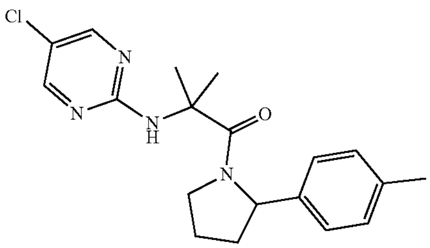 | QY-14-8 | 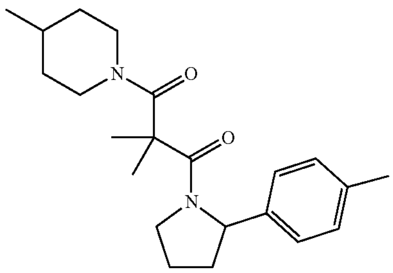 |
| QY-14-9 | 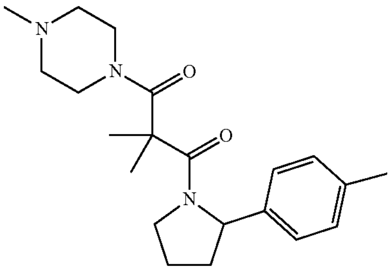 | QY-14-17 | 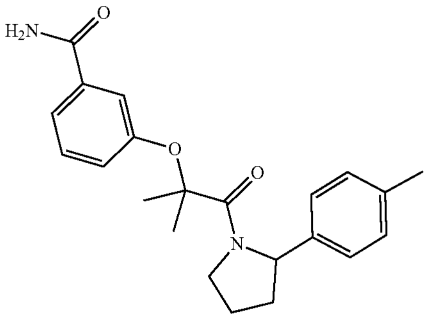 [SMILES: Cc1ccc(C2CCCN2C(=O)C(C)(C)Oc2cccc(C(N)=O)c2)cc1] |
| QY-14-24 | 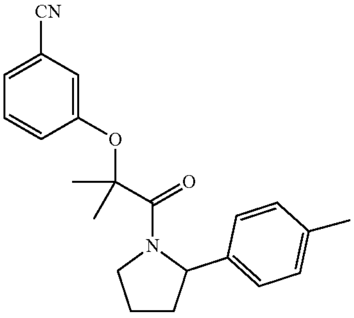 [SMILES: Cc1ccc(C2CCCN2C(=O)C(C)(C)Oc2cccc(C#N)c2)cc1] | QY-14-25 | 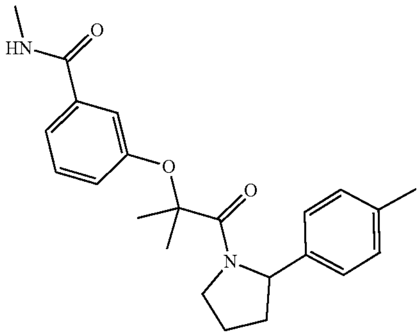 |
| QY-14-27 | 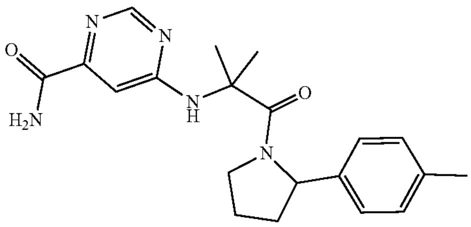 [SMILES: Cc1ccc(C2CCCN2C(=O)C(C)(C)Nc2cc(C(N)=O)ncn2)cc1] | QY-14-29 | 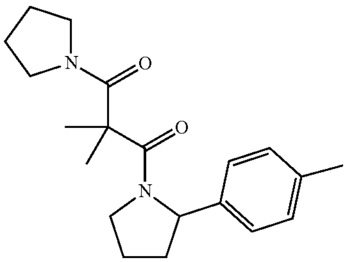 [SMILES: Cc1ccc(C2CCCN2C(=O)C(C)(C)C(=O)N2CCCC2)cc1] |

-continued
| Compound number | Chemical structure | Compound number | Chemical structure |
|---|---|---|---|
| QY-14-30 | 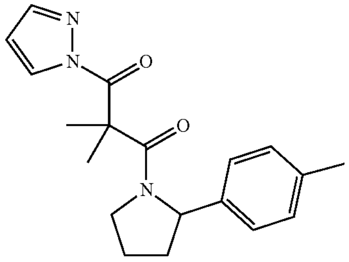 [SMILES: Cc1ccc(C2CCCN2C(=O)C(C)(C)C(=O)n2cccn2)cc1] | QY-14-31 | 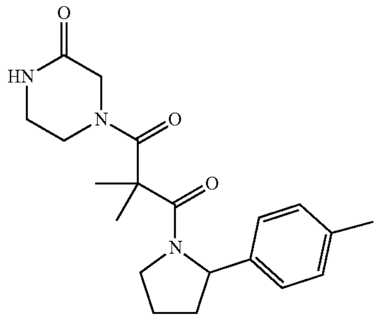 [SMILES: Cc1ccc(C2CCCN2C(=O)C(C)(C)C(=O)N2CCNC(=O)C2)cc1] |
| QY-14-33 | 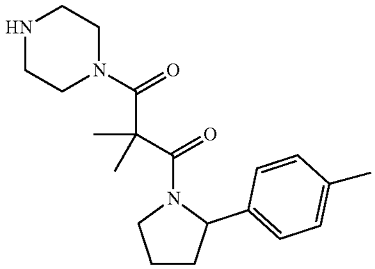 [SMILES: Cc1ccc(C2CCCN2C(=O)C(C)(C)C(=O)N2CCNCC2)cc1] | QY-14-34 | 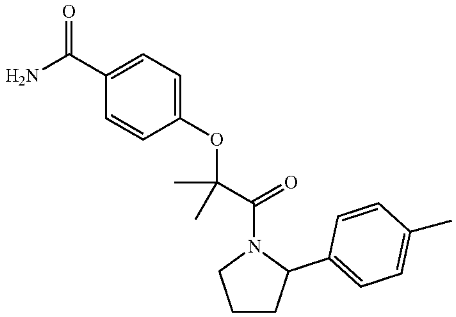 [SMILES: Cc1ccc(C2CCCN2C(=O)C(C)(C)Oc2ccc(C(N)=O)cc2)cc1] |
| QY-14-35 | 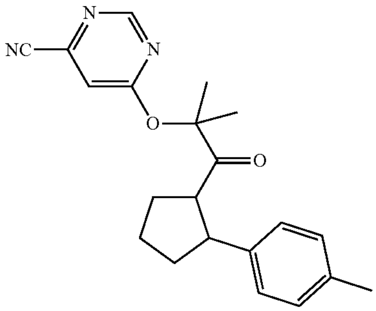 [SMILES: Cc1ccc(C2CCCC2C(=O)C(C)(C)Oc2cc(C#N)ncn2)cc1] | QY-14-40 | 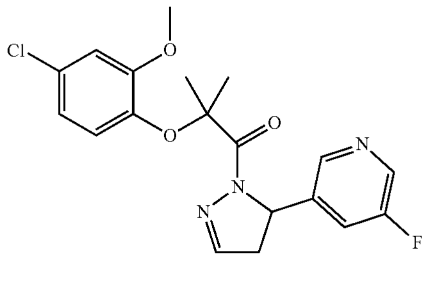 [SMILES: COc1cc(Cl)ccc1OC(C)(C)C(=O)N1N=CCC1c1cncc(F)c1] |
| QY-14-44 | 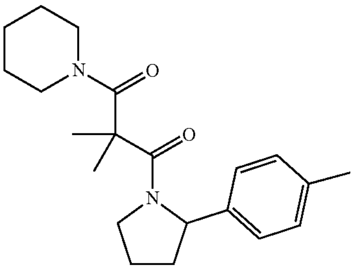 [SMILES: Cc1ccc(C2CCCN2C(=O)C(C)(C)C(=O)N2CCCCC2)cc1] | QY-14-59 | 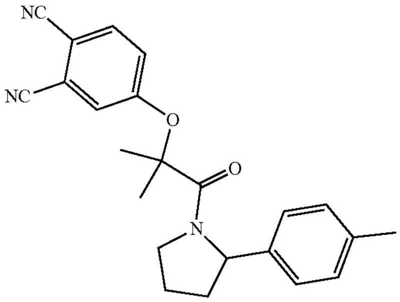 [SMILES: Cc1ccc(C2CCCN2C(=O)C(C)(C)Oc2ccc(C#N)c(C#N)c2)cc1] |

-continued
| Compound number | Chemical structure | Compound number | Chemical structure |
|---|---|---|---|
| QY-14-60 | 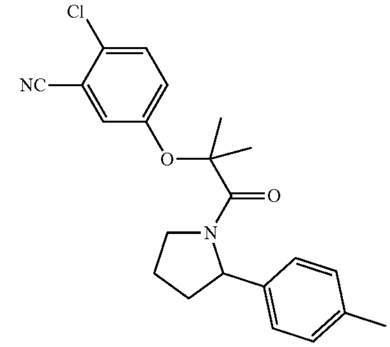 [SMILES: Cc1ccc(C2CCCN2C(=O)C(C)(C)Oc2ccc(Cl)c(C#N)c2)cc1] | QY-14-68 | 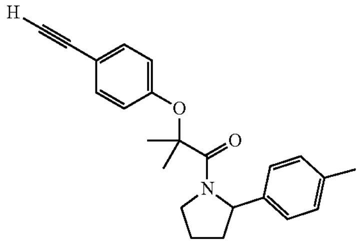 [SMILES: C#Cc1ccc(OC(C)(C)C(=O)N2CCCC2c2ccc(C)cc2)cc1] |
| QY-15-11 | 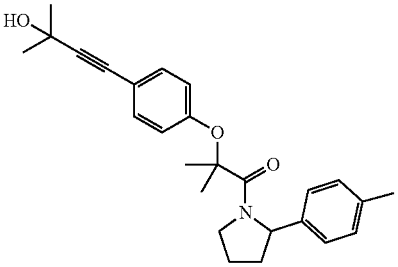 [SMILES: Cc1ccc(C2CCCN2C(=O)C(C)(C)Oc2ccc(C#CC(C)(C)O)cc2)cc1] | QY-15-12 | 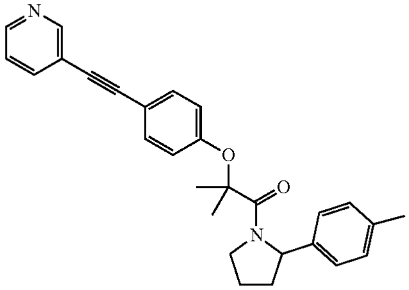 [SMILES: Cc1ccc(C2CCCN2C(=O)C(C)(C)Oc2ccc(C#Cc3cccnc3)cc2)cc1] |
| QY-15-31 | 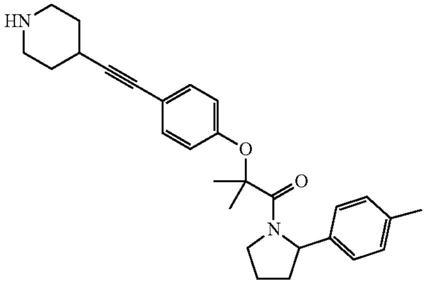 [SMILES: Cc1ccc(C2CCCN2C(=O)C(C)(C)Oc2ccc(C#CC3CCNCC3)cc2)cc1] | QY-16-60 | 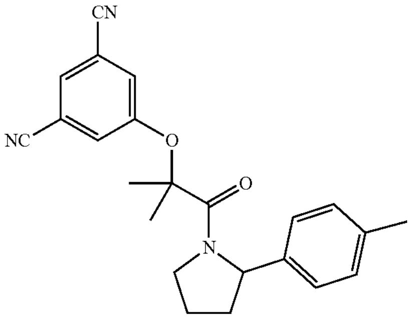 [SMILES: Cc1ccc(C2CCCN2C(=O)C(C)(C)Oc2cc(C#N)cc(C#N)c2)cc1] |
| QY-16-61 | 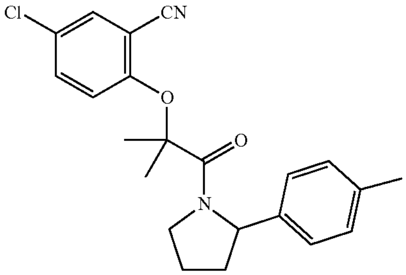 [SMILES: Cc1ccc(C2CCCN2C(=O)C(C)(C)Oc2ccc(Cl)cc2C#N)cc1] | QY-16-66 | 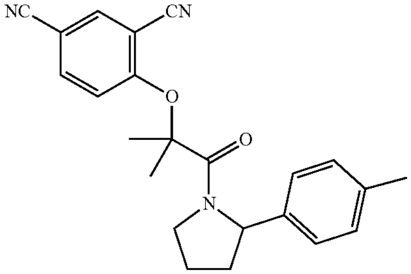 [SMILES: Cc1ccc(C2CCCN2C(=O)C(C)(C)Oc2ccc(C#N)cc2C#N)cc1] |

-continued

| Compound number | Chemical structure | Compound number | Chemical structure |
|---|---|---|---|
| QY-16-75 | 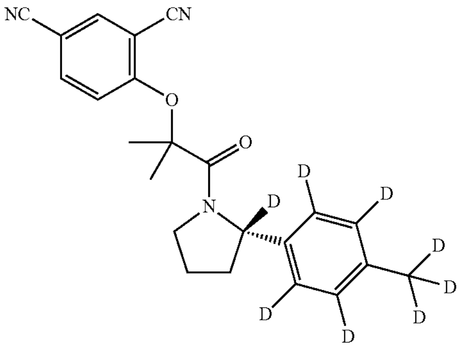 [SMILES: [2H]c1c([2H])c([C@]2([2H])CCCN2C(=O)C(C)(C)Oc2ccc(C#N)cc2C#N)c([2H])c([2H])c1C([2H])([2H])[2H]] | QY-16-76 | 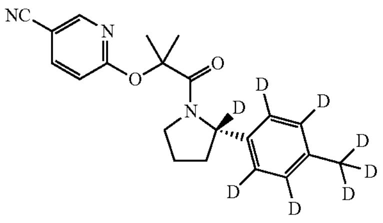 [SMILES: [2H]c1c([2H])c([C@]2([2H])CCCN2C(=O)C(C)(C)Oc2ccc(C#N)cn2)c([2H])c([2H])c1C([2H])([2H])[2H]] |
| QY-16-77 | 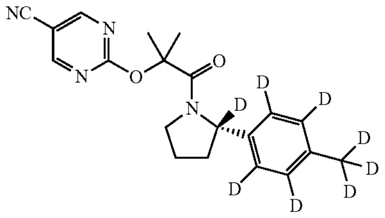 [SMILES: [2H]c1c([2H])c([C@]2([2H])CCCN2C(=O)C(C)(C)Oc2ncc(C#N)cn2)c([2H])c([2H])c1C([2H])([2H])[2H]] | QY-16-82 | 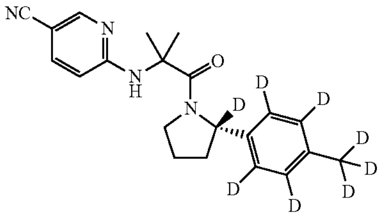 [SMILES: [2H]c1c([2H])c([C@]2([2H])CCCN2C(=O)C(C)(C)Nc2ccc(C#N)cn2)c([2H])c([2H])c1C([2H])([2H])[2H]] |
| and | | | |
| QY-16-84 | 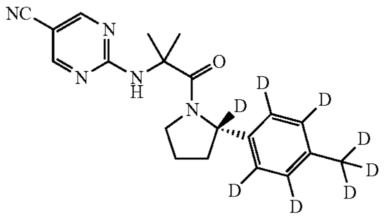 [SMILES: [2H]c1c([2H])c([C@]2([2H])CCCN2C(=O)C(C)(C)Nc2ncc(C#N)cn2)c([2H])c([2H])c1C([2H])([2H])[2H]] | | |

5. A pharmaceutical composition comprising: (a) a therapeutically effective amount of the compound according to claim 1, or pharmaceutically acceptable salts, hydrates or solvates thereof; and (b) a pharmaceutically acceptable carrier.

6. The pharmaceutical composition according to claim 5, wherein diseases or conditions to be treated with the pharmaceutical composition are selected from the group consisting of inflammatory diseases, infectious diseases, ischemic or degenerative-related diseases, and tissue damage.

7. The pharmaceutical composition according to claim 5, wherein diseases or conditions to be treated with the pharmaceutical composition are related to programmed cell necrosis and/or the activity or expression levels of human receptor interacting protein 1 kinase (RIPK1).

8. The pharmaceutical composition according to claim 7, wherein the diseases or conditions are selected from the group consisting of inflammatory diseases, infectious diseases, ischemic or degenerative related diseases, and tissue damage.

9. A method for treating diseases or conditions related to programmed cell necrosis and/or the activity or expression levels of human receptor interacting protein 1 kinase (RIPK1), comprising administering the compound of Formula (I-c) according to claim 1 to a subject in need thereof, wherein the diseases or conditions are selected from the group consisting of inflammatory diseases, infectious diseases, ischemic or degenerative related diseases, and tissue damage.

* * * * *